(12) United States Patent
Cui et al.

(10) Patent No.: US 10,870,701 B2
(45) Date of Patent: Dec. 22, 2020

(54) MULTISPECIFIC FAB FUSION PROTEINS AND USE THEREOF

(71) Applicant: Generon (Shanghai) Corporation Ltd., Shanghai (CN)

(72) Inventors: Yumin Cui, Shanghai (CN); Zhihua Huang, Shanghai (CN); Hanyang Chen, Shanghai (CN); Xinfeng Zhang, Shanghai (CN); Bo Qi, Shanghai (CN); Xiaoqiang Yan, Shanghai (CN)

(73) Assignee: Generon (Shanghai) Corporation Ltd., Shanghai (CN)

( * ) Notice: Subject to any disclaimer, the term of this patent is extended or adjusted under 35 U.S.C. 154(b) by 139 days.

(21) Appl. No.: 16/085,542

(22) PCT Filed: Mar. 15, 2017

(86) PCT No.: PCT/CN2017/076816
§ 371 (c)(1),
(2) Date: Sep. 14, 2018

(87) PCT Pub. No.: WO2017/157305
PCT Pub. Date: Sep. 21, 2017

(65) Prior Publication Data
US 2019/0092862 A1    Mar. 28, 2019

(30) Foreign Application Priority Data

Mar. 15, 2016 (CN) .......................... 2016 1 0147227

(51) Int. Cl.
| | | |
|---|---|---|
| *C07K 16/28* | (2006.01) | |
| *C07K 16/30* | (2006.01) | |
| *A61K 39/395* | (2006.01) | |
| *A61P 35/00* | (2006.01) | |
| *A61K 31/573* | (2006.01) | |
| *C12N 15/62* | (2006.01) | |
| *A61K 39/00* | (2006.01) | |

(52) U.S. Cl.
CPC ........ *C07K 16/2809* (2013.01); *A61K 31/573* (2013.01); *A61P 35/00* (2018.01); *C07K 16/2821* (2013.01); *C07K 16/30* (2013.01); *C07K 16/3023* (2013.01); *C07K 16/3046* (2013.01); *C12N 15/62* (2013.01); *A61K 2039/505* (2013.01); *C07K 2317/31* (2013.01); *C07K 2317/55* (2013.01); *C07K 2317/62* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,237,224 A | 12/1980 | Cohen et al. |
|---|---|---|
| 4,485,045 A | 11/1984 | Regen |
| 4,544,545 A | 10/1985 | Ryan et al. |
| 4,676,980 A | 6/1987 | Segal et al. |
| 4,683,195 A | 7/1987 | Mullis et al. |
| 4,683,202 A | 7/1987 | Mullis |
| 4,751,180 A | 6/1988 | Cousens et al. |
| 4,816,567 A | 3/1989 | Cabilly et al. |
| 4,935,233 A | 6/1990 | Bell et al. |
| 4,946,778 A | 7/1990 | Ladner et al. |
| 5,013,556 A | 5/1991 | Woodle et al. |
| 5,030,719 A | 7/1991 | Umemoto et al. |
| 5,151,510 A | 9/1992 | Stec et al. |
| 5,283,173 A | 2/1994 | Fields et al. |
| 5,468,614 A | 11/1995 | Fields et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,661,016 A | 8/1997 | Lonberg et al. |
| 5,693,761 A | 12/1997 | Queen et al. |
| 5,693,792 A | 12/1997 | Torii et al. |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnson et al. |
| 5,736,137 A | 4/1998 | Anderson et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |

(Continued)

FOREIGN PATENT DOCUMENTS

| CN | 101687915 A | 3/2010 |
|---|---|---|
| CN | 103842383 A | 6/2014 |

(Continued)

OTHER PUBLICATIONS

Adams, et al. (2006, e-pub. Mar. 6, 2006). "Avidity-Mediated Enhancement of in vivo Tumor Targeting By Single-Chain Fv Dimers," Clin. Cancer Res. 12:1599-1605.

(Continued)

*Primary Examiner* — Laura B Goddard
(74) *Attorney, Agent, or Firm* — Morrison & Foerster LLP

(57) ABSTRACT

The present invention provides multispecific Fab fusion proteins (MSFP) that specifically bind to CD3 and EpCAM. The present invention further provides uses of the MSFPs for the preparation of pharmaceutical compositions, methods of treating cancer, and kits comprising the MSFPs. Also provided are anti-EpCAM antibodies or antigen-binding fragments thereof.

20 Claims, 19 Drawing Sheets

Specification includes a Sequence Listing.

(56) References Cited

U.S. PATENT DOCUMENTS

| | | |
|---|---|---|
| 5,814,318 A | 9/1998 | Lonberg et al. |
| 5,837,458 A | 11/1998 | Minshull et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,959,083 A | 9/1999 | Bosslet et al. |
| 6,005,079 A | 12/1999 | Casterman et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg et al. |
| 6,291,158 B1 | 9/2001 | Winter et al. |
| 6,291,161 B1 | 9/2001 | Lerner et al. |
| 6,410,319 B1 | 6/2002 | Raubitschek et al. |
| 6,423,498 B1 | 7/2002 | Markland et al. |
| 6,521,404 B1 | 2/2003 | Griffiths et al. |
| 6,982,321 B2 | 1/2006 | Winter |
| 7,087,409 B2 | 8/2006 | Barbas et al. |
| 7,109,003 B2 | 9/2006 | Hanson et al. |
| 7,115,717 B2 | 10/2006 | Mori et al. |
| 7,288,251 B2 | 10/2007 | Bedian et al. |
| 7,387,776 B2 | 6/2008 | Keler et al. |
| 7,429,644 B2 | 9/2008 | Garber et al. |
| 7,435,797 B2 | 10/2008 | Lowman et al. |
| 7,446,191 B2 | 11/2008 | Jensen |
| 7,462,352 B2 | 12/2008 | Hansen et al. |
| 7,514,537 B2 | 4/2009 | Jensen |
| 7,557,189 B2 | 7/2009 | Hoffee et al. |
| 7,723,482 B2 | 5/2010 | Soulillou et al. |
| 7,723,484 B2 | 5/2010 | Beidler et al. |
| 7,846,440 B2 | 12/2010 | Schoeberl et al. |
| 8,846,042 B2 * | 9/2014 | Zhou ............... A61P 43/00 424/136.1 |
| 8,884,602 B2 | 11/2014 | Utsunomiya |
| 2002/0086014 A1 | 7/2002 | Korman et al. |
| 2002/0142359 A1 | 10/2002 | Copley et al. |
| 2005/0112694 A1 | 5/2005 | Carter et al. |
| 2005/0118183 A1 | 6/2005 | Hoffee et al. |
| 2005/0208043 A1 | 9/2005 | Adams et al. |
| 2005/0232919 A1 | 10/2005 | Grasso et al. |
| 2006/0165686 A1 | 7/2006 | Elson et al. |
| 2006/0177896 A1 | 8/2006 | Mach et al. |
| 2007/0059298 A1 | 3/2007 | Volkmann |
| 2007/0065431 A1 | 3/2007 | Coia et al. |
| 2007/0077246 A1 | 4/2007 | Koenig et al. |
| 2007/0148718 A1 | 6/2007 | Medghalchi et al. |
| 2007/0161783 A1 | 7/2007 | Barbosa et al. |
| 2007/0274981 A1 | 11/2007 | Sun et al. |
| 2007/0287170 A1 | 12/2007 | Davis et al. |
| 2008/0044429 A1 | 2/2008 | Johnson et al. |
| 2008/0286272 A1 | 11/2008 | Lackmann et al. |
| 2009/0155275 A1 | 6/2009 | Wu et al. |
| 2009/0191201 A1 | 7/2009 | Heiss et al. |
| 2009/0202433 A1 | 8/2009 | Chang et al. |
| 2009/0232810 A1 | 9/2009 | Kraus et al. |
| 2009/0304710 A1 | 12/2009 | Park et al. |
| 2010/0003253 A1 | 1/2010 | Laeremans et al. |
| 2010/0003258 A1 | 1/2010 | Weng et al. |
| 2010/0025177 A1 | 2/2010 | Fukushima et al. |
| 2010/0065818 A1 | 3/2010 | Kim et al. |
| 2010/0150918 A1 | 6/2010 | Kufer et al. |
| 2010/0183615 A1 | 7/2010 | Kufer et al. |
| 2010/0189722 A1 | 7/2010 | Heider et al. |
| 2010/0196364 A1 | 8/2010 | Kim et al. |
| 2010/0239582 A1 | 9/2010 | Humphreys et al. |
| 2010/0310463 A1 | 12/2010 | Gunnarsson et al. |
| 2011/0028696 A1 | 2/2011 | Cardarelli et al. |
| 2011/0054151 A1 | 3/2011 | Lazar et al. |
| 2011/0059090 A1 | 3/2011 | Revets et al. |
| 2011/0064653 A1 | 3/2011 | Hansen et al. |
| 2011/0123529 A1 | 5/2011 | Laeremans et al. |
| 2012/0135110 A1 | 5/2012 | Chiba et al. |
| 2012/0244161 A1 | 9/2012 | Zugmeier et al. |
| 2012/0321626 A1 | 12/2012 | Zhou |
| 2015/0056206 A1 | 2/2015 | Zhou |

FOREIGN PATENT DOCUMENTS

| | | |
|---|---|---|
| CN | 104592391 A | 5/2015 |
| CN | 104788567 A | 7/2015 |
| CN | 107184977 A | 9/2017 |
| CN | 107636015 A | 1/2018 |
| CN | 107660151 A | 2/2018 |
| CN | 107903324 A | 4/2018 |
| CN | 108690138 A | 10/2018 |
| EP | 0183070 A2 | 6/1986 |
| EP | 0244234 A2 | 11/1987 |
| EP | 0402226 A1 | 12/1990 |
| EP | 0463151 B1 | 6/1996 |
| EP | 0773288 A2 | 5/1997 |
| EP | 0546073 B1 | 9/1997 |
| EP | 0843961 B1 | 1/2007 |
| JP | 3068180 B2 | 7/2000 |
| JP | 3068506 B2 | 7/2000 |
| JP | 3068507 B2 | 7/2000 |
| JP | 2009-511521 A | 3/2009 |
| JP | 2010-524435 A | 7/2010 |
| JP | 2011-501671 A | 1/2011 |
| WO | WO-1991/00360 A1 | 1/1991 |
| WO | WO-1991/10741 A1 | 7/1991 |
| WO | WO-1992/01047 A1 | 1/1992 |
| WO | WO-1992/03918 A1 | 3/1992 |
| WO | WO-1992/22645 A1 | 12/1992 |
| WO | WO-1992/22647 A1 | 12/1992 |
| WO | WO-1992/22670 A1 | 12/1992 |
| WO | WO-1993/08829 A1 | 5/1993 |
| WO | WO-1993/12227 A1 | 6/1993 |
| WO | WO-1994/00569 A1 | 1/1994 |
| WO | WO-1994/02602 A1 | 2/1994 |
| WO | WO-1994/04678 A1 | 3/1994 |
| WO | WO-1994/09131 A1 | 4/1994 |
| WO | WO-1994/11026 A2 | 5/1994 |
| WO | WO-1994/11026 A3 | 8/1994 |
| WO | WO-1994/25585 A1 | 11/1994 |
| WO | WO-1994/25591 A1 | 11/1994 |
| WO | WO-1995/22618 A1 | 8/1995 |
| WO | WO-1996/14436 A1 | 5/1996 |
| WO | WO-1996/27011 A1 | 9/1996 |
| WO | WO-1996/33735 A1 | 10/1996 |
| WO | WO-1996/34096 A1 | 10/1996 |
| WO | WO-1996/34103 A1 | 10/1996 |
| WO | WO-1997/13852 A1 | 4/1997 |
| WO | WO-1998/24884 A1 | 6/1998 |
| WO | WO-1998/24893 A2 | 6/1998 |
| WO | WO-1998/24893 A3 | 8/1998 |
| WO | WO-1999/37791 A1 | 7/1999 |
| WO | WO-2000/076310 A1 | 12/2000 |
| WO | WO-2000/076310 A9 | 7/2002 |
| WO | WO-2002/077029 A2 | 10/2002 |
| WO | WO-2002/077029 A3 | 5/2003 |
| WO | WO-2004/106380 A2 | 12/2004 |
| WO | WO-2006/072620 A1 | 7/2006 |
| WO | WO-2006/095164 A1 | 9/2006 |
| WO | WO-2006/106959 A1 | 10/2006 |
| WO | WO-2006/114115 A1 | 11/2006 |
| WO | WO-2007/042261 A2 | 4/2007 |
| WO | WO-2007/042261 A3 | 4/2007 |
| WO | WO-2007/065027 A2 | 6/2007 |
| WO | WO-2007/098934 A1 | 9/2007 |
| WO | WO-2008/024188 A2 | 2/2008 |
| WO | WO-2008/024188 A3 | 2/2008 |
| WO | WO-2008/024188 A8 | 7/2008 |
| WO | WO-2008/119566 A2 | 10/2008 |
| WO | WO-2008/119566 A3 | 10/2008 |
| WO | WO-2008/119567 A2 | 10/2008 |
| WO | WO-2008/119567 A3 | 10/2008 |
| WO | WO-2009/052081 A2 | 4/2009 |
| WO | WO-2009/052081 A3 | 4/2009 |
| WO | WO-2009/052081 A4 | 4/2009 |
| WO | WO-2009/068628 A1 | 6/2009 |
| WO | WO-2009/068630 A1 | 6/2009 |

(56) References Cited

FOREIGN PATENT DOCUMENTS

| | | |
|---|---|---|
| WO | WO-2009/149185 A2 | 12/2009 |
| WO | WO-2009/149185 A3 | 12/2009 |
| WO | WO-2010/037836 A2 | 4/2010 |
| WO | WO-2010/037836 A3 | 4/2010 |
| WO | WO-2010/037838 A2 | 4/2010 |
| WO | WO-2010/037838 A3 | 4/2010 |
| WO | WO-2010/052014 A1 | 5/2010 |
| WO | WO-2010/069765 A1 | 6/2010 |
| WO | WO-2010/104949 A2 | 9/2010 |
| WO | WO-2010/145792 A1 | 12/2010 |
| WO | WO-2010/150918 A1 | 12/2010 |
| WO | WO-2011028683 A1 | 3/2011 |
| WO | WO-2011/079258 A1 | 6/2011 |
| WO | WO-2012/158818 A2 | 11/2012 |
| WO | WO-2014/012085 A2 | 1/2014 |
| WO | WO-2014/167022 A1 | 10/2014 |
| WO | WO-2016/055593 A1 | 4/2016 |
| WO | WO-2016/142314 A1 | 9/2016 |
| WO | WO-2016/189014 A1 | 12/2016 |
| WO | WO-2017/055314 A1 | 4/2017 |
| WO | WO-2017/157305 A1 | 9/2017 |
| WO | WO-2018/188612 A1 | 10/2018 |
| WO | WO-2020/048525 A1 | 3/2020 |

OTHER PUBLICATIONS

Adams, R.L.P. (Jul. 1969). "The Effect of Endogenous Pools of Thymidylate on the Apparent Rate of DNA Synthesis," Exp. Cell Res. 56(1):55-58.
Alarcon, B. et al. (Apr. 1991). "The CD3-γ and CD3-δ Subunits of the T Cell Antigen Receptor can be Expressed Within Distinct Functional TCR/CD3 Complexes," EMBO J. 10(4):903-912.
Alt, M. et al. (1999). "Novel Tetravalent and Bispecific IgG-Like Antibody Molecules Combining Single-Chain Diabodies With the Immunoglobulin γ1 Fc or CH3 region," FEES Letters 454:90-94.
Altschul, S.F. et al. (1990). "Basic Local Alignment Search Tool," J. Mol. Biol. 215(3):403-410.
Altschul, S.F. et al. (1997). "Gapped Blast and PSI-Blast: A New Generation of Protein Database Search Programs," Nucl. Acids Res. 25(17):3389-3402.
Amann, M. et al. (Jan. 1, 2008) "Therapeutic Window of MuS110, A Single-Chain Antibody Construct Bispecific For Murine EpCAM and Murine CD3." Cancer Res. 68(1):143-151, 10 pages.
Anasetti, C. et al. (Dec. 1990). "Induction of Specific Nonresponsiveness in Unprimed Human T Cells by Anti-CD3 Antibody and Alloantigen," J. Exp. Med. 172(6):1691-1700.
Baldrick, P. (Oct. 2000). "Pharmaceutical Excipient Development: The Need for Preclinical Guidance," Regul. Toxicol Phaimacol. 32(2):210-218.
Bargou, R. et al. (Aug. 15, 2008). "Tumor Regression in Cancer Patients by Very Low Doses of a T Cell-Engaging Antibody," Science 321(5981):974-977. (English Abstract Only).
Beiboer, S.H.W. et al. (2000). "Guided Selection of a Pan Carcinoma Specific Antibody Reveals Similar Binding Characteristics Yet Structural Divergence Between the Original Murine Antibody and its Human Equivalent," J. Mol. Biol. (2000) 296(3):833-849.
Bellone, S. et al (Jan. 2016). "Solitomab, an EpCAM/CD3 Bispecific Antibody Construct (BiTE), is Highly Active Against Primary Uterine Serous Papillary Carcinoma Cell Lines in Vitro", American Journal of Obstetrics & Gynecology 214(1):99.e1-99.e8, 20 pages.
Bendig, M. M. (1995). "Humanization of Rodent Monoclonal Antibodies by CDR Grafting," Methods: A Companion to Methods in Enzymology 8:83-93.
Berger, C. et al. (Jan. 2008; e-pub. Dec. 3, 2007). "Adoptive Transfer of Effector CD8+ T Cells Derived From Central Memory Cells Establishes Persistent T Cell Memory in Primates," J. Clinical Investigation 118(1):294-305.
Beverley, P.C. et al. (Apr. 1981). "Distinctive Functional Characteristics of Human "T" Lymphocytes Defined by E Rosetting or a Monoclonal Anti-T Cell Antibody," Eur. J. Immunol. 11(4):329-334.

Biotecnol. "TribodyTM Technology," Located at <http://www.biotecnol.com/?tribody-technology>, last visited on Aug. 28, 2018, two pages.
Bird, R.E. et al. (Oct. 21, 1988). "Single-Chain Antigen-Binding Proteins," Science 242:423- 426, 7 pages.
Bloom, L. et al.(Oct. 2009). "FN3: A New Protein Scaffold Reaches the Clinic," Drug Discovery Today 14(19-20):949-955.
Bobo, R.H. et al. (Mar. 15, 1994). "Convection-Enhanced Delivery of Macromolecules in the Brain," Proc. Natl. Acad. Sci. USA 91(6):2076-2080.
Boerner, P. et al. (Jul. 1, 1991). "Production of Antigen-Specific Human Monoclonal Antibodies From in Vitro-Primed Human Splenocytes," J. Immunol. 147(1):86-95.
Borden, P. et al. (Apr. 1, 1987). "Nucleotide Sequence of the cDNAs Encoding the Variable Region Heavy and Light Chains of a Myeloma Protein Specific for the Terminal Nonreducing End of Alpha(1→6)Dextran," PNAS 84(8):2440-2443.
Bottaro, D.P. et al. (1991). "Identification of the Hepatocyte Growth Factor Receptor as the c-met Proto-Oncogene Product," Science 251(4995):802-804.
Bradley, P. et al. (Sep. 16, 2005). "Toward High-Resolution De Novo Structure Prediction for Small Proteins," Science 309(5742):1868-1871, 5 pages.
Brennan, M. et al. (Jul. 5, 1985). "Preparation of Bispecific Antibodies by Chemical Recombination of Monoclonal Immunoglobulin $G_1$ Fragments," Science 229:81-83.
Brooks, B.R. et al. (1983). "CHARMM: A Program for Macromolecular Energy, Minimization, and Dynamics Calculations," J. Comput. Chem. 4(2):187-217.
Bruggemann, M. et al. (1993). "Designer Mice: The Production of Human Antibody Repertoires in Transgenic Animals," Year in Immunol. 7:33-40.
Burbaum, J.J. et al. (1990). "Understanding Structural Relationships of Proteins of Unsolved Three-Dimensional Structure," Proteins 7(2):99-111.
Calaycay, J. et al. (Oct. 5, 1985). "Primary Structure of a DNA- And Heparin-Binding Domain (Domain III) in Human Plasma Fibronectin," J. Biol. Chem. 260(22):12136-12141.
Caron, P.C. et al. (1992; e-pub. Oct. 1, 1992). "Engineered Humanized Dimeric Forms of IgG Are More Effective Antibodies," J. Exp Med. 176:1191-1195.
Carpenter et al. (Apr. 15, 2002). "A Humanized Non-FcR-binding anti-CD3 Antibody, Visilizumab, for Treatment of Steroid-Refractory Acute Graft-Versus-Host Disease," Blood 99(5):2712-2719.
Carter, P. et al. (Feb. 1992). "High Level *Escherichia Coli* Expression and Production of a Bivalent Humanized Antibody Fragment," BioTechnology 10:163-167.
Chames, et al. (Apr. 2009). "Bispecific Antibodies for Cancer Therapy: The Light at the End of the Tunnel?" mAbs 1(6):539-547.
Chang, et al.(May 2002). "Molecular Advances in Pretargeting Radioimmunotherapy with Bispecific Antibodies[1]," Mol Cancer Ther. 1:553-563.
Charman, W.N. (2000, e-pub. Aug. 2000). "Lipids, Lipophilic Drugs, and Oral Drug Delivery—Some Emerging Concepts," Journal of Pharmaceutical Sciences 89(8):967-978.
Chatzigeorgiou, A. et al. (Dec. 2009, e-pub. Nov. 2009). "CD40/CD40L Signaling and Its Implication in Health and Disease," Biofactors. 35(6):474-483.
Chaudhary, V.K. et al. (Feb. 1990). "A Rapid Method of Cloning Functional Variable-Region Antibody Genes in *Escherichia Coli* as Single-Chain Immunotoxins," Proc. Natl. Acad. Sci. U.S.A. 87(3):1066-1070.
Chetty, R. et al. (1994). "CD3: Structure, Function, and Role of Immunostaining in Clinical Practice," J Pathol. 173(4):303-307.
Chiswell, D.J. et al. (1992). "Phage Antibodies: Will New 'Coliclonal' Antibodies Replace Monoclonal Antibodies?," Trends in Biotechnology 10:80-84.
Chothia, C. et al. (1987). "Canonical Structures for the Hypervariable Regions of Immunoglobulins," J. Mol. Biol. 196(4):901-917, 18 pages.
Chothia, C. et al. (Dec. 21-28, 1989). "Conformations of Immunoglobulin Hypervariable Regions," Nature 342(6252):877-883.

(56) References Cited

OTHER PUBLICATIONS

Clackson, T. et al. (Aug. 15, 1991). "Making Antibody Fragments Using Phage Display Libraries," Nature 352(6336):624-628.
Coloma, M. J. et al. (Feb. 1997). "Design and Production of Novel Tetravalent Bispecific Antibodies," Nat. Biotechnol. 15:159-163.
Conrad, M.L. et al. (2007; e-pub. Jul. 25, 2007). "TCR and CD3 Antibody Cross-Reactivity in 44 Species," Cytometry (Part A) 71A:925-933.
Cote, R.J. et al. (Apr. 1983). "Generation of Human Monoclonal Antibodies Reactive With Cellular Antigens," Proc Natl Acad Sci USA 80:2026-2030.
Cwirla, S.E. et al. (Aug. 1990). "Peptides on Phage: A Vast Library of Peptides for Identifying Ligands," PNAS USA 87:6378-6382.
Darke, P.L. et al. (Feb. 5, 1989). "Human Immunodeficiency Virus Protease. Bacterial Expression and Characterization of the Purified Aspartic Protease," J. Biol. Chem. 264(4):2307-2312.
Davidson, B.L. et al. (Mar. 1993). "A Model System for in Vivo Gene Transfer into the Central Nervous System Using an Adenoviral Vector," Nature Genetics 3:219-223.
Davies, D.R. et al. (Jul. 1990). "Antibody-Antigen Complexes," Annual Rev. Biochem. 59:439-473.
Davis, J.H. et al. (2010, e-pub. Feb. 4, 2010). "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Engineering, Design & Selection, 23(4):195-202.
Davis, L.H. et al. (Jun. 15, 1991). "Specific 33-Residue Repeat(s) Erythrocyte Ankyrin Associate with the Anion Exchanger," J. Biol. Chem. 266(17):11163-11169.
Dayhoff, M.O. et al. (1978). "A Model of Evolutionary Change in Proteins," Chapter 22 in Atlas of Protein Sequence and Structure, National Biomedical Research Foundation, Washington DC, 5(3):345-352.
Demydenko, D. et al. (Jun. 2009) "Expression of Galectin-1 in Malignant Tumors," Exp Oncol. 31(2):74-79.
Deyev, S.M. et al. (2008, e-pub. 2008). "Multivalency: The Hallmark of Antibodies Used for Optimization of Tumor Targeting by Design," BioEssays 30:904-918.
Dietz, H. et al. (Jan. 31, 2006). "Protein Structure by Mechanical Triangulation," Proc. Nat. Acad. Sci. USA 103(5):1244-1247.
Dodson, E.J. (Nov. 7-8, 2007). "Computational Biology: Protein Predictions," Nature 450:176-177.
Donate, L.E. et al. (Dec. 1994). "Molecular Evolution and Domain Structure of Plasminogen-related Growth Factors (HGF/SF and HGF1/MSP)," Prat. Sci. 3(12):2378-2394.
Dong, J. et al. (Feb. 11, 2011). "Stable IgG-like Bispecific Antibodies Directed Toward the Type I Insulin-like Growth Factor Receptor Demonstrate Enhanced Ligand Blockade and Anti-tumor Activity," Journal of Biological Chemistry, 286(6):4703-4717.
Ehrlich, P.H. et al. (1980). "Isolation of an Active Heavy-Chain Variable Domain From a Homogeneous Rabbit Antibody by Cathepsin B Digestion of the Aminoethylated Heavy Chain," Biochem 19(17):4091-4096.
Eisenfield, J. et al. (1991; e-published on Aug. 1991). "Constrained Optimization and Protein Structure Determination," Am. J. Physiol. 261:C376-386.
Eppstein, D.A. et al. (Jun. 1985). "Biological Activity of Liposome-Encapsulated Murine Interferon γ Is Mediated by a Cell Membrane Receptor," Proc. Natl. Acad. Sci. USA 82:3688-3692.
Fellouse, F.A. et al. (Aug. 24, 2004). "Synthetic Antibodies from a Four-Amino-Acid Code: A Dominant Role for Tyrosine in Antigen Recognition," PNAS 101(34):12467-12472.
Fishwild, D.M. et al. (Jul. 1996). "High-Avidity Human IgGκ Monoclonal Antibodies from a Novel Strain of Minilocus Transgenic Mice," Nature Biotechnology 14:845-851.
Flaherty, D. K. (2012) Chapter 10 "Antibody Diversity, Immunology for Pharmacy" in Immunology for Pharmacy. St. Louis, Mo.: Elsevier, 12 pages.
Froimowitz, M. (Jun. 1, 1990). "The Development of Computer Simulations of the Geometries and Thermodynamics of Biological Molecules," Biotechniques 8(6):640-644.
Geller, A.I. et al. (Feb. 1995). "An HSV-1 Vector Expressing Tyrosine Hydroxylase Causes Production and Release of I-DOPA from Cultured Rat Striatal Cells," J. Neurochem 64(2):487-496.
Geller, A.I. et al. (Aug. 1993). "Long-Term Increases in Neurotransmitter Release From Neuronal Cells Expressing a Constitutively Active Adenylate Cyclase From a Herpes Simplex Virus Type 1 Vector," Proc Natl. Acad. Sci. U.S.A. 90:7603-7607.
Geller, A.I. et al. (Feb. 1990). "Infection of Cultured Central Nervous System Neurons With a Defective Herpes Simplex Virus 1 Vector Results in Stable Expression of *Escherichia Coli* β-Galactosidase," Proc Natl. Acad. Sci. USA 87:1149-1153.
Gorman, C.M. et al. (Nov. 1982). "The Rous Sarcoma Virus Long Terminal Repeat is a Strong Promoter When Introduced Into a Variety of Eukaryotic Cells by DNA-Mediated Transfection," Proc Natl. Acad. Sci. U.S.A. 79:6777-6781.
Graham, F.L. et al. (Jul. 1977). "Characteristics of a Human Cell Line Transformed by DNA From Human Adenovirus Type 5," J. Gen Virol. 36(1):59-74.
Green, L.L. et al. (May 1994). "Antigen-Specific Human Monoclonal Antibodies From Mice Engineered With Human Ig Heavy and Light Chain YACs," Nature Genetics 7(1):13-21.
Grosschedl, R. et al. (Jul. 1985). "Cell-Type Specificity of Immunoglobulin Gene Expression is Regulated by at Least Three DNA Sequence Elements," Cell 41(3):885-897.
Grosse-Hovest, L. et al. (2003). "A Recombinant Bispecific Single-Chain Antibody Induces Targeted, Supra-Agonistic CD28-Stimulation and Tumor Cell Killing," Eur.J. Immunol. 33:1334-1340.
Gruber, M. et al. (1994). "Efficient Tumor Cell Lysis Mediated by a Bispecific Single Chain Antibody Expressed in *Escherichia Coli*," The Journal of Immunology 152(11):5368-5374.
Gunasekaran, K, et al. (Jun. 18, 2010). "Enhancing Antibody Fc Heterodimer Formation through Electrostatic Steering Effects: Applications to Bispecific Molecules and Monovalent IgG," Journal of Biological Chemistry 285(25):19637-19646.
Guss, B. et al. (Jul. 1986). "Structure of the IgG-Binding Regions of Streptococcal Protein G," EMBO J. 5(7):1567-1575.
Hamers-Casterman, C. et al. (Jun. 3, 1993). "Naturally Occurring Antibodies Devoid of Light Chains," Nature 363(6428):446-448.
Hanes et al. (May 1997). "In Vitro Selection and Evolution of Functional Proteins by Using Ribosome Display," Proc Natl. Acad. Sci. U.S.A. 94:4937-4942.
Harris, W.J. (Nov. 1, 1995). "Therapeutic Monoclonals: Production of Humanized Monoclonal Antibodies for in Vivo Imaging and Therapy," Biochem. Soc. Transactions 23(4):1035-1038.
Hein, J. (1990). "Unified Approach to Alignment and Phylogenies," Methods in Enzymology 183:626-645.
Henikoff, S. et al. (Nov. 15, 1992). "Amino Acid Substitution Matrices from Protein Blocks," Proc. Natl. Acad. Sci. USA 89(22):10915-10919.
Herold. K.C. et al. (Feb. 1, 2003). "Activation of Human T Cells by FcR Nonbinding Anti-CD3 mAb, HOKT3γ1(Ala-Ala)," J. Clin. Invest. 111(3):409-418.
Higgins, D.G. et al. (1989). "Fast and Sensitive Multiple Sequence Alignments on a Microcomputer," Comput Appl Biosci. 5(2):151-153.
Hirsch, R. et al. (Jun. 1988). "Effects of in Vivo Administration of Anti-T3 Monoclonal Antibody on T Cell Function in Mice: I. Immunosuppression if Transplantation Responses," J. Immunol. 140(11):3766-3772.
Hochman, J. et al.(1976). "Folding and Interaction of Subunits at the Antibody Combining Site," Biochem 15(12):2706-2710.
Holliger, P. et al. (Jul. 1993). ""Diabodies": Small Bivalent and Bispecific Antibody Fragments," Proceedings of the National Academy of Sciences 90:6444-6448.
Holt, L.J. et al.(Nov. 2003). "Domain Antibodies: Proteins for Therapy," Trends in Biotechnology 21(11):484-490.
Hongo, J.S. et al. (1995). "Development and Characterization of Murine Monoclonal Antibodies to the Latency-Associated Peptide of Transforming Growth Factor $β_1$," Hybridoma 14(3):253-260.

(56) References Cited

OTHER PUBLICATIONS

Hoogenboom, H.R. et al. (1992). "By-Passing Immunisation. Human Antibodies from Synthetic Repertoires of Germline Hh Gene Segments Rearranged in Vitro," Journal of Molecular Biology 227:381-388.
Hoogenboom, H.R. et al. (Dec. 1992). "Building Antibodies from their Genes," Immunol. Reviews 130(1):41-68.
Hurle, M.R. et al. (Aug. 1994)."Protein Engineering Techniques for Antibody Humanization," Current Opinion in Biotechnology 5:428-433.
Huse, W.D. et al. (Dec. 8, 1989). "Generation of a Large Combinatorial Library of the Immunoglobulin Repertoire in Phage Lambda," Science 246(4935):1275-1281.
Huston, J.S. et al. (Aug. 1988). "Protein Engineering of Antibody Binding Sites: Recovery of Specific Activity in an Anti-Digoxin Single-Chain Fv Analogue Produced in *Escherichia Coli*," Proc. Natl. Acad. Sci. U.S.A. 85(16):5879-5883.
Hwang, K.J. et al. (Jul. 1980). "Hepatic Uptake and Degradation of Unilamellar Sphingomyelin/Cholesterol Liposomes: A Kinetic Study," Proc. Natl Acad. Sci. USA 77(7):4030-4034.
Inbar, D. et al. (Sep. 1972). "Localization of Antibody-Combining Sites Within the Variable Portions of Heavy and Light Chains," Proc. Nat. Acad. Sci. USA 69(9):2659-2662.
International Preliminary Report on Patentability Chapter I dated Sep. 18, 2018 for International Application No. PCT/CN2017/076816, filed on Mar. 15, 2017, 7 pages.
International Preliminary Report on Patentability dated Nov. 28, 2013, for Patent Application No. PCT/US2012/038177 filed on May 16, 2012, 7 pages.
International Search Report dated Nov. 14, 2012, Patent Application No. PCT/US2012/038177 filed on May 16, 2012, 10 pages.
International Search Report dated Dec. 17, 2019 for International Patent Application No. PCT/CN2019/104680, filed on Sep. 6, 2019, 7 pages.
International Search Report dated Jun. 21, 2017 for International Patent Application No. PCT/CN2017/076816, filed on Mar. 15, 2017, 6 pages.
Jakobovits, A. et al. (Mar. 18, 1993) "Germ-line Transmission and Expression of a Human-derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-chain Joining Region Blocks B-Cell Development and Antibody Production," Proceedings of the National Academy of Sciences 90:2551-2555.
Jansen, F.K. et al. (Feb. 1982). "Immunotoxins: Hybrid Molecules Combining High Specificity and Potent Cytotoxicity," Immunological Reviews 62(1):185-216.
Jiang, T. et al. (Dec. 21, 2004; e-pub Dec. 15, 2004). "Tumor Imaging by Means of Proteolytic Activation of Cell-Penetrating Peptides," Proc. Natl. Acad. Sci. U.S.A. 101(51):17867-17872.
Johnson, et al. (2010, e-pub. Apr. 9, 2020). "Effector Cell Recruitment with Novel Fv-based Dual-affinity Re-targeting Protein Leads to Potent Tumor Cytolysis and in Vivo B-cell Depletion," J Mol. Biol. 399:436-449.
Johnson, G. et al. (2003). "The Kabat Database and a Bioinformatics Example," Methods in Molecular Biology 248:1-25. (Abstract Only, 1 page).
Jones, P.T. et al. (May 29, 1986). "Replacing the Complementarity-Determining Regions in a Human Antibody with Those from a Mouse," Nature 321:522-525.
Kaplitt, M.G. et al. (Oct. 1994). "Long-Term Gene Expression and Phenotypic Correction Using Adeno-Associated Virus Vectors in the Mammalian Brain," Nature Genetics 8:148-154.
Killen J.A. et al. (Nov. 1984) "Specific killing of lymphocytes that cause experimental autoimmune myasthenia gravis by ricin toxin-acetylcholine receptor conjugates," J. Immunol. 133(5):2549-2553.
Kini, R.M. et al. (1991, e-pub May 21, 2012). "Molecular Modeling of Proteins: A Strategy for Energy Minimization by Molecular Mechanics in the AMBER Force Field," J. Biomol. Struct. Dyn. 9(3):475-488, 16 pages.

Kipriyanov, S.M. (2004). "Recent Advances in the Generation of Bispecific Antibodies for Tumor Immunotherapy," Curr. Opin. Drug Discov. Devel. 7:233-242.
Kipriyanov, et al., "Bispecific tandem diabody for tumor therapy with improved antigen binding and pharmacokinetics," J Mal. Biol., 293:41-56, (1999).
Kipriyanov, S.M. et al. (Dec. 31, 1998). "Bispecific CD3xCD19 Diabody for T Cell-Mediated Lysis of Malignant Human B Cells," Int. J. Cancer 77:763-772.
Klimka, A. et al. (Jun. 20, 2000). "Human Anti-CD30 Recombinant Antibodies by Guided Phage Antibody Selection Using Cell Panning," British Journal of Cancer 83(2):252-260.
Koch-Nolte, F. et al. (2007; e-pub. Jun. 15, 2007). "Single Domain Antibodies From Llama Effectively and Specifically Block T Cell Ecto-ADP-Ribosyltransferase ART2.2 in vivo," Faseb J. 21:3490-3498.
Kohler, G. et al. (Aug. 7, 1975). "Continuous Cultures of Fused Cells Secreting Antibody of Predefined Specificity," Nature 256:495-497.
Koide, A. et al. (2007). "Monobodies: Antibody Mimics Based on the Scaffold of the Fibronectin Type III Domain," Methods Mol. Biol. 352:95-109.
Koide, A. et al.(Dec. 11, 1998). "The Fibronectin Type III Domain as a Scaffold for Novel Binding Proteins," J. Mol. Biol. 284(4):1141-1151.
Kontermann, (Jan. 2005). "Recombinant bispecific antibodies for cancer therapy," Acta Pharmacol. Sin. 26(1):1-9.
Kostelny, S.A. et al. (Mar. 1, 1992). "Formation of a Bispecific Antibody by the Use of Leucine Zippers," The Journal of Immunology 148(5):1547-1553.
Kozbor, D. et al. (Dec. 1984). "A Human Hybrid Myeloma for Production of Human Monoclonal Antibodies," The Journal of Immunology 133(6):3001-3005.
Kozbor, D. et al. (Mar. 1983). "The Production of Monoclonal Antibodies From Human Lymphocytes," Immunology Today 4(3):72-79.
La Rocca, G. et al. (Apr. 5, 2004; e-pub. Mar. 16, 2004). "Zymographic Detection and Clinical Correlations of MMP-2 and MMP-9 in Breast Cancer Sera," British J. of Cancer 90(7):1414-1421.
Laplanche, L.A. et al. (Nov. 25, 1986). "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucl. Acids Res. 14(22):9081-9093.
Lavasani, S. et al. (2007; e-pub. Dec. 14, 2006). "Monoclonal Antibody against T-Cell Receptor αβ Induces Self-Tolerance in Chronic Experimental Autoimmune Encephalomyelitis," Scandinavian Journal of Immunology 65(1):39-47.
Lavie, G. et al. (Apr. 1, 2000). "Inhibition of the CD8+ T Cell-Mediated Cytotoxicity Reaction by Hypericin: Potential for Treatment of T Cell-Mediated Diseases," International Immunology 12(4):479-486.
Le Gal La Salle, G. et al. (Feb. 12, 1993). "An Adenovirus Vector for Gene Transfer Into Neurons and Glia in the Brain," Science 259(5097):988-990.
Lee, C.V. et al. (2004). "Bivalent Antibody Phage Display Mimics Natural Immunoglobulin," Journal of Immunological Methods 284(1-2):119-132.
Lee, C.V. et al.(2004). "High-affinity Human Antibodies from Phage-displayed Synthetic Fab Libraries with a Single Framework Scaffold," Journal of Molecular Biology 340:1073-1093.
Li J. et al.(Mar. 7, 2006). "Human Antibodies for Immunotherapy Development Generated via a Human B Cell Hybridoma Technology," PNAS 103(10):3557-3562.
Lindmark, R. et al. (Aug. 12, 1983). "Binding of Immunoglobulins to Protein A and Immunoglobulin Levels in Mammalian Sera," J. Immunol. Meth. 62(1):1-13.
Liu, A.Y. et al. (May 1987). "Chimeric Mouse-Human IgG1 Antibody That Can Mediate Lysis of Cancer Cells," Proc Natl Acad Sci U S A. 84(10):3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.

(56) References Cited

OTHER PUBLICATIONS

Liu, et al. (Jun. 5, 2010). "Efficient Inhibition of Human B-cell Lymphoma in SCID Mice by Synergistic Antitumor Effect of Human 4-IBB Ligand/anti-CD20 Fusion Proteins and Anti-CD3/anti-CD20 Diabodies ," J Immunother. 33(5):500-509.

Lonberg, N. et al. (1995). "Human Antibodies from Transgenic Mice," International Reviews of Immunology. 13(1):65-93.

Lonberg, N. et al. (Apr. 28, 1994). "Antigen-Specific Human Antibodies from Mice Comprising Four Distinct Genetic Modifications," Nature 368:856-859.

Lu, D. et al. (2002). "Fab-scFv Fusion Protein: an Efficient Approach to Production of Bispecific Antibody Fragments," Journal of Immunological Methods 267:213-226.

Lybrand, T.P. (Jan.-Feb. 1991). "Molecular Simulation and Drug Design," J. Pharm. Belg. 46(1):49-54. (Abstract Only, 1 page).

Mabry, R. et al. (2010, e-pub. Dec. 18, 2009). "Engineering of Stable Bispecific Antibodies Targeting IL-17A and IL-23," Protein Eng Des Sel. 23(3):115-127.

Mack, M. et al. (Jul. 1995). "A Small Bispecific Antibody Construct Expressed As A Functional Single-Chain Molecule With High Tumor Cell Cytotoxic," Proc. Natl. Acad. Sci. USA. 92:7021-7025.

Maratea, D. et al. (1985). "Deletion and Fusion Analysis of the Phage φ X174 Lysis Gene E.," Gene 40(1):39-46.

Marks, J.D. et al. (Dec. 1991). "By-Passing Immunization: Human Antibodies From V-Gene Libraries Displayed on Phage," Journal of Molecular Biology 222(3):581-597.

Marks, J.D. et al. (Jul. 1992)."By-Passing Immunization: Building High Affinity Human Antibodies by Chain Shuffling," Biotechnology 10(7):779-783.

Martin, F.J. et al. (Jan. 10, 1982). "Irreversible Coupling of Immunoglobulin Fragments to Preformed Vesicles," J. Biol. Chem. 257(1):286-288.

Marvin, J.S. et al. (Jun. 2005). "Recombinant Approaches to IgG-like Bispecific Antibodies," Acta Pharmacol. Sin. 26(6):649-658.

Mather, J.P. (Aug. 1980). "Establishment and Characterization of Two Distinct Mouse Testicular Epithelial Cell Lines," Biol. Reprod. 23(1):243-252.

Mather, J.P. et al. (1982). "Culture of Testicular Cells in Hormone-Supplemented Serum-Free Medium," Annals N. Y. Acad. Sci. 383:44-68.

Mau-Sorensen, M. et al. (May 2015, e-pub. Mar. 27, 2015). "A Phase I Trial of Intravenous Catumaxomab: A Bispecific Monoclonal Antibody Targeting EpCAM and the T Cell Coreceptor CD3," Cancer Chemotherapy and Pharmacology 75(5):1065-1073.

Merchant, M.A. et al. (Jul. 1998). "An efficient route to human bispecific IgG," Nat Biotechnol. 16:677-681.

Mertens, N. et al. (2004). "New Strategies in Polypeptide and Antibody Synthesis: An Overview," Cancer Biotherapy & Radiopharmaceuticals 19(1):99-109.

Meylan, F. et al. (Jul. 18, 2008; Jun. 19, 2008). "The TNF-Family Receptor DR3 is Essential for Diverse T cell-mediated Inflammatory Diseases," Immunity 29(1):79-89, twenty six pages.

Michaelson, J.S. et al. (Mar./Apr. 2009). "Anti-Tumor Activity of Stability-Engineered IgG-like Bispecific Antibodies Targeting Trail-R2 and LTbetaR ," mAbs, 1:2:128-141.

Miller, B.R. et al. (2010, e-pub. May 10, 2010). "Stability engineering of scFvs for the development of bispecific and multivalent antibodies," Protein EnR Des Sel. 23(7):549-557.

Milstein, C. et al. (Oct. 6, 1983). "Hybrid Hybridomas and their use in Immunohistochemistry," Nature 305:537-540.

Morrison, P.F. et al. (1994). "High Flow Microinfusion: Tissue Penetration and Pharmacodynamics," Am. J. Physiol. 266:R292-R305.

Morrison, S.L. (Apr. 28, 1994). "Success in Specification," Nature 368:812-813.

Morrison, S.L. et al. (Nov. 1984). "Chimeric Human Antibody Molecules: Mouse Antigen-binding Domains with Human Constant Region Domains," Proc. Nat'l Acad. Sci 81:6851-6855.

Muller, D. et al. (2010). "Bispecific Antibodies for Cancer Immunotherapy: Current Perspectives," Biodrugs 24(2):89-98.

Munson, P.J. et al. (1980). "Ligand: A Versatile Computerized Approach for Characterization of Ligand-binding Systems," Analytical Biochemistry 107:220-239.

Munz, M. et al. (Nov. 2, 2010) "Side-by-side analysis of five clinically tested anti-EpCAM monoclonal antibodies." Cancer Cell Int. 10(44):1-12.

Murphy, J.R. et al. (Nov. 1986). "Genetic Construction, Expression, and Melanoma-Selective Cytotoxicity of a Diphtheria Toxin-Related Alpha-Melanocyte-Stimulating Hormone Fusion Protein," Proc. Natl. Acad. Sci. USA 83(21):8258-8262.

Myers, E.W. et al. (1988). "Optimal Alignments in Llinear Space," Comput Appl Biosci. 4(1):11- 17.

Needleman, S.B. et al. (Mar. 28, 1970). "A General Method Applicable to the Search for Similarities in the Amino Acid Sequence of Two Proteins," J. Mol. Biol. 48(3):443-453.

Nelson, A.L. et al. (Oct. 2010; e-pub Sep. 3, 2010). "Development Trends for Human Monoclonal Antibody Therapeutics," Nature Reviews Drug Discovery 9(10):767-774.

Neuberger, M. (Jul. 1996). "Generating High-Avidity Human Mabs in Mice," Nature Biotechnology 14:826, one page.

Nguyen, V.K. et al. (Apr. 2002; Feb. 26, 2002). "Heavy-Chain Antibodies in Camelidae; A Case of Evolutionary Innovation," Immunogenetics 54(1):39-47.

Nguyen, V.K. et al. (Jan. 23, 1998). "The Specific Variable Domain of Camel Heavy-Chain Antibodies is Encoded in the Germline," J. Mol. Biol. 275(3):413-418.

Nilson, B. H. K. at al. (Feb. 5, 1992). "Protein L From Peptostreptococcus Magnus Binds to the Kappa Light Chain Variable Domain," J. Biol. Chem. 267(4):2234-2239.

Obeidy, P. et al. (Dec. 2009, e-pub. Jul. 22, 2009). "NKG2D and its Ligands," Int J Biochem Cell Biol. 41(12):2364-2367.

O'Hare, M. et al. (Oct. 29, 1990). "Cytotoxicity of a Recombinant Ricin-A-Chain Fusion Protein Containing a Proteolytically-Cleavable Spacer Sequence," FEBS Lett. 273(1-2):200-204.

Okayama, H. et al. (Feb. 1983). "A cDNA Cloning Vector That Permits Expression of cDNA Inserts in Mammalian Cells," Molecular and Cellular Biology 3(2):280-289.

Olson, E.S. et al. (Mar. 2, 2010). "Activatable Cell Penetrating Peptides Linked to Nanoparticles as Dual Probes for in Vivo Fluorescence and MR Imaging of Proteases," Proc. Natl. Acad. Sci. USA 107(9):4311-4316.

Orcutt, K.D. et al. (2010, e-pub. Dec. 17, 2009). "A modular IgG-scFv Bispecific Antibody Topology," Protein Eng Des Sel. 23(4):221-228.

Ortho Multicenter Transplant Study Group "A Randomized Clinical Trial of OKT3 Monoclonal Antibody for Acute Rejection of Cadaveric Renal Transplants. Ortho Multicenter Transplant Study Group," N Engl. J Med., 313:337-342, (1985).

Otz, T. et al. (2009, e-pub. Oct. 2, 2008). "A Bispecific Single-Chain Antibody That Mediates Target Cell-Restricted, Supra-Agonistic CD28 Stimulation and Killing of Lymphoma Cells," Leukemia, 23:71-77.

Parmley, S.F. et al. (1988). "Antibody-Selectable Filamentous fd Phage Vectors: Affinity Purification of Target Genes," Gene 73:305-318.

Paul, W.E. (ed.). (1993). "Fv Structure and Diversity in Three Dimensions," in Chapter 9 of Fundamental Immunology, 3rd Edition, Raven Press, 1185 Avenue of the Americas, New York, NY 10036, pp. 292-295, six pages.

Pearson, W.R. et al. (Apr. 1, 1988). "Improved Tools for Biological Sequence Comparison," Proc. Natl. Acad. Sci. USA 85(8):2444-2448.

Pedersen, L. (Sep. 1985). "Conformational Properties of Molecules by ab Initio Quantum Mechanical Energy Minimization," Environmental Health Perspectives 61:185-190.

Pessano, S. et al. (1985). "The T3/T Cell Receptor Complex: Antigenic Distinction Between the Two 20-kd T3 (T3-delta and T3-epsilon) Subunits," The EMBO J. 4(2):337-344.

Pluckthun, A. (Jun. 1991). "Antibody Engineering: Advances From the Use of *Escherichia coli* Expression Systems," Bio/Technology 9:545-551.

Pluckthun, A. (Oct. 4, 1990). "Antibodies from *Escherichia coli*," Nature 347(6292):497-498.

(56) References Cited

OTHER PUBLICATIONS

Portolano, S. et al. (Feb. 1, 1993). "Lack of Promiscuity in Autoantigen-Specific H and L Chain Combinations as Revealed by Human H and L Chain "Roulette"," The Journal of Immunology 150(3):880-887.
Powell, M.F. et al. (Sep.-Oct. 1998). "Compendium of Excipients for Parenteral Foimulations," PDA J Pharm Sci Technol. 52(5):238-311. (Abstract page only).
Prell, R.A. et al. (2013, e-pub. Jun. 28, 2013) "Catumaxomab (EpCAM/CD3 Multi-targeting Full-length Antibody)" Chpater 14 in Nonclinical Development of Novel Biologics, Biosimilars, Vaccines and Specialty Biologics, book, abstract only, 2 pages.
Presta, L.G. (1992). "Antibody Engineering," Current Opinion in Structural Biology 2:593-596.
Qian, B. et al. (Nov. 8, 2007). "High-Resolution Structure Prediction and the Crystallographic Phase Problem," Nature 450(7167):259-264, twenty three pages.
Rader, C. et al. (Jul. 21, 1998). "A Phage Display Approach for Rapid Antibody Humanization: Designed Combinatorial V Gene Libraries," Proc. Natl. Acad. Sci. USA 95(15):8910-8915.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Raman, S. et al. (Feb. 19, 2010). "NMR Structure Determination for Larger Proteins Using Backbone-Only Data," Science 327(5968):1014-1018, twelve pages.
Reff, M.E. (Oct. 1993). "High-Level Production of Recombinant Immunoglobulins in Mammalian Cells," Curr. Opinion Biotech. 4(5):573-576.
Reynolds, J.A. (1979). "Interaction of Divalent Antibody With Cell Surface Antigens," Biochemistry 18(2):264-269.
Ridgway, J.B.B. et al. (1996). "'Knobs-Into-Holes' Engineering of Antibody CH3 Domains for Heavy Chain Heterodimerization," Protein Engineering 9(7):617-621.
Riechmann, L. et al. (Dec. 10, 1999). "Single Domain Antibodies: Comparison of Camel VH and Camelised Human VH Domains," J. Immunol. Methods 231(1-2):25-38.
Riechmann, L. et al. (Mar. 24, 1988). "Reshaping Human Antibodies for Therapy," Nature 332:323-327.
Robinson, D.F. (1971). "Comparison of Labeled Trees with Valency Three," Comb. Theor. 11:105-119.
Robinson, M.K. et al. (2008, e-pub. Oct. 7, 2008). "Targeting ErbB2 and ErbB3 with a bispecific single-chain Fv enhances targeting selectivity and induces a therapeutic effect in vitro," British Journal of Cancer 99:1415-1425.
Roux, K.H. et al. (Sep. 29, 1998). "Structural Analysis of the Nurse Shark (New) Antigen Receptor (NAR): Molecular Convergence of NAR and Unusual Mammalian Immunoglobulins," Proc. Natl. Acad. Sci. USA 95(20):11804-11809.
Rudikoff, S. et al. (Mar. 1982). "Single Amino Acid Substitution Altering Antigen-Binding Specificity," Proc. Natl. Acad. Sci. USA 79:1979-1983.
Russell, S.J. et al. (1993). "Retroviral Vectors Displaying Functional Antibody Fragments," Nucl. Acids Research 21(5):1081-1085.
Saitou, N. et al. (Jul. 1, 1987). "The Neighbor-Joining Method: A New Method for Reconstructing Phylogenetic Trees," Mol. Biol. Evol. 4(4):406-425.
Salmeron, A. et al. (Nov. 1, 1991). "A Conformational Epitope Expressed Upon Association of CD3-Epsilon With Either CD3-Delta or CD3-Gamma Is the Main Target for Recognition by Anti-CD3 Monoclonal Antibodies," J. Immunol. 147(9):3047-3052.
Scatchard, G. (May 1949). "The Attractions of Proteins for Small Molecules and Ions," Annals of the New York Academy of Sciences 51(4):660-672.
Schaefer, W. et al. (Jul. 5, 2011; e-pub. Jun. 20, 2011). "Immunoglobulin Domain Crossover as a Generic Approach for the Production of Bispecific IgG Antibodies," Proc. Natl. Acad. Sci. USA 108(27):111870-111892.
Schmidt, M. et al. (Feb. 1, 2010, e-pub. Jul. 24, 2009). "An Open-Label, Randomized Phase II Study of Adecatumumab, A Fully Human Anti-Epcam Antibody, As Monotherapy in Patients With Metastatic Breast Cancer," Annals of Oncology 21(2):275-282.
Schoonjans, R. et al. (2000). "Fab Chains as an Efficient Heterodimerization Scaffold for the Production of Recombinant Bispecific and Trispecific Antibody Derivatives," Journal of Immunology 165:7050-7057.
Schueler-Furman, O. et al. (Oct. 28, 2005). "Progress in Modeling of Protein Structures and Interactions," Science 310(5748):638-642.
Schwartzberg, L.S. (Oct. 2001). "Clinical Experience With Edrecolomab: A Monoclonal Antibody Therapy for Colorectal Carcinoma," Critical Reviews in Oncology/ Hematology 40(1):17-24.
Scott, J.K. (Jul. 1992). "Discovering peptide ligands using epitope libraries," Trends in Biochemical Sciences 17(7):241-245.
Shalaby, M.F. et al. (Jan. 1992). "Development of Humanized Bispecific Antibodies Reactive with Cytotoxic Lymphocytes and Tumor Cells Overexpressing the HER2 Protooncogene," The Journal of Experimental Medicine 175:217-225.
Shen, J. et al. (2007, e-pub. Oct. 26, 2006). "Single Variable Domain Antibody as a Versatile Building Block for the Construction of lgg-Like Bispecific Antibodies," J Immunol. Methods 318:65-74.
Shen, J. et al. (Apr. 21, 2006). "Single Variable Domain-lgg Fusion. A Novel Recombinant Approach to Fe Domain-Containing Bispecific Antibodies," J Biol. Chem. 281(16):10706-10714.
Shen, H.M. et al. (Aug. 1, 2006). "TNF Receptor Superfamily-Induced Cell Death: Redox-Dependent Execution," FASEB J. 20(10):1589-1598.
Sheriff, S. et al. (Sep. 1996). "Redefining the Minimal Antigen-binding Fragment," Nature Structural & Molecular Biology 3(9):733-736.
Shopes, B. (May 1, 1992). "A Genetically Engineered Human IgG Mutant With Enhanced Cytolytic Activity," J. Immunol. 148(9):2918-2922.
Sidhu, S.S. et al. (Apr. 2004). "Phage-displayed Antibody Libraries of Synthetic Heavy Chain Complementarity Determining Regions," Journal of Molecular Biology 338(2):299-310.
Smith, T.F. et al. (1981). "Comparison of Bio-Sequences," Adv. Appl. Math. 2:482-489.
Staerz, U.D. et al. (Mar. 1986). "Hybrid hybridoma producing a bispecific monoclonal antibody that can focus effector T-cell activity," Proc Natl Acad Sci USA, 83:1453-1457.
Stec, W.J. et al. (1984). "Automated Solid-Phase Synthesis, Separation, and Stereochemistry of Phosphorothioate Analogs of Oligodeoxyribonucleotides," J. Am. Chem. Soc. 106(20):6077-6079.
Stein, C.A. et al. (Apr. 25, 1988). "Physicochemical Properties of Phospborothioate Oligodeoxynucleotides," Nucl. Acids Res. 16(8):3209-3221.
Stevenson, G.T. et al. (Mar. 1989). "A Chimeric Antibody With Dual Fc Regions (Bisfabfc) Prepared by Manipulations at the IgG Hinge," Anti-Cancer Drug Design 3(4):219-230.
Suresh, M.R. et al. (1986). "Bispecific Monoclonal Antibodies from Hybrid Hybridomas," Methods in Enzymology 121:210-228.
Third Party Observation submitted on Apr. 9, 2013 for International Application No. PCT/US2012/038177, filed on May 16, 2012, two pages.
Torkildsen, O. et al. (Mar. 24, 2006). "FcγR and Multiple Sclerosis: An Overview," Acta Neural Scand Suppl. 113(Suppl. 183):61-63.
Traunecker, A. et al. (1991). "Bispecific Single Chain Molecules (Janusins) Target Cytotoxic Lymphocytes on HIV Infected Cells," The EMBO Journal 10(12):3655-3659.
Trill, J.J. et al. (Oct. 1995). "Production of Monoclonal Antibodies in COS and CHO Cells," Curr. Opinion Biotech 6(5):553-560.
Turk, B.E. et al. (Jul. 1, 2001). "Determination of Protease Cleavage Site Motifs Using Mixture-Based Oriented Peptide Libraries," Nature Biotechnology 19:661-667.
Tutt, A. et al. (Jul. 1, 1991). "Trispecific F(Ab')3 Derivatives That Use Cooperative Signaling via the TCR/CD3 Complex and CD2 to Activate and Redirect Resting Cytotoxic T Cells," J. Immunol. 147(1):60-69.

(56) References Cited

OTHER PUBLICATIONS

Uhlmann, E. et al. (Jun. 1990). "Antisense Oligonucleotides: A New Therapeutic Principle," Chemical Reviews 90(4):543-584.
Urlaub, G. et al. (Jul. 1, 1980). "Isolation of Chinese Hamster Cell Mutants Deficient in Dihydrofolate Reductase Activity," Proc. Natl. Acad. Sci. USA 77(7):4216-4220.
Van Dijk, M.A et al. (2001). "Human Antibodies as Next Generation Therapeutics," Current Opinion in Chemical Biology 5:368-374.
Vaswani, S.K. et al. (Aug. 1998). "Humanized Antibodies as Potential Therapeutic Drugs," Annals of Allergy, Asthma & Immunology 81:105-119.
Vitetta, E.S. et al. (Nov. 20, 1987). "Redesigning Nature's Poisons to Create Anti-Tumor Reagents," Science 238:1098-1104.
Wang, W. (Aug. 1, 2000). "Lyophilization and Development of Solid Protein Pharmaceuticals," Int. J. Pharm. 203(1-2):1-60.
Weiner, S.J. et al (Feb. 1984). "A New Force Field for Molecular Mechanical Simulation of Nucleic Acids and Proteins," J. Comput. Chem. 106(3):765-784.
Weisel, J.W. et al. (Dec. 20, 1985). "A Model for Fibrinogen: Domains and Sequence," Science 230(4732):1388-1391.
Westby, M. et al. (Sep.-Oct. 1992). "Preparation and Characterization of Recombinant Proricin Containing an Alternative Protease-Sensitive Linker Sequence," Bioconjugate Chemistry 3(5):375-381.
Wilbur, W.J. et al. (Feb. 1, 1983). "Rapid Similarity Searches of Nucleic Acid and Protein Data Banks," Proc. Natl. Acad. Sci. USA 80(3):726-730.
Willems, A. et al. (2005, e-pub. May 13, 2005). "CD3 X CD28 Cross-Interacting Bispecific Antibodies Improve Tumor Cell Dependent T-Cell Activation," Cancer Immunol Immunother 54: 1059-1071.
Winter, G. et al. (Jun. 1993). "Humanized Antibodies," Immunol Today 14(6):243-246.
Wright, A. et al. (1992) "Genetically Engineered Antibodies: Progress and Prospects," Crit. Rev Immunol. 12(3-4)125-168.
Written Opinion of the International Searching Authority dated Dec. 17, 2019 for International Patent Application No. PCT/CN2019/104680, filed on Sep. 6, 2019, five pages.
Written Opinion of the International Searching Authority dated Jun. 21, 2017 for International Patent Application No. PCT/CN2017/076816, filed on Mar. 15, 2017, six pages.
Written Opinion of the International Searching Authority dated Nov. 14, 2012 for International Patent Application No. PCT/US2012/038177, filed on May 16, 2012, 5 pages.
Wu, C. et al. (Nov. 2007, e-pub. Oct. 14, 2007). "Simultaneous Targeting of Multiple Disease Mediators by a Dual-Variable-Domain Immunoglobulin," Nat. Biotechnol. 25(11):1290-1297.
Wu, T.T. et al. (Aug. 1, 1970). "An Analysis of the Sequences of the Variable Regions of Bence Jones Proteins and Myeloma Light Chains and their Implications for Antibody Complementarity," J. Exp. Med. 132(2):211-250.
Wu, X. et al. (Mar. 16, 2015, e-pub. May 1, 2015). "Fab-based Bispecific Antibody Formats With Robust Biophysical Properties and Biological Activity," *MABs*. 7(3):470-482.
Xu, J. L. et al. (Jul. 2000). "Diversity in the CDR3 Region of VH Is Sufficient for Most Antibody Specificities," Immunity 13:37-45.
Yang, S.Y. et al. (Aug. 15, 1986). "A Common Pathway for T Lymphocyte Activation Involving Both the CD3-Ti Complex and CD2 Sheep Erythrocyte Receptor Determinants," J. Immunol. 137(4):1097-1100.
Yang, Y. et al. (Apr. 1995). "Cellular and Humoral Immune Responses to Viral Antigens Create Barriers to Lung-Directed Gene Therapy with Recombinant Adenoviruses," J. Virol. 69(4):2004-2015, 21 pages.
Yoshino, N. et al. (2000). "Upgrading of Flow Cytometric Analysis for Absolute Counts, Cytokines and Other Antigenic Molecules of Cynomolgus Monkeys (Macaca Fascicularis) by Using Anti-Human Cross-Reactive Antibodies," Exp. Anim 49(2):97-110.
Zelensky, A.N. et al. (Dec. 2005; e-pub. Nov. 28, 2005). "The C-Type Lectin-Like Domain Superfamily," FEBS J. 272(24):6179-6217.
Zettlitz, K.A. (2010). "Protein A/G Chromatography," Chapter 34 in Antibody Engineering, Kontermann, R. (ed.) et al., Springer, Berlin, Heidelberg, 2nd Edition, Part V, 531-535.
Zhang, P. et al. (Feb. 1, 2014, e-pub. Nov. 1, 2013). "An EpCAM/CD3 Bispecific Antibody Efficiently Eliminates Hepatocellular Carcinoma Cells with Limited Galectin-1 Expression," Cancer Immunology Immunotherapy 63(2):121-132.
Zon, G. et al. (Dec. 1, 1991). "Phosphorothioate Oligonucleotides: Chemistry, Purification, Analysis, Scale-Up and Future Directions," Anti-Cancer Drug Design 6(6):539-568.

* cited by examiner

MULTISPECIFIC FAB FUSION PROTEINS AND USE THEREOF

CROSS REFERENCE TO RELATED APPLICATIONS

This application is a National Phase filing under 35 U.S.C. § 371 of International Application No. PCT/CN2017/076816 having an international filing date of Mar. 15, 2017, which claims priority benefit of Chinese Patent Application No. 201610147227.8 filed Mar. 15, 2016, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720622000841SEQLIST.txt, date recorded: Mar. 13, 2017, size: 48 KB).

FIELD OF THE INVENTION

The present invention relates to multi-specific Fab fusion proteins (MSFP) that specifically bind to CD3 and EpCAM. Further provided herein are pharmaceutical compositions comprising the MSFPs, methods of treating cancer using the MSFPs, and kits comprising the MSFPs.

BACKGROUND OF THE INVENTION

Some antigens are over-expressed, mutagenized, or selectively mutagenized in tumor tissues. Therefore, antibodies targeting specific antigens on the surface of cancer cells can be used as cancer therapeutics. Epithelial cell adhesion molecule (EpCAM, CD326), also known as 17-1A, ESA, AUA1, EGP40, etc., is a 40 kD transmembrane glycoprotein composed of 314 amino acid. EpCAM is specifically expressed in various types of epithelial cells, and major types of human malignancies. For example, EpCAM is highly expressed in colon cancer, lung cancer, prostate cancer, liver cancer, pancreatic cancer, breast cancer and ovarian cancer. Thus, EpCAM has become a hot target in cancer therapy, including vaccines, murine or human monoclonal antibodies, and antibodies conjugated to bacterial toxins or chemotherapy drugs, such as EpCAM specific antibodies ING-1, adecatumumab, edrecolomab, etc.

CD3, comprising three different polypeptide chains (ε, δ and γ chains), is an antigen expressed by T cells. The three CD3 polypeptide chains associate with the T-cell receptor (TCR) and the ζ-chain to form the TCR complex, which has the function of activating signaling cascades in T cells. Currently, many therapeutic strategies target the TCR signal transduction to treat diseases using anti-human CD3 monoclonal antibodies. The CD3 specific antibody OKT3 is the first monoclonal antibody approved for human therapeutic use, and is clinically used as an immunomodulator for the treatment of allogenic transplant rejections.

During the past twenty years, efforts in the field of bispecific antibodies have gradually yielded clinical success. In 2009, Catumaxomab (anti-CD3, anti-EpCAM trifunctional antibody) was approved in the European Union for the treatment of symptomatic malignant ascites. However, although bispecific antibodies have been shown to have potential in effectively killing cancer cells, severe adverse effects, including systemic immune activation, immunogenicity (anti-drug antibody effect), and the generally poor manufacturability of these molecules, have greatly limited the widespread application of this type of drugs. Another drawback of CD19×CD3 bispecific scFv-scFv (single-chain variable fragment) fusion protein (Blinatumomab) is that this drug needs to be administered intravenously (i.v.) on a daily basis due to its short half-life and incompatibility with subcutaneous administration; yet, neurological effects such as disorientation, confusion, speech and language impairment, tremor or convulsion still occurred during clinical trials (Science 321:974-977, 2008). To better control these unwanted adverse effects, bispecific single-chain antibodies (BiTE) were administered intravenously with continuous infusion over a longer period of time. US20120244161 disclosed the stage I clinical trial of EpCAM×CD3 bispecific scFv-scFv fusion protein (MT110), in which low dosage (1-12 μg/kg/24 hr) continuous intravenous infusion was applied over a long period of time, with glucocorticoid administered prior to MT110 infusion or dosage increment. Furthermore, scFv-scFv fusion protein has a tendency for aggregation.

The drawbacks of current formats of bispecific antibodies remain great challenges for their widespread application in the treatment of cancer patients with good efficacy and safety. Therefore, there is an urgent need in the field for the development of new bispecific antibodies or treatment regimen with improved efficacy, stability, safety and manufacturability.

BRIEF SUMMARY OF THE INVENTION

The present invention provides multi-specific Fab fusion proteins (such as bispecific Fab fusion proteins, or BSFP) that specifically bind to CD3 and EpCAM, and methods of treating cancer using the MSFPs.

In one aspect of the present invention, there is provided a method of treating a cancer in an individual (such as a human individual), comprising administering to the individual an effective amount of a multispecific (such as bispecific) Fab fusion protein comprising: a Fab fragment that specifically binds to CD3, and a binding domain that specifically binds to EpCAM; wherein the binding domain is fused to an N-terminus of the Fab fragment; and wherein the multispecific Fab fusion protein is administered at a dose of about 0.01 μg/kg to about 250 μg/kg (such as about 0.01 μg/kg to about 5 μg/kg, about 0.1 μg/kg to about 30 μg/kg, or about 2.5 μg/kg to about 100 μg/kg). In some embodiments, the binding domain is an scFv. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence.

In some embodiments according to any of the methods described above, the multispecific Fab fusion protein is administered intravenously. In some embodiments, the multispecific Fab fusion protein is administered at a low frequency (such as any of less than about once per 1, 2, 3, 4, 6, 9, or 12 months, such as a single dose). In some embodiments, the multispecific Fab fusion protein is administered at a dose equivalent to about 0.1 μg/kg to about 100 μg/kg (such as about 0.3 μg/kg to about 5 μg/kg, or about 5 μg/kg to about 20 μg/kg) for a cynomolgus monkey. In some embodiments, the multispecific Fab fusion protein is administered at a dose that does not induce cytokine storm. In some embodiments, the multispecific Fab fusion protein is administered at a dose equivalent to no higher than about 30 µg/kg (such as no higher than about 20 µg/kg, 10 µg/kg, or 1 µg/kg) for a cynomolgus monkey. In some embodiments, the individual is a human individual.

In some embodiments according to any of the methods described above, the multispecific Fab fusion protein is administered at a first dose for a first period of time to the individual, and subsequently, the multispecific Fab fusion protein is administered at a second dose for a second period of time to the individual, and wherein the second dose exceeds the first dose. In some embodiments, the second period of time exceeds the first period of time. In some embodiments, the first period of time is at least about 7 days. In some embodiments, the second period of time is at least about 2 weeks. In some embodiments, the first dose is no more than about 1 µg/kg. In some embodiments, the second dose is about 0.1 µg/kg to about 10 µg/kg.

In some embodiments according to any of the methods described above, the method further comprises administering a glucocorticoid to the individual. In some embodiments, the glucocorticoid is dexamethasone. In some embodiments, the glucocorticoid is administered prior to the first dose of the multispecific Fab fusion protein. In some embodiments, the glucocorticoid is administered at a dose of about 0.1 mg/kg to about 5 mg/kg.

In some embodiments according to any of the methods described above, the Fab fragment specifically binds to the N-terminus of CD3 epsilon, such as an epitope within amino acids 1-27 of CD3 epsilon. In some embodiments, the VH of the Fab fragment comprises: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3. In some embodiments, the VL of the Fab fragment comprises a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the VH of the Fab fragment comprises an amino acid sequence having at least about 85% (such as about 100%) sequence identity to an amino acid sequence selected from SEQ ID NOs: 7 and 39-43. In some embodiments, the VL of the Fab fragment comprises an amino acid sequence having at least about 85% (such as about 100%) sequence identity to an amino acid sequence selected from SEQ ID NOs: 8 and 44-47. In some embodiments, the Fab fragment comprises a human immunoglobulin heavy chain constant region 1 (CH1) comprising the amino acid sequence of SEQ ID NO:9. In some embodiments, the Fab fragment comprises a human lambda light chain constant region comprising the amino acid sequence of SEQ ID NO:10. In some embodiments, the CH1 and the CL of the Fab fragment are connected by one or more disulfide bonds. In some embodiments, the Fab fragment comprises a first polypeptide comprising an amino acid sequence having at least about 85% (such as about 100%) sequence identity to the amino acid sequence of SEQ ID NO: 11. In some embodiments, the Fab fragment comprises a second polypeptide comprising an amino acid sequence having at least about 85% (such as about 100%) sequence identity to the amino acid sequence of SEQ ID NO: 12.

In some embodiments according to any of the methods described above, the cancer is an EpCAM-positive solid cancer. In some embodiments, the EpCAM-positive solid cancer is a carcinoma or adenocarcinoma. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, endometrial cancer, breast cancer, bile duct cancer, and head and neck cancer. In one embodiment, the cancer is colorectal adenocarcinoma. In one embodiment, the cancer is lung adenocarcinoma.

In some embodiments according to any of the methods described above, the binding domain (such as scFv) comprises an N-VH-VL-C fusion polypeptide. In some embodiments, the VH of the scFv comprises a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15. In some embodiments, the VL of the scFv comprises a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the VH of the scFv comprises an amino acid sequence having at least about 85% (such as about 100%) sequence identity to the amino acid sequence of SEQ ID NO:19. In some embodiments, the VL of the scFv comprises an amino acid sequence having at least about 85% (such as about 100%) sequence identity to the amino acid sequence of SEQ ID NO:20. In some embodiments, the scFv comprises an amino acid sequence having at least about 85% (such as about 100%) sequence identity to the amino acid sequence of SEQ ID NO:21.

In some embodiments according to any of the methods described above, the multispecific Fab fusion protein comprises a first polypeptide comprising an amino acid sequence having at least about 85% (such as about 100%) sequence identity to the amino acid sequence of SEQ ID NO:22. In some embodiments, the multispecific Fab fusion protein comprises a second polypeptide comprising an amino acid sequence having at least about 85% (such as about 100%) sequence identity to the amino acid sequence of SEQ ID NO:23.

The present invention further provides an anti-EpCAM antibody. In some embodiments, there is provided an anti-EpCAM antibody or antigen-binding fragment thereof, comprising a heavy chain variable region comprising: (1) a HVR-H1 comprising the amino acid sequence of SEQ ID NO:13; (2) a HVR-H2 comprising the amino acid sequence of SEQ ID NO:14; and (3) a HVR-H3 comprising the amino acid sequence of SEQ ID NO:15; and a light chain variable region comprising: (1) a HVR-L1 comprising the amino acid sequence of SEQ ID NO:16; (2) a HVR-L2 comprising the amino acid sequence of SEQ ID NO:17; and (3) a HVR-L3 comprising the amino acid sequence of SEQ ID NO:18. In some embodiments, the heavy chain variable domain sequence comprises a VH comprising an amino acid sequence having at least about 85% (such as about 100%) sequence identity to the amino acid sequence of SEQ ID NO:19.1n some embodiments, the light chain variable domain sequence comprises a VL comprising an amino acid sequence having at least about 85% (such as about 100%) sequence identity to the amino acid sequence of SEQ ID NO:20.

In some embodiments according to any one of the anti-EpCAM antibodies described above, the anti-EpCAM antibody comprises an Fc sequence of a human IgG. In some embodiments, the anti-EpCAM antibody is a multispecific antibody, such as a bispecific antibody.

In some embodiments according to any one of the anti-EpCAM antigen-binding fragments described above, the antigen-binding fragment is a single-chain Fv (scFv). In some embodiments, the scFv comprises an amino acid sequence having at least about 85% (such as about 100%) sequence identity to the amino acid sequence of SEQ ID NO: 21.

In some embodiments, there is provided a multispecific (such as bispecific) Fab fusion protein comprising any one of the anti-EpCAM antigen-binding fragments described above. In some embodiments, the multispecific Fab fusion protein comprises a Fab fragment that specifically binds to CD3, a first copy of the anti-EpCAM antigen-binding fragment, and a second copy of the anti-EpCAM antigen binding fragment; wherein the first copy of the anti-EpCAM antigen-binding fragment is fused to the N-terminus of the VH of the Fab fragment; and wherein the second copy of the anti-EpCAM antigen binding fragment is fused to the N-terminus of the VL of the Fab fragment. In some embodiments, the Fab fragment specifically binds to the N-terminus of CD3 epsilon, such as an epitope within amino acids 1-27 of CD3 epsilon. In some embodiments, the VH of the Fab fragment comprises a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3. In some embodiments, the VL of the Fab fragment comprises: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the VH of the Fab fragment comprises an amino acid sequence having at least about 85% (such as about 100%) sequence identity to an amino acid sequence selected from the group consisting of SEQ ID NOs:7 and 39-43. In some embodiments, the VL of the Fab fragment comprises an amino acid sequence having at least about 85% (such as about 100%) sequence identity to an amino acid sequence selected from the group consisting of SEQ ID NOs: 8 and 44-47. In some embodiments, the Fab fragment comprises a human immunoglobulin heavy chain constant region 1 (CH1) comprising the amino acid sequence of SEQ ID NO:9. In some embodiments, the Fab fragment comprises a human lambda light chain constant region comprising the amino acid sequence of SEQ ID NO:10. In some embodiments, the CH1 and the CL of the Fab fragment are connected by one or more disulfide bonds. In some embodiments, the Fab fragment comprises a first polypeptide comprising an amino acid sequence having at least about 85% (such as about 100%) sequence identity to the amino acid sequence of SEQ ID NO:11. In some embodiments, the Fab fragment comprises a second polypeptide comprising an amino acid sequence having at least about 85% (such as about 100%) sequence identity to the amino acid sequence of SEQ ID NO:12. In some embodiments, the multispecific (such as bispecific) Fab fusion protein comprising a first polypeptide comprising an amino acid sequence having at least about 85% (such as about 100%) sequence identity to the amino acid sequence of SEQ ID NO:22, and a second polypeptide comprising an amino acid sequence having at least about 85% (such as about 100%) sequence identity to the amino acid sequence of SEQ ID NO:23.

In some embodiments, there is provided a composition comprising any of the anti-EpCAM antibodies or antigen-binding fragments thereof or the multispecific Fab fusion proteins described above and a pharmaceutically acceptable carrier. In some embodiments, there is provided a method of treating cancer in an individual, comprising administering an effective amount of the composition to the individual.

Further provided are isolated nucleic acid molecules that encode the MSFPs, anti-EpCAM antibodies or antigen-binding fragments thereof described above, expression vectors encoding the isolated nucleic acid molecules, isolated host cells comprising the expression vectors, and methods of producing the MSFPs, anti-EpCAM antibodies or antigen-binding fragments thereof, comprising culturing the isolated host cells and recovering the MSFPs, anti-EpCAM antibodies or antigen-binding fragments thereof from the cell culture.

Also provided herein are uses, compositions (such as pharmaceutical compositions), kits and articles of manufactures comprising any of the multispecific Fab fusion proteins or the anti-EpCAM antibodies or antigen-binding fragments thereof described above.

Use of any of the multispecific Fab fusion proteins described above or any of the anti-EpCAM antibodies or antigen-binding fragments thereof described above in the preparation of a medicament for treating a cancer is further provided herein.

These and other aspects and advantages of the present invention will become apparent from the subsequent detailed description and the appended claims. It is to be understood that one, some, or all of the properties of the various embodiments described herein may be combined to form other embodiments of the present invention.

The disclosures of all publications, patents, patent applications and published patent applications referred to herein are hereby incorporated herein by reference in their entirety.

DETAILED DESCRIPTION OF THE INVENTION

Figure 1:
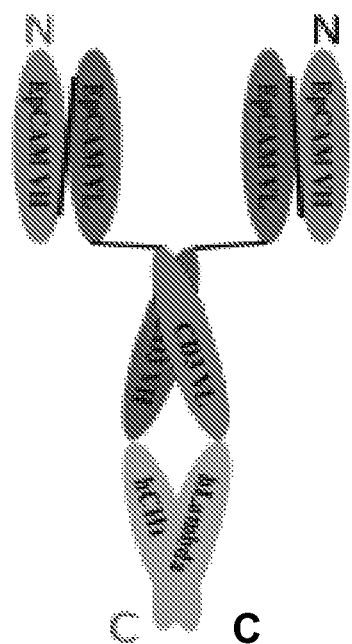
FIG. 1 depicts the structure of an exemplary EpCAM× CD3 Fab fusion protein.

The present invention provides methods of treating cancer using a multispecific Fab fusion protein (MSFP) comprising a Fab fragment that specifically binds to CD3, and a binding domain (such as scFv) that specifically binds to EpCAM. In some embodiments, the MSFP comprises an anti-CD3 Fab fragment having the N-termini of its heavy chain and light chain polypeptides each fused to an anti-EpCAM scFv. Unlike current anti-cancer bispecific antibodies in the art, which suffer from poor manufacturability, aggregation, short half-life, severe adverse effects, and long infusion time, the multispecific Fab fusion proteins described herein have improved stability and safety profiles, which enabled methods of treatment using lower dosage and decreased dosing frequency, avoiding undesirable adverse effects, such as induction of cytokine storm. Decreased dosing frequency and shortened infusion time facilitate the treatment of patients, conducive to improving the quality of life of patients. For example, it was surprisingly found that the MSFPs described herein can be administered at a dose of about 0.01 µg/kg to about 250 µg/kg, such as about 0.01 µg/kg to about 5 µg/kg, about 0.1 µg/kg to about 30 µg/kg, or about 2.5 µg/kg to about 100 µg/kg. Further provided are novel anti-EpCAM antibodies or antigen-binding fragments thereof.

The MSFPs described herein have the following advantages compared to other multispecific Fab fusion proteins known in the art. The MSFPs have higher stability, and enhanced efficacy in killing cancer cells. The extended half-life of the present MSFPs enable lower dosing frequency and shorter infusion time, providing more convenience to the patients. The cross-reactivity of the present MSFPs with primates, such as cynomolgus monkeys, facilitates toxicology studies. The present MSFPs have fewer adverse effects, including diminished neural effects, good safety and tolerance in cynomolgus monkeys.

Accordingly, in one aspect, the present invention provides a method of treating a cancer in an individual, comprising administering to the individual an effective amount of a multispecific (such as bispecific) Fab fusion protein comprising a Fab fragment that specifically binds to CD3, and a binding domain (such as scFv) that specifically binds to EpCAM, wherein the binding domain is fused to an N-terminus of the Fab fragment, and wherein the multispecific Fab fusion protein is administered at a dose of about 0.01

µg/kg to about 250 µg/kg (such as about 0.01 µg/kg to about 5 µg/kg, about 0.1 µg/kg to about 30 µg/kg, or about 2.5 µg/kg to about 100 µg/kg).

In another aspect, the present invention provides an anti-EpCAM antibody or antigen-binding fragment thereof, comprising a heavy chain variable region comprising (1) a HVR-H1 comprising the amino acid sequence of SEQ ID NO: 13; (2) a HVR-H2 comprising the amino acid sequence of SEQ ID NO: 14; and (3) a HVR-H3 comprising the amino acid sequence of SEQ ID NO: 15; and a light chain variable region comprising (1) a HVR-L1 comprising the amino acid sequence of SEQ ID NO:16; (2) a HVR-L2 comprising the amino acid sequence of SEQ ID NO:17; and (3) a HVR-L3 comprising the amino acid sequence of SEQ ID NO:18.

Also provided are kits and articles manufacture useful for the methods described herein.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al, Short Protocols in Molecular Biology, 3$^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, an "effective amount" refers to an amount of an agent or drug effective to treat a disease or disorder in a subject. In the case of cancer, the effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, an "individual" or a "subject" refers to a mammal, including, but not limited to, human, bovine, horse, feline, canine, rodent, or primate. In some embodiments, the individual is a human.

The term "antibody" is used in the broadest sense and specifically covers monoclonal antibodies (including full length monoclonal antibodies), multispecific antibodies (e.g., bispecific antibodies), and antibody fragments so long as they exhibit the desired biological activity or function. As used herein, the terms "immunoglobulin" (Ig) and "antibody" are used interchangeably.

The terms "native antibody", "full length antibody," "intact antibody" and "whole antibody" are used herein interchangeably to refer to an antibody in its substantially intact form, not antibody fragments as defined below. The terms particularly refer to an antibody with heavy chains that contain an Fc region. Native antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs, also referred to as CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("κ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment has two polypeptide chains, containing the heavy- and light-chain variable domains, and also containing the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, The Pharmacology of Monoclonal Antibodies. Springer Berlin Heidelberg, 1994, 269-315.

The "Fc" fragment comprises the carboxy-terminal portions of both H chains held together by di-sulfides. The effector functions of antibodies are determined by sequences in the Fc region, which region is also the part recognized by Fc receptors (FcR) found on certain types of cells.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In some embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature 256:495-97 (1975); Hongo et al., Hybridoma 14 (3): 253-260 (1995), Harlow et al., Antibodies: A Laboratory Manual, (Cold Spring Harbor Laboratory Press, 2nd ed. 1988); Hammerling et al., Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol. 227: 381 (1991); Marks et al., J. Mol. Biol. 222:581 (1991). Also available for the preparation of human monoclonal antibodies are methods described in Cole et al., Monoclonal Antibodies and Cancer Therapy, Alan R. Liss, 77 (1985); Boerner et al., J. Immunol. 147(1):86-95 (1991). See also van Dijk and van de Winkel, Curr. Opin. Pharmacol. 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). HVR is also referred to as "CDR" or "complementarity determining region".

The structures and locations of immunoglobulin variable regions may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

"Framework" or "FR" residues are those variable domain residues other than the HVR residues as herein defined.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In some embodiments, an antibody that specifically binds to a target has a dissociation constant (Kd) of ≤100 nM, ≤10 nM, ≤1 nM, or ≤0.1 nM. In some embodiments, an antibody specifically binds to an epitope on a protein that is conserved among the protein from different species. In another embodiment, specific binding can include, but does not require exclusive binding.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table A. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

As used herein, a "Fab fusion protein" refers to a protein having a Fab fragment covalently linked to one or more binding domains that have different characteristics compared to the Fab fragment. The characteristics may be biological characteristics, such as in vitro or in vivo activity. The characteristics may also be simple chemical or physical properties, such as binding to a target molecule, catalytic reactions, and the like. The Fab fragment and the one or more binding domains may be directly connected by a single peptide bond, or connected via a peptide linker, but to each other in an in-frame manner.

The term "multispecific" as used in conjunction with an antibody (such as a Fab fusion protein) refers to an antibody (such as a Fab fusion protein) having polyepitopic specificity (i.e., is capable of specifically binding to two, three, or more, different epitopes on one biological molecule or is capable of specifically binding to epitopes on two, three, or more, different biological molecules).

The term "bispecific" as used in conjunction with an antibody (such as a Fab fusion protein) refers to an antibody (such as a Fab fusion protein) capable of specifically binding to two different epitopes on one biological molecule, or capable of specifically binding to epitopes on two different biological molecules. Unless otherwise indicated, the order in which the antigens bound by a bispecific antibody are listed in a bispecific antibody or Fab fusion protein name is arbitrary. That is, the terms "anti-CD3/EpCAM," "anti-EpCAM/CD3," "EpCAM×CD3" and "CD3×EpCAM" may be used interchangeably to refer to bispecific antibodies (such as bispecific Fab fusion proteins) that specifically bind to both CD3 and EpCAM.

The terms "multispecific Fab fusion protein" and "MSFP" are used herein interchangeably to refer to a Fab fusion protein that has polyepitopic specificity.

As used herein, the "C terminus" of a polypeptide refers to the last amino acid residue of the polypeptide which donates its amine group to form a peptide bond with the carboxyl group of its adjacent amino acid residue. "N terminus" of a polypeptide as used herein refers to the first amino acid of the polypeptide which donates its carboxyl group to form a peptide bond with the amine group of its adjacent amino acid residue.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "cell" includes the primary subject cell and its progeny.

The term "cytokine storm," also known as a "cytokine cascade" or "hypercytokinemia," is a potentially fatal immune reaction typically consisting of a positive feedback loop between cytokines and immune cells, with highly elevated levels of various cytokines (e.g. INF-γ, IL-10, IL-6, CCL2, etc.).

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Methods of Treating Cancer

One aspect of the present application provides a method of treating a cancer in an individual (such as a human), comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain (such as scFv) is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the multispecific Fab fusion protein is administered intravenously. In some embodiments, the multispecific Fab fusion protein is administered at a low frequency. In some embodiments, the method does not induce cytokine storm.

In some embodiments, there is provided a method of killing cancer cells in an individual (such as a human), comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain (such as scFv) is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the tumor cell death rate mediated by the MSFP is at least about any of 40%, 50%, 60%, 70%, 80%, 90%, 95%, or more. In some embodiments, the multispecific Fab fusion protein is administered intravenously. In some embodiments, the multispecific Fab fusion protein is administered at a low frequency. In some embodiments, the method does not induce cytokine storm. In some embodiments, the method further comprises administering a glucocorticoid (such as dexamethasone) to the individual.

In some embodiments, there is provided a method of inhibiting proliferation of cancer cells in an individual (such as a human), comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain (such as scFv) is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the multispecific Fab fusion protein is administered intravenously. In some embodiments, the multispecific Fab fusion protein is administered at a low frequency. In some embodiments, the method does not induce cytokine storm. In some embodiments, the method further comprises administering a glucocorticoid (such as dexamethasone) to the individual.

In some embodiments, there is provided a method of inducing redistribution of peripheral T cells in an individual (such as a human), comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the multispecific Fab fusion protein is administered intravenously. In some embodiments, the multispecific Fab fusion protein is administered at a low frequency. In some embodiments, the method does not induce cytokine storm. In some embodiments, the method further comprises administering a glucocorticoid (such as dexamethasone) to the individual.

In some embodiments, the MSFP is a bispecific Fab fusion protein that specifically binds to CD3 and EpCAM.

In some embodiments, the MSFP specifically binds to more than two (such as 3 or more) epitopes. In some embodiments, the MSFP is a trispecific Fab fusion protein further comprising a binding domain (such as an scFv) that specifically binds to a cell surface protein, such as a tumor antigen, that is not EpCAM. In some embodiments, the MSFP comprises a multispecific (such as bispecific) binding domain.

In some embodiments, the MSFP comprise a single binding domain that specifically binds to EpCAM. In some embodiments, the binding domain comprises a single polypeptide chain. In some embodiments, the binding domain is an scFv. In some embodiments, the single binding domain is fused to the N-terminus of the heavy chain polypeptide of the Fab fragment. In some embodiments, the single binding domain is fused to the N-terminus of the light chain polypeptide of the Fab fragment.

In some embodiments, the MSFP comprises two binding domains that specifically bind to EpCAM. In some embodiments, the two binding domains target the same epitope in EpCAM. In some embodiments, the two binding domains have the same amino acid sequence. In some embodiments, the two binding domains have different amino acid sequences. In some embodiments, the two binding domains target different epitopes in EpCAM. In some embodiments, each of the two binding domains comprises a single polypeptide chain. In some embodiments, each of the two binding domains is an scFv. In some embodiments, one binding domain is fused to the N-terminus of the heavy chain polypeptide of the Fab fragment, and the other binding domain is fused to the N-terminus of the light chain polypeptide of the Fab fragment.

Thus, in some embodiments, there is provided a method of treating a cancer in an individual (such as a human), comprising administering to the individual an effective amount of a multispecific (such as bispecific) Fab fusion protein comprising: (1) a Fab fragment that specifically binds to CD3; (2) a first binding domain (such as an scFv) that specifically binds to EpCAM; (3) and a second binding domain (such as an scFv) that specifically binds to EpCAM, wherein the first scFv is fused to the N-terminus of the VH of the Fab fragment, wherein the second scFv is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of killing cancer cells in an individual (such as a human), comprising administering to the individual an effective amount of a multispecific (such as bispecific) Fab fusion protein comprising: (1) a Fab fragment that specifically binds to CD3; (2) a first binding domain (such as an scFv) that specifically binds to EpCAM; (3) and a second binding domain (such as an scFv) that specifically binds to EpCAM, wherein the first scFv is fused to the N-terminus of the VH of the Fab fragment, wherein the second scFv is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of inhibiting proliferation of cancer cells in an individual (such as a human), comprising administering to the individual an effective amount of a multispecific (such as bispecific) Fab fusion protein comprising: (1) a Fab fragment that specifically binds to CD3; (2) a first binding domain (such as an scFv) that specifically binds to EpCAM; (3) and a second binding domain (such as an scFv) that specifically binds to EpCAM, wherein the first scFv is fused to the N-terminus of the VH of the Fab fragment, wherein the second scFv is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of inducing redistribution of peripheral T cells in an individual (such as a human), comprising administering to the individual an effective amount of a multispecific (such as bispecific) Fab fusion protein comprising: (1) a Fab fragment that specifically binds to CD3; (2) a first binding domain (such as an scFv) that specifically binds to EpCAM; (3) and a second binding domain (such as an scFv) that specifically binds to EpCAM, wherein the first scFv is fused to the N-terminus of the VH of the Fab fragment, wherein the second scFv is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

The Fab fragment may be derived from any suitable anti-CD3 antibodies known in the art. In some embodiments, the Fab fragment specifically binds to the N-terminus of CD3 epsilon. In some embodiments, the Fab fragment specifically binds to an epitope within amino acids 1-27 of CD3 epsilon. In some embodiments, the Fab fragment is derived from SP34. In some embodiments, the Fab fragment comprises any one, two, or three HVRs (or CDRs) of the heavy chain variable region of SP34, such as HVRs comprising the amino acid sequences of SEQ ID NOs: 1-3. In some embodiments, the Fab fragment comprises any one, two, or three HVRs (or CDRs) of the light chain variable region of SP34, such as HVRs comprising the amino acid sequences of SEQ ID NOs: 4-6. In some embodiments, the Fab fragment comprises the VH of SP34, such as the VH comprising an amino acid sequence selected from SEQ ID NOs: 7 and 39-43. In some embodiments, the Fab fragment comprises the VL of SP34, such as the VL comprising an amino acid sequence selected from SEQ ID NOs:8 and 44-47. In some embodiments, the Fab fragment comprises a human immunoglobulin heavy chain constant region 1 (CH1), such as the CH1 comprising the amino acid sequence of SEQ ID NO: 9. In some embodiments, the CH1 and the CL of the Fab fragment are connected by one or more disulfide bonds. In some embodiments, the Fab fragment comprises a first polypeptide comprising the amino acid sequence of SEQ ID NO: 11. In some embodiments, the Fab fragment comprises a second polypeptide comprising the amino acid sequence of SEQ ID NO: 12.

Thus, in some embodiments, there is provided a method of treating a cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain (such as scFv) is fused to an N-terminus of the Fab fragment comprising a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the Fab fragment comprises a heavy chain variable region (VH) comprising an amino acid sequence selected from SEQ ID NOs: 7 and 39-43, and/or a light chain variable region (VL) comprising an amino acid sequence selected from SEQ ID NOs: 8 and 44-47. In some embodiments, the Fab fragment comprises a heavy chain polypeptide comprising the amino acid sequence of SEQ ID NO: 11, and/or a light chain polypeptide comprising the amino acid sequence of SEQ ID NO: 12. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of treating a cancer in an individual (such as a human), comprising administering to the individual an effective amount of a multispecific (such as bispecific) Fab fusion protein comprising: (1) a Fab fragment that specifically binds to CD3; wherein the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6; (2) a first binding domain (such as an scFv) that specifically binds to EpCAM; (3) and a second binding domain (such as an scFv) that specifically binds to EpCAM, wherein the first binding domain (such as scFv) is fused to the N-terminus of the VH of the Fab fragment, wherein the second binding domain (such as scFv) is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the Fab fragment comprises a heavy chain variable region (VH) comprising an amino acid sequence selected from SEQ ID NOs: 7 and 39-43, and/or a light chain variable region (VL) comprising an amino acid sequence selected from SEQ ID NOs: 8 and 44-47. In some embodiments, the Fab fragment comprises a heavy chain polypeptide comprising the amino acid sequence of SEQ ID NO: 11, and/or a light chain polypeptide comprising the amino acid sequence of SEQ ID NO: 12. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, the binding domain that specifically binds to EpCAM (also referred herein as EpCAM binding domain) is an antigen-binding fragment of an anti-EpCAM antibody. In some embodiments, the EpCAM binding domain is a single chain antigen-binding fragment of an anti-EpCAM antibody. In some embodiments, the EpCAM binding domain is a scFv. In some embodiments, the scFv comprises an N-VH-VL-C fusion polypeptide. In some embodiments, the EpCAM binding domain is derived from the EpCAM antibody of the present invention, comprising any one, two, or three of the HVRs of the heavy chain variable region comprising the amino acid sequences of SEQ ID NOs: 13-15. In some embodiments, the EpCAM binding domain comprises any one, two, or three of the HVRs of the light chain variable region comprising the amino acid sequences of SEQ ID NOs: 16-18. In some embodiments, the EpCAM binding domain comprises a VH comprising the amino acid sequence of SEQ ID NO: 19. In some embodiments, the EpCAM binding domain comprises a VL comprising the amino acid sequence of SEQ ID NO: 20. In some embodiments, the EpCAM binding domain is an scFv comprising the amino acid sequence of SEQ ID NO: 21. In some embodiments, the method further comprises administering a glucocorticoid (such as dexamethasone) to the individual.

Thus, in some embodiments, there is provided a method of treating a cancer in an individual (such as a human), comprising administering to the individual an effective amount of a multispecific (such as bispecific) Fab fusion protein comprising: (1) a Fab fragment that specifically binds to CD3 (such as the N-terminal 1-27 amino acids of CD3 epsilon); (2) a first scFv that specifically binds to EpCAM; (3) and a second scFv that specifically binds to EpCAM, wherein the first scFv is fused to the N-terminus of the VH of the Fab fragment, wherein the second scFv is fused to the N-terminus of the VL of the Fab fragment, wherein the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18; and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first scFv and the second scFv have the same sequence. In some embodiments, the anti-EpCAM scFv comprises a heavy chain variable region (VH) comprising the amino acid sequence of SEQ ID NO: 19, and/or a light chain variable region (VL) comprising the amino acid sequence of SEQ ID NO: 20. In some embodiments, the anti-EpCAM scFv comprises the amino acid sequence of SEQ ID NO: 21. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of treating a cancer in an individual (such as a human), comprising administering to the individual an effective amount of a multispecific (such as bispecific) Fab fusion protein comprising: (1) a Fab fragment that specifically binds to CD3; wherein the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6; (2) a first scFv that specifically binds to EpCAM; (3) and a second scFv that specifically binds to EpCAM, wherein the first scFv is fused to the N-terminus of the VH of the Fab fragment, wherein the second scFv is fused to the N-terminus of the VL of the Fab fragment, wherein the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18; and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the Fab fragment comprises a heavy chain variable region (VH) comprising an amino acid sequence selected from SEQ ID NOs: 7 and 39-43, and/or a light chain variable region (VL) comprising an amino acid sequence selected from SEQ ID NOs: 8 and 44-47. In some embodiments, the Fab fragment comprises a heavy chain polypeptide comprising the amino acid sequence of SEQ ID NO: 11, and/or a light chain polypeptide comprising the amino acid sequence of SEQ ID NO: 12. In some embodiments, the first scFv and the second scFv have the same sequence. In some embodiments, the anti-EpCAM scFv comprises a heavy chain variable region (VH) comprising the amino acid sequence of SEQ ID NO: 19, and/or a light chain variable region (VL) comprising the amino acid sequence of SEQ ID NO: 20. In some embodiments, the anti-EpCAM scFv comprises the amino acid sequence of SEQ ID NO: 21. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

The EpCAM binding domain may be fused to the N-terminus of the heavy chain polypeptide and/or the N-terminus of the light chain polypeptide of the Fab fragment via a linker, such as a flexible peptide linker, for example, a peptide linker comprising glycines and serines. In some embodiments, the multispecific (such as bispecific) Fab fusion protein comprises a first polypeptide comprising the amino acid sequence of SEQ ID NO: 22. In some embodiments, the multispecific (such as bispecific) Fab fusion protein comprises a second polypeptide comprising the amino acid sequence of SEQ ID NO: 23.

Thus, in some embodiments, there is provided a method of treating a cancer in an individual, comprising administering to the individual an effective amount of a multispecific (such as bispecific) Fab fusion protein comprising a first polypeptide comprising the amino acid sequence of SEQ ID NO: 22 and a second polypeptide comprising the amino acid sequence of SEQ ID NO:23, wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy. In some embodiments, the method further comprises administering a glucocorticoid (such as dexamethasone) to the individual.

The methods described herein are useful for various aspects of cancer treatment. In some embodiments, there is provided a method of inhibiting cell proliferation (such as tumor growth) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, at least about 10% (including for example at least about any of 20%, 30%, 40%, 60%, 70%, 80%, 90%, or 100%) cell proliferation is inhibited. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of inhibiting tumor metastasis in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 μg/kg to about 250 μg/kg (such as about 0.01 jug/kg to about 5 μg/kg, about 0.1 μg/kg to about 30 μg/kg, or about 2.5 μg/kg to about 100 jug/kg). In some embodiments, at least about 10% (including for example at least about any of 20%, 30%, 40%, 60%, 70%, 80%, 90%, or 100%) metastasis is inhibited. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of reducing (such as eradicating) preexisting tumor metastasis (such as metastasis to the lymph node) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 μg/kg to about 250 μg/kg (such as about 0.01 μg/kg to about 5 μg/kg, about 0.1 μg/kg to about 30 μg/kg, or about 2.5 μg/kg to about 100 μg/kg). In some embodiments, at least about 10% (including for example at least about any of 20%, 30%, 40%, 60%, 70%, 80%, 90%, or 100%) metastasis is reduced. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of reducing incidence or burden of preexisting tumor metastasis (such as metastasis to the lymph node) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 μg/kg to about 250 μg/kg (such as about 0.01 μg/kg to about 5 μg/kg, about 0.1 μg/kg to about 30 μg/kg, or about 2.5 μg/kg to about 100 μg/kg). In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of reducing tumor size in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the tumor size is reduced at least about 10% (including for example at least about any of 20%, 30%, 40%, 60%, 70%, 80%, 90%, or 100%). In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of prolonging time to disease progression of cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method prolongs the time to disease progression by at least any of 1, 2, 3, 4, 5, 6, 7, 8, 9, 10, 11, or 12 weeks. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of prolonging survival of an individual having cancer, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method prolongs the survival of the individual by at least any of 1, 2, 3, 4, 5, 6, 7, 8, 9, 10, 11, 12, 18, or 24 month. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of alleviating one or more symptoms in an individual having cancer, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radiofrequency ablation or the like, in an adjuvant setting or a neoadjuvant setting. In some embodiments, the cancer has been refractory to prior therapy.

Examples of cancers that may be treated by the methods of the invention include, but are not limited to, adenocortical carcinoma, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, melanoma, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the method is suitable for treating cancers that overexpress EpCAM on the surface of the cancer cells, such as EpCAM-positive solid cancers. In some embodiments, the cancer cells in the individual express at least about any of more than 2, 5, 10, 20, 50, 100, 200, 500, 1000 or more fold of EpCAM compared to normal cells. In some embodiments, the EpCAM-positive solid cancer is a carcinoma or adenocarcinoma. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

Thus, in some embodiments, there is provided a method of treating an EpCAM-positive solid cancer (such as carcinoma or adenocarcinoma) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating an EpCAM-positive solid cancer (such as carcinoma or adenocarcinoma) in an individual, comprising administering to the individual an effective amount of a multispecific (such as bispecific) Fab fusion protein comprising: (1) a Fab fragment that specifically binds to CD3; (2) a first binding domain (such as an scFv) that specifically binds to EpCAM; (3) and a second binding domain (such as an scFv) that specifically binds to EpCAM, wherein the first scFv is fused to the N-terminus of the VH of the Fab fragment, wherein the second scFv is fused to the N-terminus of the VL of the Fab fragment, and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first binding domain (such as scFv) and the second binding domain (such as scFv) have the same sequence. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating an EpCAM-positive solid cancer (such as carcinoma or adenocarcinoma) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain (such as scFv) is fused to an N-terminus of the Fab fragment comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the Fab fragment comprises a heavy chain variable region (VH) comprising an amino acid sequence selected from SEQ ID NOs: 7 and 39-43, and/or a light chain variable region (VL) comprising an amino acid sequence selected from SEQ ID NOs: 8 and 44-47. In some embodiments, the Fab fragment comprises a heavy chain polypeptide comprising the amino acid sequence of SEQ ID NO: 11, and/or a light chain polypeptide comprising the amino acid sequence of SEQ ID NO: 12. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating an EpCAM-positive solid cancer (such as carcinoma or adenocarcinoma) in an individual (such as a human), comprising administering to the individual an effective amount of a multispecific (such as bispecific) Fab fusion protein comprising: (1) a Fab fragment that specifically binds to CD3 (such as the N-terminal 1-27 amino acids of CD3 epsilon); (2) a first scFv that specifically binds to EpCAM; (3) and a second scFv that specifically binds to EpCAM, wherein the first scFv is fused to the N-terminus of the VH of the Fab fragment, wherein the second scFv is fused to the N-terminus of the VL of the Fab fragment, wherein the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18; and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the first scFv and the second scFv have the same sequence. In some embodiments, the anti-EpCAM scFv comprises a heavy chain variable region (VH) comprising the amino acid sequence of SEQ ID NO: 19, and/or a light chain variable region (VL) comprising the amino acid sequence of SEQ ID NO: 20. In some embodiments, the anti-EpCAM scFv comprises the amino acid sequence of SEQ ID NO: 21. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating an EpCAM-positive solid cancer (such as carcinoma or adenocarcinoma) in an individual (such as a human), comprising administering to the individual an effective amount of a multispecific (such as bispecific) Fab fusion protein comprising: (1) a Fab fragment that specifically binds to CD3; wherein the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6; (2) a first scFv that specifically binds to EpCAM; (3) and a second scFv that specifically binds to EpCAM, wherein the first scFv is fused to the N-terminus of the VH of the Fab fragment, wherein the second scFv is fused to the N-terminus of the VL of the Fab fragment, wherein the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18; and wherein the multispecific (such as bispecific) Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the Fab fragment comprises a heavy chain variable region (VH) comprising an amino acid sequence selected from SEQ ID NOs: 7 and 39-43, and/or a light chain variable region (VL) comprising an amino acid sequence selected from SEQ ID NOs: 8 and 44-47. In some embodiments, the Fab fragment comprises a heavy chain polypeptide comprising the amino acid sequence of SEQ ID NO: 11, and/or a light chain polypeptide comprising the amino acid sequence of SEQ ID NO: 12. In some embodiments, the first scFv and the second scFv have the same sequence. In some embodiments, the anti-EpCAM scFv comprises a heavy chain variable region (VH) comprising the amino acid sequence of SEQ ID NO: 19, and/or a light chain variable region (VL) comprising the amino acid sequence of SEQ ID NO: 20. In some embodiments, the anti-EpCAM scFv comprises the amino acid sequence of SEQ ID NO: 21. In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating an EpCAM-positive solid cancer (such as carcinoma or adenocarcinoma) in an individual, comprising administering to the individual an effective amount of a multispecific (such as bispecific) Fab fusion protein comprising a first polypeptide comprising the amino acid sequence of SEQ ID NO: 22 and a second polypeptide comprising the amino acid sequence of SEQ ID NO:23, wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the EpCAM-positive solid cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, breast cancer, bile duct cancer, and head and neck cancer.

In some embodiments, there is provided a method of treating small intestine cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of treating colorectal cancer (such as colorectal adenocarcinoma) in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the colorectal cancer is adenocarcinoma, gastrointestinal carcinoid tumor, gastrointestinal stromal tumor, leiomysarcoma, melanoma, or squamous cell carcinoma.

In some embodiments, there is provided a method of treating lung cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the lung cancer is a non-small cell lung cancer (NSCLC). Examples of NSCLC include, but are not limited to, large-cell carcinoma, adenocarcinoma, neuroendocrine lung tumors, and squamous cell carcinoma.

In some embodiments, there is provided a method of treating cervical cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual.

In some embodiments, there is provided a method of treating liver cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the liver cancer is liver cell carcinoma, fibrolamellar variants of hepatocellular carcinoma, or mixed hepatocellular cholangiocarcinoma.

In some embodiments, there is provided a method of treating gastric cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the gastric cancer is an adenocarcinoma, lymphoma, gastrointestinal stromal tumor (GIST), carcinoid tumor, squamous cell carcinoma, small cell carcinoma, or leiomyosarcoma.

In some embodiments, there is provided a method of treating pancreatic cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the pancreatic cancer is a serous cystic neoplasm, mucinous cystic neoplasm, intraductal papillary mucinous neoplasm, pancreatic adenocarcinoma, adenosquamous carcinoma, squamous cell carcinoma, signet ring cell carcinoma, undifferentiated carcinoma, undifferentiated carcinoma with giant cells, solid pseudopapillary neoplasm, ampullary cancer, or pancreatic neuroendocrine tumor. In some embodiments, the pancreatic cancer is a pancreatic adenocarcinoma.

In some embodiments, there is provided a method of treating skin cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the skin cancer is melanoma. In some embodiments, the melanoma is superficial spreading melanoma, lentigo maligna melanoma, nodular melanoma, mucosal melanoma, polypoid melanoma, desmoplastic melanoma, amelanotic melanoma, soft-tissue melanoma, or acral lentiginous melanoma.

In some embodiments, there is provided a method of treating renal cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the cancer is renal cell carcinoma. In some embodiments, the renal cell carcinoma is an adenocarcinoma. In some embodiments, the renal cell carcinoma is a clear cell renal cell carcinoma, papillary renal cell carcinoma (also called chromophilic renal cell carcinoma), chromophobe renal cell carcinoma, collecting duct renal cell carcinoma, granular renal cell carcinoma, mixed granular renal cell carcinoma, renal angiomyolipomas, or spindle renal cell carcinoma.

In some embodiments, there is provided a method of treating bladder cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the bladder cancer is a low grade bladder cancer. In some embodiments, the bladder cancer is a high grade bladder cancer. In some embodiments, the bladder cancer is muscle invasive (e.g., T2, T3 or T4). In some embodiments, the bladder cancer is non-invasive (e.g., Ta, T1 Cis, Cis with Ta and/or T1). In some embodiments, the bladder cancer is transitional cell carcinoma or urothelial carcinoma (such as metastatic urothelial carcinoma), including, but not limited to, papillary tumors and flat carcinomas. In some embodiments, the bladder cancer is squamous cell carcinoma, non-squamous cell carcinoma, adenocarcinoma, or small cell carcinoma.

In some embodiments, there is provided a method of treating thyroid cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the thyroid cancer is papillary carcinoma, follicular carcinoma, Hurthle cell carcinoma, medullary thyroid carcinoma, anaplastic carcinoma, thyroid lymphoma, thyroid sarcoma, or parathyroid cancer.

In some embodiments, there is provided a method of treating prostate cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the prostate cancer is an adenocarcinoma. In some embodiments, the prostate cancer is a sarcoma, neuroendocrine tumor, small cell cancer, ductal cancer, or a lymphoma.

In some embodiments, there is provided a method of treating ovarian cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method does not induce cytokine storm. In some embodiments, the ovarian cancer is ovarian epithelial cancer.

In some embodiments, there is provided a method of treating endometrial cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the endometrial cancer is adenocarcinoma, carcinosarcoma, squamous cell carcinoma, undifferentiated carcinoma, small cell carcinoma, or transitional carcinoma.

In some embodiments, there is provided a method of treating breast cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the breast cancer is early stage breast cancer, non-metastatic breast cancer, advanced breast cancer, stage IV breast cancer, locally advanced breast cancer, metastatic breast cancer, breast cancer in remission, breast cancer in an adjuvant setting, or breast cancer in a neoadjuvant setting. In some embodiments, the breast cancer is fibroadenoma, or intraductal papilloma. In some embodiments, the breast cancer is HER2 positive or HER2 negative. In some embodiments, the breast cancer is a triple negative breast cancer.

In some embodiments, there is provided a method of treating bile duct cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the bile duct cancer is an intrahepatic bile duct cancer, a perihilar bile duct cancer, a distal bile duct cancer. In some embodiments, the bile duct cancer is a cholangiocarcinoma, sarcoma, lymphoma, or small cell cancer.

In some embodiments, there is provided a method of treating head and neck cancer in an individual, comprising administering to the individual an effective amount of a multispecific (such as bispecific) Fab fusion protein comprising: a Fab fragment that specifically binds to CD3, and a binding domain (such as scFv) that specifically binds to EpCAM; wherein the binding domain is fused to an N-terminus of the Fab fragment; and wherein the multispecific Fab fusion protein is administered at a dose of about 0.01 µg/kg to about 250 µg/kg (such as about 0.01 µg/kg to about 5 µg/kg, about 0.1 µg/kg to about 30 µg/kg, or about 2.5 µg/kg to about 100 µg/kg). In some embodiments, the method has one or more of the following biological activities: (1) killing cancer cells; (2) inhibits proliferation of cancer cells; and (3) induces redistribution of peripheral T cells. In some embodiments, the multispecific Fab fusion protein comprises a first scFv that specifically binds to EpCAM, and a second scFv that specifically binds to EpCAM; wherein the first binding domain (such as scFv) is fused to the N-terminus of the VH of the Fab fragment; and wherein the second binding domain (such as scFv) is fused to the N-terminus of the VL of the Fab fragment. In some embodiments, the first scFv and the second scFv have the same sequence. In some embodiments, the Fab fragment binds to the N-terminus (such as N-terminal 1-27 amino acids) of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the first scFv and/or the second scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein is administered intravenously. In some embodiments, the multispecific Fab fusion protein is administered at a low frequency. In some embodiments, the method further comprises administering a glucocorticoid (such as dexamethasone) to the individual. In some embodiments, the head and neck cancer is a squamous cell carcinoma in the head and neck. In some embodiments, the head and neck cancer is a hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, or salivary gland cancer.

Exemplary routes of administration of the multispecific Fab fusion protein (MSFP) include, but are not limited to, oral, intravenous, intracavitary, intratumoral, intraarterial, intramuscular, subcutaneous, parenteral, transmucosal, transdermal, ocular, topical, intraperitoneal, intracranial, intrapleural, and epidermal routes, or be delivered into lymph glands, body spaces, organs or tissues known to contain cancer cells. In some embodiments, the MSFP is administered intravenously. In some embodiments, the MSFP is administered by infusion. In some embodiments, the MSFP is administered subcutaneously. In some embodiments, the MSFP is administered by injection.

In some embodiments, the MSFP is administered by intravenous infusion. In some embodiments, the MSFP is infused to the individual over a period of time no more than about any of 24 hours, 20 hours, 15 hours, 10 hours, 8 hours, 6 hours, 3 hours, 2 hours, 1 hours, 30 minutes, or less. In some embodiments, the MSFP is infused to the individual over a period of time of any one of about 30 minutes to about 1 hour, about 1 hour to about 2 hours, about 2 hours to about 4 hours, about 4 hours to about 6 hours, about 6 hours to about 8 hours, about 8 hours to about 10 hours, about 10 hours to about 12 hours, about 12 hours to about 18 hours, about 18 hours to about 24 hours, about 30 minutes to about 2 hours, about 2 hours to about 5 hours, about 5 hours to about 10 hours, about 10 hours to about 20 hours, about 30 minutes to about 10 hours, or about 30 minutes to about 20 hours. The MSFP may be infused to the individual at any suitable rate. In some embodiments, the MSFP may be infused at a rate more than about any of 0.01 µg/kg/hr, 0.02 µg/kg/hr, 0.05 µg/kg/hr, 0.1 µg/kg/hr, 0.2 µg/kg/hr, 0.5 µg/kg/hr, 0.6 µg/kg/hr, 0.7 µg/kg/hr, 0.8 µg/kg/hr, 0.9 µg/kg/hr, 1 µg/kg/hr, 1.5 µg/kg/hr, 2 µg/kg/hr, 3 µg/kg/hr, 4 µg/kg/hr, 5 µg/kg/hr, 10 µg/kg/hr, 15 µg/kg/hr, 20 µg/kg/hr, 25 µg/kg/hr, 50 µg/kg/hr, 75 µg/kg/hr, 100 µg/kg/hr or more.

The dosing regimen of the MSFPs administered to the individual may vary with the particular MSFP composition, the method of administration, and the particular type and stage of cancer being treated. In some embodiments, that effective amount of the MSFP is below the level that induces a toxicological effect (i.e., an effect above a clinically acceptable level of toxicity) or is at a level where a potential side effect can be controlled or tolerated when the composition is administered to the individual.

In some embodiments, the effective amount of the MSFP is below the level that induces an adverse effect in the central nervous system. For example, an adverse effect observed in antibody therapy is the occurrence of infusion-related side effects, such as the cytokine release syndrome ("CRS"), the severe cases of which are known as "cytokine storms". When a "cytokine storm" is induced, the healthy individual's immune system is activated and releases large amounts of the pro-inflammatory cytokines, such as INF-γ, CCL2, IIL-10, IL-6, etc. It is a potentially fatal immune reaction typically consisting of a positive feedback loop between cytokines and immune cells, with highly elevated levels of various cytokines. Other adverse side effects described to be associated with CRS are fatigue, vomiting, tachycardia, hypertension, back pain, but also central nervous system reactions (CNS reactions), such as seizures, encephalopathy, cerebral edema, aseptic meningitis, and headache. In some embodiments, the MSFP is administered at a dose that does not induce cytokine release syndrome, such as cytokine storm. In some embodiments, the MSFP is administered at a dose that does not induce significant release of one or more cytokines selected from the group consisting of IL-2, IL-4, IL-5, IL-6, TNF, and INF-γ. In some embodiments, a significant release of a cytokine is sustained release of a cytokine over the course of at least about any of 1 hour, 2 hours, 4 hours, 6 hours, 8 hours, 10 hours, 12 hours, 18 hours, 24 hours, or more. In some embodiments, a significant release of a cytokine is a serum or blood level of a cytokine at a concentration of at least about any of 1, 5, 10, 20, 50, 100, 200, 500, 1000 or more pg/mL. Without being bound by any theory, the MSFPs described herein require binding to EpCAM on the target tumor cell in order to recruit and activate T cells. Such requirement can greatly reduce unwanted cytokine storms, and unwanted activation of T cells in the absence of the desired target tumor cell.

In some embodiments, the MSFP is administered at a dose of no more than about any one of 0.01 µg/kg, 0.05 µg/kg, 0.1 µg/kg, 0.5 µg/kg, 1 µg/kg, 2 µg/kg, 5 µg/kg, 10 µg/kg, 15 µg/kg, 20 µg/kg, 25 µg/kg, 30 µg/kg, 50 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, 900 µg/kg, or 1 mg/kg. In some embodiments, the dose of the MSFP is within any of the following range, wherein the ranges have an upper limit of any of: 0.05 µg/kg, 0.1 µg/kg, 0.5 µg/kg, 1 µg/kg, 2 µg/kg, 5 µg/kg, 10 µg/kg, 15 µg/kg, 20 µg/kg, 25 µg/kg, 30 µg/kg, 50 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, 900 µg/kg, or 1 mg/kg, and an independently selected lower limit of any of 0.01 µg/kg, 0.05 µg/kg, 0.1 µg/kg, 0.5 µg/kg, 1 µg/kg, 2 µg/kg, 5 µg/kg, 10 µg/kg, 15 µg/kg, 20 µg/kg, 25 µg/kg, 30 µg/kg, 50 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, or 900 µg/kg, and wherein the lower limit is less than the upper limit. In some embodiments, the MSFP is administered at a dose of any one of about 0.01 µg/kg to about 0.05 µg/kg, about 0.05 µg/kg to about 0.1 µg/kg, about 0.1 µg/kg to about 0.5 µg/kg, about 0.5 µg/kg to about 1 µg/kg, about 0.01 µg/kg to about 0.1 µg/kg, about 0.1 µg/kg to about 1 µg/kg, about 1 µg/kg to about 5 µg/kg, about 5 µg/kg to about 10 µg/kg, about 10 µg/kg to about 15 µg/kg, about 15 µg/kg to about 20 µg/kg, about 20 µg/kg to about 25 µg/kg, about 25 µg/kg to about 30 µg/kg, about 5 µg/kg to about 15 µg/kg, about 10 µg/kg to about 30 µg/kg, about 30 µg/kg to about 50 µg/kg, about 50 µg/kg to about 100 µg/kg, about 0.01 µg/kg to about 1 µg/kg, about 0.01 µg/kg to about 5 µg/kg, about 0.01 µg/kg to about 30 µg/kg, about 0.01 µg/kg to about 250 µg/kg, about 0.1 µg/kg to about 10 µg/kg, about 0.1 µg/kg to about 30 µg/kg, about 0.1 µg/kg to about 250 µg/kg, about 1 µg/kg to about 10 µg/kg, about 1 µg/kg to about 20 µg/kg, about 1 µg/kg to about 30 µg/kg, about 1 µg/kg to about 250 µg/kg, about 100 µg/kg to about 250 µg/kg, about 5 µg/kg to about 250 µg/kg, about 250 µg/kg to about 500 µg/kg, about 500 µg/kg to about 1000 µg/kg, or about 0.01 µg/kg to about 1000 µg/kg. The doses described herein may refer to a suitable dose for cynomolgus monkeys, a human equivalent dose thereof, or an equivalent dose for the specific species of the individual. In some embodiments, the MSFP is administered at a dose equivalent to about 0.1 µg/kg to about 100 µg/kg (such as such as about 0.3 µg/kg to about 5 µg/kg, or about 5 µg/kg to about 20 µg/kg) for a cynomolgus monkey. In some embodiments, the MSFP is administered at a dose equivalent to no more than about 30 µg/kg (such as no more than about 20, 15, or 10 µg/kg) for a cynomolgus monkey.

In some embodiments, the MSFP is administered at a dose of about 0.1 µg/kg to about 10 µg/kg, such as about any one of 0.3, 0.5, 0.6, 1, 1.2, 2, 2.4, 3.6, or 4 µg/kg.

The effective amount of the MSFP may be administered in a single dose or in multiple doses. For methods that comprises administration of the MSFP in multiple doses, exemplary dosing frequencies include, but are not limited to, daily, daily without break, weekly, weekly without break, weekly for two out of three weeks, weekly for three out of four weeks, once every three weeks, once every two weeks, monthly, every six months, yearly, etc. In some embodiments, the MSFP is administered about once every 2 weeks, once every 3 weeks, once every 4 weeks, once every 6 weeks, or once every 8 weeks. In some embodiments, the MSFP is administered at least about any of 1×, 2×, 3×, 4×, 5×, 6×, or 7× (i.e., daily) a week. In some embodiments, the intervals between each administration are less than about any of 3 years, 2 years, 12 months, 11 months, 10 months, 9 months, 8 months, 7 months, 6 months, 5 months, 4 months, 3 months, 2 months, 1 month, 4 weeks, 3 weeks, 2 weeks, 1 week, 6 days, 5 days, 4 days, 3 days, 2 days, or 1 day. In some embodiments, the intervals between each administration are more than about any of 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 2 years, or 3 years. In some embodiments, there is no break in the dosing schedule.

In some embodiments, the MSFP is administered at a first dose for a first period of time, and consecutively the MSFP is administered at a second dose for a second period of time, wherein the second dose exceeds the first dose. The first period of time and the second period of time may be of any suitable length, including for example about any one of 1, 2, 3, 4, 5, 6, or more weeks. In some embodiments, the second period of time exceeds the first period of time. N some embodiments, the first period of time is at least about 7 days. In some embodiments, the second period of time is at least about any one of 2 weeks, 3 weeks, 4 weeks, 5 weeks, 6 weeks, or more. The first dose and the second dose can be of any suitable dose as described above. In some embodiments, the first dose is no more than about any one of 2, 1.5, 1, 0.8, 0.7, 0.6, 0.5, 0.4, 0.3, 0.2, 0.1 µg/kg or less. In some embodiments, the second dose is about 0.1 µg/kg to about 10 µg/kg, such as about 0.3 µg/kg to about 5 µg/kg. In some embodiments, the second dose is about any one of 0.3, 0.6, 1.2, 2.4, or 3.6 µg/kg.

In some embodiments, the MSFP is administered at a low frequency, for example, any one of no more frequent than once per month, once per 2 months, once per 3 months, once per 4 months, once per 5 months, once per 6 months, once per 7 months, once per 8 months, once per 9 months, once per 10 months, once per 11 months, once per year, once per 18 months, once per two years, once per three years, or less. In some embodiments, the MSFP is administered in a single dose. In some embodiments, the MSFP is administered twice weekly.

The administration of the MSFP can be extended over an extended period of time, such as from 1 day to about a week, from about a week to about a month, from about a month to about a year, from about a year to about several years. In some embodiments, the MSFP is administered over a period of at least any of about 1 day, 2 days, 3 days, 4 days, 5 days, 6 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 1 year, 2 years, 3 years, 4 years, or more.

In some embodiments, the method further comprises administration of one or more glucocorticoids. Glucocorticoids (GC) are a class of steroid hormones that bind to the glucocorticoid receptor (GR), which is present in almost every vertebrate animal cell, including humans. These compounds are potent anti-inflammatory agents, regardless of the inflammation's cause. In some embodiments, the glucocorticoid suppresses release of one or more cytokines selected from the group consisting of IL-1, IL-2, IL-3, IL-4, IL-5, IL-6, IL-8 and IFN-γ. Suitable glucocorticoids include, but are not limited to, cortisone, hydrocortisone, cortisol, cloprednol, prednisone, prednisolone, methylprednisolone, deflazacort, fludrocortisone, triamcinolone, dexamethasone, and betamethasone. In some embodiments, the glucocorticoid is selected from the group consisting of cortisone, hydrocortisone, cortisol, cloprednol, prednisone, prednisolone, methylprednisolone, deflazacort, fludrocortisone, triamcinolone, dexamethasone, betamethasone and a pharmaceutically acceptable ester, salt, or complex of thereof. In some embodiments, the glucocorticoid is dexamethasone. In some embodiments, the glucocorticoid is a pharmaceutically acceptable ester, salt, or complex of dexamethasone.

The glucocorticoid may be administered to the individual simultaneously with the MSFP or prior to the administration of the MSFP. The glucocorticoid may be administered at a time no longer than about any one of 3 hours, 2 hours, 1 hours, 30 minutes, or less from the administration of the MSFP. In some embodiments, the glucocorticoid is administered simultaneously or prior to each dose of the MSFP. In some embodiments, the glucocorticoid is administered simultaneously or prior to the first dose of the MSFP. In some embodiments, wherein the MSFP is administered at a first dose for a first period of time, and consecutively the MSFP is administered at a second dose for a second period of time, the glucocorticoid is administered prior (such as about 1 hour prior) to the first administration of the MSFP for the first period of time, and the glucocorticoid is administered prior (such as about 1 hour prior) to the first administration of the MSFP for the second period of time. In some embodiments, the glucocorticoid is administered prior to the administration of the MSFP when the individual has an elevated liver enzyme level (such as ALT, TBil, and/or ALP) and/or an elevated cytokine level (such as IL-6). The glucocorticoid may be administered at any suitable dosage, including, for example, at least about any one of 0.1, 0.5, 1, 2, 3, 4, 5 mg/kg or more. In some embodiments, the glucocorticoid is administered at a dose of at least about any one of 1, 2, 5, 10, 15, 20, 25 mg or more.

In some embodiments, the glucocorticoid is dexamethasone. In some embodiments, the method comprises administering dexamethasone to the individual prior to the administration of the first dose of the MSFP. In some embodiments, the dexamethasone is administered at a dose of about 0.1 mg/kg to about 5 mg/kg.

Multispecific Fab Fusion Proteins

The multispecific Fab fusion proteins (MSFP) used in the methods described herein comprise an anti-CD3 Fab fragment fused to a first EpCAM binding domain at the N-terminal end of the VH of the Fab fragment and/or a second EpCAM binding domain at the N-terminal end of the VL of the Fab fragment. In some embodiments, the EpCAM binding domain is an anti-EpCAM scFv. In some embodiments, the EpCAM binding domain is connected to the VH or VL of the anti-CD3 Fab fragment via a linker. An exemplary bispecific Fab fusion protein useful for methods of the present invention is shown in FIG. 1.

Fab Fragment

The Fab fragment of the MSFPs described herein specifically binds to CD3, such as human CD3. "CD3" is known in the art as a multi-protein complex of six chains (see, Abbas and Lichtman, 2003; Janeway et al., p 172 and 178, 1999). In mammals, the complex comprises a CD3 gamma chain, a CD3 delta chain, two CD3 epsilon chains, and a homodimer of CD3 zeta chains. The CD3 gamma, CD3 delta, and CD3 epsilon chains are highly related cell surface proteins of the immunoglobulin superfamily containing a single immunoglobulin domain. The transmembrane regions of the CD3 gamma, CD3 delta, and CD3 epsilon chains are negatively charged, which is a characteristic that allows these chains to associate with the positively charged T cell receptor chains. The intracellular tails of the CD3 gamma, CD3 delta, and CD3 epsilon chains each contain a single conserved motif known as an immunoreceptor tyrosine-based activation motif or ITAM, whereas each CD3 zeta chain has three. Without being bound by theory, it is believed the ITAMs are important for the signaling capacity of a TCR complex. CD3 as used herein may be from various animal species, including human, primate, mouse, rat, or other mammals.

In some embodiments, the Fab fragment of the MSFP specifically binds to an individual CD3 chain, such as CD3 gamma chain, CD3 delta chain, or CD3 epsilon chain. In some embodiments, the Fab fragment specifically binds to a complex formed from two or more individual CD3 chains (e.g., a complex of more than one CD3 epsilon chains, a complex of a CD3 gamma and CD3 epsilon chain, a complex of a CD3 delta and CD3 epsilon chain). In some embodiments, the Fab fragment specifically binds to a CD3 epsilon chain. In some embodiments, the Fab fragment specifically binds to the N-terminus of CD3 epsilon. In some embodiments, the Fab fragment specifically binds to amino acids 1-27 of CD3 epsilon.

The Fab fragments can be generated by a variety of methods known in the art (see, e.g., U.S. Pat. Nos. 6,291,161; 6,291,158). Sources of Fabs include monoclonal antibody or antigen-binding fragments thereof from various species, including human, camelid (from camels, dromedaries, or llamas; Hamers-Casterman et al. (1993) Nature, 363:446 and Nguyen et al. (1998) J. Mol. Biol., 275:413), shark (Roux et al. (1998) Proc. Nat'l. Acad. Sci. (USA) 95:11804), fish (Nguyen et al. (2002) Immunogenetics, 54:39), rodent, avian, or ovine. In some embodiments, the Fab fragment is derived from a human or humanized antibody.

In some embodiments, the Fab fragment specifically binds to both human and non-human primates (such as cynomolgus monkey) CD3. Exemplary anti-human CD3 antibody with cross reactivity to monkey CD3 include, but are not limited to, SP34 mouse monoclonal antibody, (see, for example, Pressano, S. The EMBO J. 4:337-344, 1985; Alarcon, B. EMBO J. 10:903-912, 1991; Salmeron A. et al., J. Immunol. 147:3047-52, 1991; Yoshino N. et al., Exp. Anim 49:97-110, 2000; Conrad M L. et al., Cytometry 71A:925-33, 2007; and Yang et al., J. Immunol. 137:1097-1100: 1986). MSFPS having anti-CD3 Fab fragments with cross-reactivity to monkey CD3 may facilitate toxicity studies in non-human primates, which can provide more relevant safety assessments for human clinical trial candidates, without having to perform toxicity studies in chimpanzees or using surrogate molecules.

In some embodiments, the Fab fragment is derived from an anti-CD3 antibody that does not have cross-reactivity to non-human primates. Exemplary anti-CD3 antibodies include the Cris-7 monoclonal antibody (Reinherz, E. L. et al. (eds.), Leukocyte typing II, Springer Verlag, New York, (1986)), BC3 monoclonal antibody (Anasetti et al. (1990) J. Exp. Med. 172:1691), OKT3 (Ortho multicenter Transplant Study Group (1985) N. Engl. J. Med. 313:337) and derivatives thereof such as OKT3 ala-ala (Herold et al. (2003) J. Clin. Invest. 11:409), visilizumab (Carpenter et al. (2002) Blood 99:2712), and 145-2C11 monoclonal antibody (Hirsch et al. (1988) J. Immunol. 140: 3766). Further CD3 binding molecules contemplated herein include UCHT-1 (Beverley, P C and Callard, R. E. (1981) Eur. J. Immunol. 11: 329-334) and CD3 binding molecules described in WO2004/106380; WO2010/037838; WO2008/119567; WO2007/042261; WO2010/150918.

In some embodiments, the Fab fragment comprises one constant and one variable region of an immunoglobulin heavy, and one constant and one variable region of an immunoglobulin light chain. In some embodiments, the heavy chain constant and variable regions heterodimerize with the light chain variable and constant regions, and are covalently linked by a disulfide bond between the heavy and light chain constant regions. In some embodiments, the Fab fragment has the basic structure $NH_2$-VL-CL-S—S-CH1-VH—$NH_2$. In some embodiments, the CH1 and the CL of the Fab fragment are connected by one or more disulfide bonds. In some embodiments, the number of disulfide bonds between the first constant region of heavy chain (CH1) and the light constant (CL) of the Fab is at least one, such as 2, 3, 4, or more. In some embodiments, cysteine residues are engineered in the Fab fragment (such as in the CH1 and CL regions) to introduce disulfide bonds.

In some embodiments, the Fab fragment of the MSFP does not comprise a disulfide bond. For example, the heavy and light chains may be engineered in such a way so as to stably interact without the need for disulfide bonds. In some embodiments, the heavy chain or light chain can be engineered to remove a cysteine residue, and wherein the heavy and light chains still stably interact and function as a Fab. In some embodiments, mutations are made to facilitate stable interactions between the heavy and light chains. For example, a "knobs into holes" engineering strategy can be used to facilitate dimerization between the heavy and light chains of a Fab (see e.g., 1996 Protein Engineering, 9:617-621). Also contemplated for use herein are variant Fab fragments designed for a particular purpose, for example, amino acid changes in the constant domains of CH1 and/or CL, and removal of a disulfide bond or addition of tags for purification, etc.

In some embodiments, the configuration of the variable and constant regions within the Fab fragment may be different from what is found in a native Fab. In some embodiments, the orientation of the variable and constant regions may be VH-CL in one chain, and VL-CH1 in another chain (see, for example, Shaefer et al. (2011), PNAS, 108:111870-92).

In some embodiments, the Fab fragments of the MSFP are derived from monoclonal antibodies. Suitable monoclonal antibodies may be of any type, including IgA, IgM, IgD, IgG, IgE and subtypes thereof, such as IgG1, IgG2, IgG3, and IgG4. The light chain domains may be derived from the kappa or lambda chain. In some embodiments, the Fab fragment is designed recombinantly.

In some embodiments, the Fab fragment comprises a human immunoglobulin CH1. In some embodiments, the human immunoglobulin CH1 comprises the amino acid sequence of SEQ ID NO: 9. In some embodiment, the Fab fragment comprises a human lambda light chain constant region. In one embodiment, the human lambda light chain constant region comprises the amino acid sequence of SEQ ID NO:10.

(human CH1)
SEQ ID NO: 9
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KS (human lambda CL)
SEQ ID NO: 10
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTE

The Fab fragment of the MSFP specifically binds to CD3 via an antigen-binding site formed between the heavy chain variable region and the light chain variable region (VH and VL). The antigen-binding site comprises at least one (such as 1, 2, or 3) HVR of an immunoglobulin heavy chain and/or at least one (such as 1, 2, or 3) HVR of an immunoglobulin light chain. In some embodiments, the MSFP comprises 1, 2, 3, 4, 5, or all 6 HVRs of a VH and VL sequence of a full-length antibody that specifically binds to CD3.

In some embodiments, the Fab fragment is derived from SP34. In some embodiments, the Fab fragment is a CD3 Fab fragment described in U.S. Pat. No. 8,846,042. In some embodiments, the Fab fragment comprises a heavy chain variable region (VH) comprising one, two or three HVRs (or CDRs) from SEQ ID NO: 7, and/or a light chain variable region (VL) comprising one, two or three HVRs (or CDRs) from SEQ ID NO: 8. In some embodiments, the Fab fragment comprises a heavy chain variable region (VH) comprising three HVRs from SEQ ID NO: 7, and/or a light chain variable region (VL) comprising three HVRs from SEQ ID NO: 8. In some embodiments, the Fab fragment comprises a heavy chain variable region (VH) comprising one, two or three HVRs selected from SED ID Nos: 1-3, and/or a light chain variable region (VL) comprising one, two or three HVRs selected from SED ID NOs: 4-6. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the Fab fragment comprises a heavy chain variable region (VH) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to a sequence selected from the group consisting of SEQ ID NOs:7 and 39-43. In some embodiments, the Fab fragment comprises a light chain variable region (VL) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to a sequence selected from the group consisting of SEQ ID NO: 8 and 44-47. In some embodiments, a $V_H$ or VL sequence having at least 90%, 91%, 92%, 93%, 94%, 95%, 96%, 97%, 98%, or 99% identity contains substitutions (e.g., conservative substitutions), insertions, or deletions relative to the reference sequence, but the Fab fragment comprising that sequence retains the ability to bind to CD3. In some embodiments, one or two amino acids have been substituted, inserted and/or deleted in any one or more of the HVRs. In some embodiments, substitutions, insertions, or deletions occur in regions outside the HVRs (i.e., in the FRs). In some embodiments, the Fab fragment comprises a heavy chain variable region (VH) comprising an amino acid sequence selected from SEQ ID NOs: 7 and 39-43. In some embodiments, the Fab fragment comprises a light chain variable region (VL) comprising an amino acid sequence selected from SEQ ID NOs: 8 and 44-47. In some embodiments, the Fab fragment comprises a heavy chain variable region (VH) comprising the amino acid sequence of SEQ ID NO: 7, and/or a light chain variable region (VL) comprising the amino acid sequence of SEQ ID NO: 8. In some embodiments, the Fab fragment comprises a heavy chain polypeptide comprising the amino acid sequence of SEQ ID NO: 11, and/or a light chain polypeptide comprising the amino acid sequence of SEQ ID NO: 12.

(CD3 HVR-H1)
SEQ ID NO: 1
TYAMN (CD3 HVR-H2)
SEQ ID NO: 2
RIRSKYNNYATYYADSVKD (CD3 HVR-H3)
SEQ ID NO: 3
HGNFGNSYVSWFAY (CD3 HVR-L1)
SEQ ID NO: 4
RSSTGAVTTSNYAN (CD3 HVR-L2)
SEQ ID NO: 5
GTNKRAP (CD3 HVR-L3)
SEQ ID NO: 6
ALWYSNLWV (CD3 VH)
SEQ ID NO: 7
EVQLVESGGGLVQPGGSLRLSCAASGFTFN<u>TYAMN</u>WVRQAPGKGLEWVA<u>R</u>

<u>IRSKYNNYATYYADSVKD</u>RFTISRDDSKNTLYLQMNSLRAEDTAVYYCVR

<u>HGNFGNSYVSWFAY</u>WGQGTMVTVSS (CD3 VL)
SEQ ID NO: 8
QAVVTQEPSLTVSPGGTVTLTC<u>RSSTGAVTTSNYAN</u>WVQQKPGQAPRGLI

GG<u>TNKRAP</u>GTPARFSGSLLGGKAALTLSGVQPEDEAEYYC<u>ALWYSNLWV</u>F

GGGTKLTVL (CD3 Heavy chain)
SEQ ID NO: 11
EVQLVESGGGLVQPGGSLRLSCAASGFTFN<u>TYAMN</u>WVRQAPGKGLEWVA<u>R</u>

<u>IRSKYNNYATYYADSVKD</u>RFTISRDDSKNTLYLQMNSLRAEDTAVYYCVR

-continued

HGNFGNSYVSWFAYWGQGTMVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKS (CD3 Light chain)

SEQ ID NO: 12

QAVVTQEPSLTVSPGGTVTLTCRSSTGAVTTSNYANWVQQKPGQAPRGLI

GGTNKRAPGTPARFSGSLLGGKAALTLSGVQPEDEAEYYCALWYSNLWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTE (CD3 VH)

SEQ ID NO: 39

EVQLVESGGGLVQPGGSLRLSCAASGFTFSTYAMNWVRQAPGKGLEWVSR

IRSKYNNYATYYADSVKDRFTISRDDSKNTLYLQMNSLRAEDTAVYYCAR

HGNFGNSYVSWFAYWGQGTMVTVSS (CD3 VH)

SEQ ID NO: 40

EVQLVESGGGLVQPGGSLRLSCAASGFTFNTYAMNWVRQAPGKGLEWVSR

IRSKYNNYATYYADSVKDRFTISRDDSKNTLYLQMNSLRAEDTAVYYCAR

HGNFGNSYVSWFAYWGQGTMVTVSS (CD3 VH)

SEQ ID NO: 41

EVQLVESGGGLVQPGGSLRLSCAASGFTFSTYAMNWVRQAPGKGLEWVAR

IRSKYNNYATYYADSVKDRFTISRDDSKNTLYLQMNSLRAEDTAVYYCAR

HGNFGNSYVSWFAYWGQGTMVTVSS (CD3 VH)

SEQ ID NO: 42

EVQLVESGGGLVQPGGSLRLSCAASGFTFSTYAMNWVRQAPGKGLEWVAR

IRSKYNNYATYYADSVKDRFTISRDDSKNTLYLQMNSLRAEDTAVYYCVR

HGNFGNSYVSWFAYWGQGTMVTVSS (CD3 VH)

SEQ ID NO: 43

EVQLVESGGGLVQPGGSLKLSCAASGFTFSTYAMNWVRQASGKGLEWVGR

IRSKYNNYATYYADSVKDRFTISRDDSKNTAYLQMNSLKTEDTAVYYCTR

HGNFGNSYVSWFAYWGQGTLVTVSS (CD3 VL)

SEQ ID NO: 44

QAVVTQEPSLTVSPGGTVTLTCRSSTGAVTTSNYANWFQQKPGQAPRGLI

GGTNKRAPGTPARFSGSLLGGKAALTLSGVQPEDEAEYYCALWYSNLWVF

GGGTKLTVL (CD3 VL)

SEQ ID NO: 45

QAVVTQEPSLTVSPGGTVTLTCRSSTGAVTTSNYANWVQQKPGQAPRGLI

GGTNKRAPWTPARFSGSLLGGKAALTLSGVQPEDEAEYYCALWYSNLWVF

GGGTKLTVL (CD3 VL)

SEQ ID NO: 46

QAVVTQEPSLTVSPGGTVTLTCRSSTGAVTTSNYANWFQQKPGQAPRGLI

GGTNKRAPWTPARFSGSLLGGKAALTLSGVQPEDEAEYYCALWYSNLWVF

GGGTKLTVL

-continued (CD3 VL)

SEQ ID NO: 47

QAVVTQEPSLTVSPGGTVTLTCRSSTGAVTTSNYANWYQQKPGQAPRGLI

GGTNKRAPWTPARFSGSLLGGKAALTLSGVQPEDEAEYYCALWYSNLWVF

GGGTKLTVL

In some embodiments, a specific VH and/or VL of an anti-CD3 Fab fragment may be used to screen a library of the complementary variable region to identify VH/VL with desirable properties, such as increased affinity for CD3. Such methods are described, for example, in Portolano et al., J. Immunol. (1993) 150:880-887; Clarkson et al., Nature (1991) 352:624-628; and Klimka et al., British Journal of Cancer (2000) 83:252-260; Beiboer et al., J. Mol. Biol. (2000) 296:833-849; and Rader et al., PNAS (1998) 95:8910-8915.

EpCAM Binding Domain

The MSFPs described herein comprises one or two binding domains that specifically bind to EpCAM. Epithelial cell adhesion molecule (EpCAM, CD326), also known as 17-1A, ESA, AUA1, EGP40, etc., is a 40 kD transmembrane glycoprotein composed of 314 amino acid. EpCAM is involved in cell signaling, migration, proliferation, and differentiation. EpCAM is specifically expressed in various types of epithelial cells and main types of human malignancies. For example, EpCAM is highly expressed in colon cancer, lung cancer, prostate cancer, liver cancer, pancreatic cancer, breast cancer and ovarian cancer, thus can be used as diagnostic marker for various cancers. EpCAM is also a potential target for immunotherapeutic strategies, including vaccines, murinized or humanized monoclonal antibodies, and antibodies conjugated with bacterial toxins or chemotherapy drugs, such as EpCAM specific antibodies ING-1, adecatumumab, edrecolomab, etc.

The binding domains, including the EpCAM binding domains, in the MSFP not only provide additional binding specificities and enhanced properties (e.g., increased serum half-life, or activation of immune activation cascades), but also create steric hindrance to significantly reduce the binding affinity of the Fab fragment to CD3 due to fusion to the N terminus of the VH and/or VL chains. This is in direct contrast to other Fab fusion proteins, such as TRIBODIES™, which fuses additional binding domains at the C terminus of the Fab fragment (see, e.g., Journal of Immunology, 2000, 165: 7050-7057). The binding domains are not intended to dimerize, unlike other known fusion proteins, such as those described in WO2008/024188 and WO2009/149185. A further distinguishing characteristic of the MSFP is that the binding domains reduce the binding affinity of the Fab to CD3 when the MSFP is not bound to cell surface targets, such as EpCAM, on tumor cells.

In some embodiments, the MSFP has a prolonged in vivo half-life compared to the anti-CD3 Fab alone. In some embodiments, the half-life of the MSFP is at least about any of 1.5, 2, 3, 4, 5, 6, 7, 8, 9, 10, or more times the half-life of the anti-CD3 Fab fragment alone.

The binding domains, including EpCAM, may be selected from antigen-binding domains, such as scFv or scTCR, extracellular domains of receptors, ligands for cell surface molecules/receptors, or receptor binding domains thereof, and tumor binding proteins. In some embodiments, the antigen binding domain is selected from an scFv, a VH, a VL, a domain antibody variant (dAb), a camelid antibody (VHH), a fibronectin 3 domain variant, an ankyrin repeat variant, and other antigen-specific binding domains derived from other protein scaffolds.

In some embodiments, the EpCAM binding domain is an scFv that specifically binds to EpCAM (also referred herein as anti-EpCAM scFv). In some embodiments, the VH and VL of the anti-EpCAM scFv are connected to each other via a peptide linker, such as a flexible linker comprising glycines and/or serines. In some embodiments, the VH and VL of the anti-EpCAM scFv are connected to each other directly. In some embodiments, the anti-EpCAM scFv comprises an N-VH-VL-C fusion polypeptide. In some embodiments, the anti-EpCAM scFv comprises an N-VL-VH—C fusion polypeptide.

The EpCAM binding domain (such as scFv) may be derived from any suitable anti-EpCAM antibody. In some embodiments, the anti-EpCAM antibody is a human, humanized, or chimeric antibody. In some embodiments, the EpCAM binding domain specifically binds to both human and non-human primates (such as cynomolgus monkey). In some embodiments, the EpCAM binding domain specifically recognizes human EpCAM, but does not have cross-reactivity to non-human primates. Exemplary anti-EpCAM antibodies are known in the art, for example, see, U.S. Pat. No. 8,884,602. The anti-EpCAM binding domain may comprise at least one (such as 1, 2, or 3) HVR of an immunoglobulin heavy chain and/or at least one (such as 1, 2, or 3) HVR of an immunoglobulin light chain. In some embodiments, the anti-EpCAM binding domain comprises 1, 2, 3, 4, 5, or all 6 HVRs of a VH and VL sequence of a full-length antibody that specifically binds to EpCAM.

In some embodiments, the anti-EpCAM scFv comprises a heavy chain variable region (VH) comprising one, two or three HVRs (or CDRs) from SEQ ID NO: 19, and/or a light chain variable region (VL) comprising one, two or three HVRs (or CDRs) from SEQ ID NO: 20. In some embodiments, the anti-EpCAM scFv comprises a heavy chain variable region (VH) comprising three HVRs from SEQ ID NO: 19, and/or a light chain variable region (VL) comprising three HVRs from SEQ ID NO: 20. In some embodiments, the anti-EpCAM scFv comprises a heavy chain variable region (VH) comprising one, two or three HVRs selected from SED ID Nos: 13-15, and/or a light chain variable region (VL) comprising one, two or three HVRs selected from SED ID Nos: 16-18. In some embodiments, the anti-EpCAM scFv comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the anti-EpCAM scFv comprises a heavy chain variable region (VH) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:19, and/or a light chain variable region (VL) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:20. In some embodiments, the anti-EpCAM scFv comprises a heavy chain variable region (VH) comprising the amino acid sequence of SEQ ID NO: 19, and/or a light chain variable region (VL) comprising the amino acid sequence of SEQ ID NO: 20. In some embodiments, the anti-EpCAM scFv comprises the amino acid sequence of SEQ ID NO:21.

```
(EpCAM HVR-H1)
                                            SEQ ID NO: 13
NYWMS (EpCAM HVR-H2)
                                            SEQ ID NO: 14
NIKQDGSEKFYADSVKG (EpCAM HVR-H3)
                                            SEQ ID NO: 15
VGPSWEQDY (EpCAM HVR-L1)
                                            SEQ ID NO: 16
TGSSSNIGSYYGVH (EpCAM HVR-L2)
                                            SEQ ID NO: 17
SDTNRPS (EpCAM HVR-L3)
                                            SEQ ID NO: 18
QSYDKGFGHRV (EpCAM VH)
                                            SEQ ID NO: 19
EVQLVESGGGLVQPGGSLRLSCAASGFTFSNYWMSWVRQAPGKGLEWVAN

IKQDGSEKFYADSVKGRFTISRDNAKNSLYLQMNSLRAEDTAVYYCARVG

PSWEQDYWGQGTLVTVSA (EpCAM VL)
                                            SEQ ID NO: 20
GAQSVLTQPPSVSGAPGQRVTISCTGSSSNIGSYYGVHWYQQLPGTAPKL

LIYSDTNRPSGVPDRFSGSKSGTSASLAITGLQAEDEADYYCQSYDKGFG

HRVFGGGTKLTVL (EpCAM scFv)
                                            SEQ ID NO: 21
EVQLVESGGGLVQPGGSLRLSCAASGFTFSNYWMSWVRQAPGKGLEWVAN

IKQDGSEKFYADSVKGRFTISRDNAKNSLYLQMNSLRAEDTAVYYCARVG

PSWEQDYWGQGTLVTVSAGGGGSGGGGSGGGGSGAQSVLTQPPSVSGAPG

QRVTISCTGSSSNIGSYYGVHWYQQLPGTAPKLLIYSDTNRPSGVPDRFS

GSKSGTSASLAITGLQAEDEADYYCQSYDKGFGHRVFGGGTKLTVL
```

Linkers

The MSFPs described herein may comprise a linker (such as a peptide linker) situated between the VH or the VL of the Fab fragment and the binding domains. In some embodiments, the linker between the VH of the Fab fragment and the first binding domain is the same as the linker between the VL of the Fab fragment and the first binding domain. In some embodiments, the linker between the VH of the Fab fragment and the first binding domain is different from the linker between the VL of the Fab fragment and the first binding domain. In some embodiments, the anti-EpCAM scFv comprises a linker (such as peptide linker) situated between the VH and VL of the scFv, which may be the same or different from any of the linkers between the VH and VL of the Fab fragment and the binding domains.

The linkers can be peptide linkers of any length. In some embodiments, the peptide linker is from 1 amino acids to 10 amino acids long, from 2 amino acids to 15 amino acids long, from 3 amino acids to 12 amino acids long, from 4 amino acids to 10 amino acids long, from 5 amino acids to 9 amino acids long, from 6 amino acids to 8 amino acids long, or from 1 amino acids to 20 amino acids long. In some embodiments, the peptide linker is any of 1, 2, 3, 4, 5, 6, 7, 8, 9, 10, 11, 12, 13, 14, 15, 16, 17, 18, 19 or 20 amino acids long. In some embodiments, the peptide linker is any of 21, 22, 23, 24, 25, 26, 27, 28, 29 or 30 amino acids long. In some embodiments, the N-terminus of the peptide linker is covalently linked to the C-terminal of the binding domain, and the C terminus of the peptide linker is covalently linked to the N-terminus of the VH or VL of the Fab fragment.

In some embodiments, the linker is a flexible linker. Exemplary flexible linkers include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). Exemplary flexible linkers include, but are not limited to Gly-Gly, Gly-Gly-Ser-Gly (SEQ ID NO: 24), Gly-Gly-Ser-Gly-Gly (SEQ ID NO: 25), Gly-Ser-Gly-Ser-Gly (SEQ ID NO: 26), Gly-Ser-Gly-Gly-Gly (SEQ ID NO: 27), Gly-Gly-Gly-Ser-Gly (SEQ ID NO: 28), Gly-Ser-Ser-Ser-Gly (SEQ ID NO: 29), and the like. In some embodiments, the linker between the VH of the anti-CD3 Fab fragment and the EpCAM binding domain (such as scFv) is Gly-Gly. In some embodiments, the linker between the VL of the anti-CD3 Fab fragment and the EpCAM binding domain (such as scFv) is Gly-Gly. The ordinarily skilled artisan will recognize that design of an MSFP can include linkers that are all or partially flexible, such that the linker can include a flexible linker portion as well as one or more portions that confer less flexible structure to provide a desired MSFP structure.

In some embodiments, the linker between the Fab and the binding domains is a stable linker (not cleavable by protease, especially MMPs).

In some embodiments, the linker is a cleavable linker. In some embodiments, the linker between the Fab VH or VL and the binding domain comprises a protease substrate cleavage sequence, for example, an MMP substrate cleavage sequence. A well-known peptide sequence of PLGLAG (SEQ ID NO: 30) in a substrate can be cleaved by most MMPs. Substrate sequences that can be cleaved by MMPs have been extensively studied. For example, the sequence of PLGLAG (SEQ ID NO: 30) can be cleaved by most MMPs. In some embodiments, the protease cleavage site is recognized by MMP-2, MMP-9 or a combination thereof.

In some embodiments, the MSFP comprises a first polypeptide comprising the amino acid sequence of SEQ ID NO: 22. In some embodiments, the MSFP comprises a second polypeptide comprising the amino acid sequence of SEQ ID NO:23. In some embodiments, the MSFP comprises a first polypeptide comprising the amino acid sequence of SEQ ID NO: 22, and a second polypeptide comprising the amino acid sequence of SEQ ID NO: 23. Further provided are MSFPs and compositions (such as pharmaceutical compositions) thereof comprising a first polypeptide comprising the amino acid sequence of SEQ ID NO: 22, and a second polypeptide comprising the amino acid sequence of SEQ ID NO: 23.

```
                                          SEQ ID NO: 22
EVQLVESGGGLVQPGGSLRLSCAASGFTFSNYWMSWVRQAPGKGLEWVAN

IKQDGSEKFYADSVKGRFTISRDNAKNSLYLQMNSLRAEDTAVYYCARVG

PSWEQDYWGQGTLVTVSAGGGGSGGGGSGGGGSGAQSVLTQPPSVSGAPG

QRVTISCTGSSSNIGSYYGVHWYQQLPGTAPKLLIYSDTNRPSGVPDRFS

GSKSGTSASLAITGLQAEDEADYYCQSYDKGFGHRVFGGGTKLTVLGGEV

QLVESGGGLVQPGGSLRLSCAASGFTFNTYAMNWVRQAPGKGLEWVARIR

SKYNNYATYYADSVKDRFTISRDDSKNTLYLQMNSLRAEDTAVYYCVRHG

NFGNSYVSWFAYWGQGTMVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCPPCS

SEQ ID NO: 23
EVQLVESGGGLVQPGGSLRLSCAASGFTFSNYWMSWVRQAPGKGLEWVAN

IKQDGSEKFYADSVKGRFTISRDNAKNSLYLQMNSLRAEDTAVYYCARVG

PSWEQDYWGQGTLVTVSAGGGGSGGGGSGGGGSGAQSVLTQPPSVSGAPG

QRVTISCTGSSSNIGSYYGVHWYQQLPGTAPKLLIYSDTNRPSGVPDRFS

GSKSGTSASLAITGLQAEDEADYYCQSYDKGFGHRVFGGGTKLTVLGGQA

VVTQEPSLTVSPGGTVTLTCRSSTGAVTTSNYANWVQQKPGQAPRGLIGG

TNKRAPGTPARFSGSLLGGKAALTLSGVQPEDEAEYYCALWYSNLWVFGG

GTKLTVLGQPKAAPSVTLFPPSSEELQANKATLVCLISDFYPGAVTVAWK

ADSSPVKAGVETTTPSKQSNNKYAASSYLSLTPEQWKSHRSYSCQVTHEG

STVEKTVAPTECPPCS
```

III. EpCAM Antibodies

Further provided by the present application are novel anti-EpCAM antibodies or antigen-binding fragments thereof, including multispecific (such as bispecific) Fab fusion proteins comprising an antigen-binding fragment derived from the anti-EpCAM antibody. Compared to anti-EpCAM antibodies and fragments known in the art, the anti-EpCAM antibodies and antigen-binding fragments thereof described herein have enhanced stability and ability to be expressed. Additionally, the anti-EpCAM antibodies and antigen-binding fragments thereof of the present invention have cross-reactivity towards EpCAM from both human and non-human primates (such as cynomolgus monkeys), which is beneficial for extrapolating results from toxicity and efficacy studies in monkeys to human clinical studies for evaluating the EpCAM antibodies or derivatives thereof (such as MSFPs).

The antibodies of the present invention bind to an EpCAM epitope with an equilibrium binding constant ($K_d$) of ≤1 μM, e.g., ≤100 nM, preferably ≤10 nM, and more preferably ≤1 nM. For example, the anti-EpCAM antibodies provided herein exhibit a $K_d$ in the range approximately between 1 nM to about 1 pM.

The anti-EpCAM antibodies of the invention serve to completely or partially modulate, block, inhibit, reduce, antagonize, neutralize or otherwise interfere with the functional activity of the widely distributed EpCAM. The EpCAM antibodies are considered to completely modulate, block, inhibit, reduce, antagonize, neutralize or otherwise interfere with EpCAM functional activity when the level of EpCAM functional activity in the presence of EpCAM antibody is decreased by at least 95%, e.g., by 96%, 97%, 98%, 99% or 100% as compared to the level of EpCAM functional activity in the absence of binding with an anti-EpCAM antibody described herein. The anti-EpCAM antibodies are considered to significantly block, inhibit, reduce, antagonize, neutralize or otherwise interfere with EpCAM functional activity when the level of EpCAM activity in the presence of the anti-EpCAM antibody is decreased by at least 50%, e.g., 55%, 60%, 75%, 80%, 85% or 90% as compared to the level of EpCAM activity in the absence of binding with an anti-EpCAM antibody described herein. The anti-EpCAM antibodies are considered to partially modulate, block, inhibit, reduce, antagonize, neutralize or otherwise interfere with EpCAM functional activity when the level of EpCAM activity in the presence of the anti-EpCAM antibody is decreased by less than 95%, e.g., 10%, 20%, 25%, 30%, 40%, 50%, 60%, 75%, 80%, 85% or 90% as compared to the level of EpCAM activity in the absence of binding with an anti-EpCAM antibody described herein.

In some embodiments, the anti-EpCAM antibody moiety specifically binds to an EpCAM present on the surface of a cell. In some embodiments, the cell presents on its surface abnormally high levels of EpCAM. In some embodiments, the cell is a cancer cell. In some embodiments, the cancer cell is in a solid tumor. In some embodiments, the cancer cell is a metastatic cancer cell.

The anti-EpCAM antibody moieties in some embodiments comprise specific sequences or certain variants of such sequences. In some embodiments, the amino acid substitutions in the variant sequences do not substantially reduce the ability of the anti-EpCAM antibody moiety to bind the EpCAM. For example, alterations that do not substantially reduce EpCAM binding affinity may be made. Alterations that substantially improve EpCAM binding affinity or affect some other property, such as specificity, immunogenicity, ADCC or CDC, and/or cross-reactivity with related variants of the EpCAM, are also contemplated.

In some embodiments, the anti-EpCAM antibody or antigen-binding fragment thereof (such as an scFv) comprising a heavy chain variable region (VH) comprising one, two or three HVRs (or CDRs) from SEQ ID NO: 19, and/or a light chain variable region (VL) comprising one, two or three HVRs (or CDRs) from SEQ ID NO: 20. In some embodiments, the anti-EpCAM antibody or antigen-binding fragment thereof (such as an scFv) comprises a heavy chain variable region (VH) comprising three HVRs from SEQ ID NO: 19, and/or a light chain variable region (VL) comprising three HVRs from SEQ ID NO: 20.

In some embodiments, the anti-EpCAM antibody or antigen-binding fragment thereof (such as an scFv) comprises a heavy chain variable region (VH) comprising a HVR-H3 comprising the amino acid sequence of SEQ ID NO:15; and/or a light chain variable region (VL) comprising a HVR-L3 comprising the amino acid sequence of SEQ ID NO:18.

In some embodiments, the anti-EpCAM antibody or antigen-binding fragment comprises a VH comprising: (1) a HVR-H1 having one or two amino acid substitutions of SEQ ID NO: 13; (2) a HVR-H2 having one or two amino acid substitutions of SEQ ID NO: 14; and/or (3) a HVR-H3 having one or two amino acid substitutions of SEQ ID NO: 15. In some embodiments, the anti-EpCAM antibody or antigen-binding fragment comprises a VL comprising: (1) a HVR-L1 having one or two amino acid substitutions of SEQ ID NO: 16; (2) a HVR-L2 having one or two amino acid substitutions of SEQ ID NO: 17; and/or (3) a HVR-L3 having one or two amino acid substitutions of SEQ ID NO: 18.

In some embodiments, the anti-EpCAM antibody or antigen-binding fragment thereof (such as an scFv) comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18.

In some embodiments, the anti-EpCAM antibody or antigen-binding fragment thereof (such as an scFv) comprises a heavy chain variable region (VH) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:19, and/or a light chain variable region (VL) comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:20. In some embodiments, a $V_H$ or VL sequence having at least 90%, 91%, 92%, 93%, 94%, 95%, 96%, 97%, 98%, or 99% identity contains substitutions (e.g., conservative substitutions), insertions, or deletions relative to the reference sequence, but the Fab fragment comprising that sequence retains the ability to bind to EpCAM. In some embodiments, one or two amino acids have been substituted, inserted and/or deleted in any one or more of the HVRs. In some embodiments, substitutions, insertions, or deletions occur in regions outside the HVRs (i.e., in the FRs). In some embodiments, the anti-EpCAM antibody or antigen-binding fragment thereof (such as an scFv) comprises a heavy chain variable region (VH) comprising the amino acid sequence of SEQ ID NO: 19, and/or a light chain variable region (VL) comprising the amino acid sequence of SEQ ID NO: 20.

In some embodiments, the anti-EpCAM antibody is a full-length antibody. In some embodiments, the full-length anti-EpCAM antibody comprises an Fc sequence from an immunoglobulin, such as IgA, IgD, IgE, IgG, and IgM. In some embodiments, the full-length anti-EpCAM antibody comprises an Fc sequence of IgG, such as any of IgG1, IgG2, IgG3, or IgG4. In some embodiments, the full-length anti-EpCAM antibody comprises an Fc sequence of a human immunoglobulin. In some embodiments, the full-length anti-EpCAM antibody comprises an Fc sequence that has been altered or otherwise changed so that it has enhanced antibody dependent cellular cytotoxicity (ADCC) or complement dependent cytotoxicity (CDC) effector function.

Also provided is an isolated antibody or an antigen-binding fragment thereof which competes with any of the anti-EpCAM antibodies described herein for binding with EpCAM. In some embodiments, there is provided an isolated antibody or an antigen-binding fragment thereof which binds to the same epitope as any of the anti-EpCAM antibodies described herein. Methods for the screening of antibodies that possess the desired specificity include, but are not limited to, enzyme linked immunosorbent assay (ELISA) and other immunologically mediated techniques known within the art.

Those skilled in the art will recognize that it is possible to determine, without undue experimentation, if a monoclonal antibody has the same specificity as a monoclonal antibody of the invention (e.g., the anti-EpCAM antibody having a variable heavy chain of SEQ ID NO:19, and a variable light chain of SEQ ID NO:20) by ascertaining whether the former prevents the latter from binding to EpCAM. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with soluble EpCAM protein (with which it is normally reactive), and then add the monoclonal antibody being tested to determine if the monoclonal antibody being tested is inhibited in its ability to bind EpCAM. If the monoclonal antibody being tested is inhibited then, in all likelihood, it has the same, or functionally equivalent, epitopic specificity as the monoclonal antibody of the invention.

In some embodiments, the anti-EpCAM antibody is a monoclonal antibody, such as a monovalent antibody. In some embodiments, the anti-EpCAM antigen-binding fragment is in the form of a Fab, Fab', a F(ab)'2, single-chain Fv (scFv), an Fv fragment, a diabody, or a linear antibody.

In some embodiments, there is provided an anti-EpCAM scFv comprising a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the anti-EpCAM scFv comprises a VH comprising the amino acid sequence of SEQ ID NO: 19. In some embodiments, the anti-EpCAM scFv comprises a VL comprising the amino acid sequence of SEQ ID NO: 20. In some embodiments, the anti-EpCAM scFv comprises the amino acid sequence of SEQ ID NO: 21.

In some embodiments, the anti-EpCAM antibody is a multispecific antibody that binds to EpCAM, but also binds one or more other targets and optionally inhibits their function. Multispecific antibodies are monoclonal, preferably human or humanized, antibodies that have binding specificities for two or more different antigens (e.g., bispecific antibodies have binding specificities for at least two antigens). For example, one of the binding specificities can be for the EpCAM protein, the other one can be for any other antigen. In some embodiments, the other antigen is a cell-surface protein or receptor or receptor subunit. For example, the cell-surface protein can be CD3, such as CD3 epsilon. Thus, according to one embodiment, a bispecific antibody of this invention can bind both EpCAM and, e.g., a second cell surface receptor.

In some embodiments, the multi-specific anti-EpCAM molecule is, for example, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv (e.g., a bispecific T cell engager), a tandem tri-scFv, a tri(a)body, a bispecific Fab$_2$, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multi-specific anti-EpCAM molecule is a tandem scFv (e.g., a tandem di-scFv, such as a bispecific T cell engager).

Further provided are fusion proteins, conjugates, or isolated cells comprising any of the anti-EpCAM antibodies or antigen-binding fragments thereof described above.

In some embodiments, there is provided a multispecific (such as bispecific) Fab fusion protein comprising an anti-EpCAM antigen-binding fragment comprising a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18.

In some embodiments, the multispecific Fab fusion protein comprises a single anti-EpCAM antigen-binding fragment, wherein the anti-EpCAM antigen-binding fragment is fused to the N-terminus of the heavy chain polypeptide of the Fab fragment or the light chain polypeptide of the Fab fragment. In some embodiments, the multispecific Fab fusion protein comprises two anti-EpCAM antigen-binding fragment or two copies of anti-EpCAM antigen-binding fragments.

In some embodiments, there is provided a multispecific (such as bispecific) Fab fusion protein comprising a Fab fragment and an anti-EpCAM antigen-binding fragment, wherein the N-terminus of the heavy chain polypeptide or the N-terminus of the light chain polypeptide of the Fab fragment is fused to the anti-EpCAM antigen-binding fragment, and wherein the anti-EpCAM antigen-binding fragment comprises a heavy chain variable region (VH) comprising: a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15; and/or a light chain variable region (VL) comprising: a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18. In some embodiments, the multispecific Fab fusion protein comprises a Fab fragment, a first anti-EpCAM antigen-binding fragment, and a second anti-EpCAM antigen-binding fragment, wherein the N-terminus of the heavy chain polypeptide of the Fab fragment is fused to the first anti-EpCAM antigen-binding fragment, and wherein the N-terminus of the light chain polypeptide of the Fab fragment is fused to the second anti-EpCAM antigen-binding fragment. In some embodiments, the first anti-EpCAM antigen-binding fragment has the same sequence as the second anti-EpCAM antigen-binding fragment. In some embodiments, the anti-EpCAM antigen-binding fragment comprises a VH comprising the amino acid sequence of SEQ ID NO: 19. In some embodiments, the anti-EpCAM antigen-binding fragment comprises a VL comprising the amino acid sequence of SEQ ID NO: 20. In some embodiments, the anti-EpCAM antigen-binding fragment is an scFv, such as an scFv comprising the amino acid sequence of SEQ ID NO: 21.

The multispecific Fab fusion proteins comprising one or more anti-EpCAM antigen-binding fragments described herein may further comprise one or more features of the multispecific Fab fusion proteins described in subsection "Multispecific Fab fusion protein" of section II "Methods of treating cancer" described above.

In some embodiments, the multispecific Fab fusion protein comprises a Fab fragment that specifically binds to an immune effector molecule. In some embodiments, the Fab fragment binds to a T cell receptor. In some embodiments, the Fab fragment binds to CD3ε chain. In some embodiments, the Fab fragment binds to a cell surface target selected from FcγRI, FcγRIIa, FcγRIIb, FcγRIIIa, FcγRIIIa, NKG2D, CD25, CD28, CD137, CTLA-4, FAS, FGFR1, FGFR2, FGFR3, FGFR4, GITR, LTβR, TLR, TRAIL receptor 1, TRAIL receptor 2, EGFR, Her2/neu, and ErbB3.

In some embodiments, the Fab fragment specifically binds to CD3, such as the N-terminus of CD3 epsilon, for example, the N-terminal 1-27 amino acids of CD3 epsilon. In some embodiments, the Fab fragment comprises a heavy chain variable region (VH) comprising: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3; and/or a light chain variable region (VL) comprising: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6. In some embodiments, the Fab fragment comprises a VH comprising an amino acid sequence selected from the group consisting of SEQ ID NOs:7 and 39-43, and/or a VL comprising an amino acid sequence selected from the group consisting of SEQ ID NOs: 8 and 44-47. In some of the embodiments, the multispecific Fab fusion protein comprises a first polypeptide comprising the amino acid sequence of SEQ ID NO:22, and a second polypeptide comprising the amino acid sequence of SEQ ID NO:23.

In some embodiments, the anti-EpCAM antibody or antigen-binding fragment thereof is conjugated to a therapeutic agent (e.g., cytotoxic agent, a radioisotope and a chemotherapeutic agent) or a label for detecting EpCAM in patient samples or in vivo by imaging (e.g., radioisotope, fluorescent dye and enzyme). In some embodiments, the anti-EpCAM antibody or antigen-binding fragment thereof is conjugated to a toxin.

In some embodiments, there is provided an anti-EpCAM chimeric antigen receptor (CAR) comprising: a) an extracellular domain comprising any of the anti-EpCAM antibodies or antigen-binding fragments described herein; and b) an intracellular signaling domain. A transmembrane domain may be present between the extracellular domain and the intracellular domain. Between the extracellular domain and the transmembrane domain of the anti-EpCAM CAR, or between the intracellular domain and the transmembrane domain of the anti-EpCAM CAR, there may be a spacer domain, such as peptide linker (e.g., a flexible peptide linker). Examples of intracellular signaling domains for use in the anti-EpCAM CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability. Any method for producing a CAR may be used herein. See, for example, U.S. Pat. Nos. 6,410,319, 7,446,191, 7,514,537, WO 2002/077029, US2010/065818, US 2010/025177, US 2007/059298, and Berger C. et al., J. Clinical Investigation 118: 1 294-308 (2008).

In some embodiments, there is provided an anti-EpCAM recombinant T cell receptor (TCR) comprising an extracellular domain comprising any of the anti-EpCAM antibodies or antigen-binding fragments described herein. Methods of engineering TCRs have been described, for example, in see Stone J. D. et al. T Cell receptor engineering, Methods Enzymol. (2012) 503:189-222.

Also provided are isolated cells expressing the anti-EpCAM CAR or TCR, such as CAR-T or TCR-T cells, and methods of treating a disease (such as cancer) using the anti-EpCAM CAR or TCR, or cells expressing the ant-EpCAM or TCR thereof.

The anti-EpCAM antibodies or antigen-binding fragments described herein can be used in a variety of therapeutic and diagnostic methods. Further provided are methods of treating cancer in an individual, comprising administering an effective amount of the anti-EpCAM antibody or antigen-binding fragment thereof described above or pharmaceutical compositions thereof to the individual. For example, the anti-EpCAM antibodies (or antigen-binding fragments thereof) can be used alone or in combination with other agents in treating a disease characterized by abnormal EpCAM expression, including, but not limited to, head and neck cancer, pancreatic cancer, colorectal cancer, and lung cancer. The antibodies provided herein can also be used for detecting EpCAM protein in patients or patient samples.

Monoclonal Antibodies

Screening of monoclonal antibodies of the invention, can be also carried out, e.g., by measuring EpCAM-mediated signaling, and determining whether the test monoclonal antibody is able to modulate, block, inhibit, reduce, antagonize, neutralize or otherwise interfere with EpCAM-mediated signaling. These assays can include competitive binding assays. Additionally, these assays can measure a biologic readout.

Various procedures known within the art may be used for the production of monoclonal antibodies directed against EpCAM, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The EpCAM antibodies of the invention are monoclonal antibodies. Monoclonal antibodies that modulate, block, inhibit, reduce, antagonize, neutralize or otherwise interfere with EpCAM-mediated cell signaling are generated, e.g., by immunizing an animal with membrane bound and/or soluble EpCAM, such as, for example, human EpCAM or an immunogenic fragment, derivative or variant thereof. Alternatively, the animal is immunized with cells transfected with a vector containing a nucleic acid molecule encoding EpCAM such that EpCAM is expressed and associated with the surface of the transfected cells. Alternatively, the antibodies are obtained by screening a library that contains antibody or antigen binding domain sequences for binding to EpCAM. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to EpCAM.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as Chinese hamster ovary (CHO) cells, Human Embryonic Kidney (HEK) 293 cells, simian COS cells, PER.C6, NS0 cells, SP2/0, YB2/0, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies of the invention include fully human antibodies or humanized antibodies. These antibodies are suitable for administration to humans without engendering an immune response by the human against the administered immunoglobulin.

An anti-EpCAM antibody can be generated using any procedures known in the art. For example, anti-EpCAM antibodies can be identified using a modified RIMMS (Repetitive Immunization Multiple Sites) immunization strategy in mice and subsequent hybridoma generation. In other, alternative methods, an anti-EpCAM antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of EpCAM or fragments thereof. In another approach, an anti-EpCAM antibody can be produced by a process wherein at least one step of the process includes immunizing a transgenic, non-human animal with human EpCAM protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. Nos. 6,075,181 and 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963; 6,150,584; 6,114,598; 6,075,181; and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and an immune variable region, it is expected that certain human anti-chimeric antibody (HACA) responses will be observed, particularly in chronic or multi-dose utilizations of the antibody. Thus, it would be desirable to provide fully human antibodies against EpCAM in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG2, IgG3, and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to EpCAM expressing cells, soluble forms of EpCAM, epitopes or peptides thereof, and expression libraries thereto (See e.g., U.S. Pat. No. 5,703,057) which can thereafter be screened as described above for the activities described herein.

The EpCAM antibodies of the invention can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G., et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of EpCAM in a sample. The antibody can also be used to try to bind to and disrupt EpCAM-mediated signaling.

Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an $F(ab')_2$ fragment produced by pepsin digestion of an antibody molecule; (ii) an Fab fragment generated by reducing the disulfide bridges of an $F_{(ab')2}$ fragment; (iii) an Fab fragment generated by the treatment of the antibody molecule with papain and a reducing agent and (iv) $F_v$ fragments.

The invention also includes $F_v$, Fab, Fab' and $F(ab')_2$ anti-EpCAM fragments, single chain EpCAM antibodies, single domain antibodies (e.g., nanobodies or VHHs), multispecific (such as bispecific) anti-EpCAM antibodies, and heteroconjugate anti-EpCAM antibodies.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant EpCAM signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against EpCAM

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998)

and the citations therein for additional information related to formulations, excipients and carriers well known to pharmaceutical chemists.

In one embodiment, antibodies of the invention, which include a monoclonal antibody of the invention, may be used as therapeutic agents. Such agents will generally be employed to diagnose, prognose, monitor, treat, alleviate, and/or prevent a disease or pathology associated with aberrant EpCAM expression, activity and/or signaling in a subject. A therapeutic regimen is carried out by identifying a subject, e.g., a human patient suffering from (or at risk of developing) a disease or disorder associated with aberrant EpCAM expression, activity and/or signaling, e.g., a cancer or other neoplastic disorder, using standard methods. An antibody preparation, preferably one having high specificity and high affinity for its target antigen, is administered to the subject and will generally have an effect due to its binding with the target. Administration of the antibody may abrogate or inhibit or interfere with the expression, activity and/or signaling function of the target (e.g., EpCAM). Administration of the antibody may abrogate or inhibit or interfere with the binding of the target (e.g., EpCAM) with an endogenous ligand to which it naturally binds. For example, the antibody binds to the target and modulates, blocks, inhibits, reduces, antagonizes, neutralizes, or otherwise interferes with EpCAM expression, activity and/or signaling.

Diseases or disorders related to aberrant EpCAM expression, activity and/or signaling include, by way of non-limiting example, hematological cancer and/or solid tumors. Hematological cancers include, e.g., leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Symptoms associated with cancers and other neoplastic disorders include, for example, inflammation, fever, general malaise, fever, pain, often localized to the inflamed area, loss of appetite, weight loss, edema, headache, fatigue, rash, anemia, muscle weakness, muscle fatigue and abdominal symptoms such as, for example, abdominal pain, diarrhea or constipation.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 100 mg/kg body weight. Common dosing frequencies may range, for example, from twice daily to once a week.

Efficaciousness of treatment is determined in association with any known method for diagnosing or treating the particular inflammatory-related disorder. Alleviation of one or more symptoms of the inflammatory-related disorder indicates that the antibody confers a clinical benefit.

In another embodiment, antibodies directed against EpCAM may be used in methods known within the art relating to the localization and/or quantitation of EpCAM (e.g., for use in measuring levels of EpCAM within appropriate physiological samples, for use in diagnostic methods, for use in imaging the protein, and the like). In a given embodiment, antibodies specific to EpCAM, or derivative, fragment, analog or homolog thereof, that contain the antibody derived antigen binding domain, are utilized as pharmacologically active compounds (referred to hereinafter as "Therapeutics").

In another embodiment, an antibody specific for EpCAM can be used to isolate a EpCAM polypeptide, by standard techniques, such as immunoaffinity, chromatography or immunoprecipitation. Antibodies directed against the EpCAM protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody according to the invention can be used as an agent for detecting the presence of EpCAM (or a protein fragment thereof) in a sample. In some embodiments, the antibody contains a detectable label. Antibodies are polyclonal, or more preferably, monoclonal. An intact antibody, or a fragment thereof (e.g., Fab, scFv, or $F(ab')_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

IV. Methods of Preparation

The MSFPs or the anti-EpCAM antibodies (or antigen-binding fragments thereof) described herein may be prepared by any of the known protein expression and purification methods in the art.

In some embodiments, the present application provides isolated nucleic acids encoding one or more of the polypeptide chains of any one of the MSFPs or the anti-EpCAM antibodies (or antigen-binding fragments thereof) described herein. In some embodiments, the isolated nucleic acid comprises the nucleic acid sequence of SEQ ID NO: 31 or SEQ ID NO: 32. The isolated nucleic acids may be DNA or RNA.

(Nucleic acid encoding SEQ ID NO: 22)
SEQ ID NO: 31
gaggtgcagctggtggagtcaggggggaggcttggtccagcctgggggatc
ctgagactctcctgtgcagcctctggattcacctttagtaattattggat
gagctgggtccgccaggctccagggaaggggctggagtgggtggccaaca
taaagcaagatggaagtgagaaattctatgcggactctgtgaagggccga
ttcaccatctccagagacaacgccaagaactcactgtatctgcaaatgaa
cagcctgagagccgaagacacggctgtctattactgtgcgagagtggggc
cgtcctgggagcaggactactggggccagggaaccctggtcactgtctcg
gccggtggcggtggcagcggcggtggtgggtccggtggcggcggatctgg
cgcgcagtctgtactgactcaaccgccctcagtgtctggggcccagggc
agagggtcaccatctcctgcactgggagcagctccaacatcgggtcttat
tatggtgtgcactggtaccagcagcttccaggaacagcccccaaactcct
catctattctgacactaatcgaccctcaggggtccctgaccgattctctg
gctccaagtctggcacctcggcctccctggccatcactgggctccaggct
gaggatgaggctgattattactgccagtcgtatgacaagggcttcgggca
ccgggtgttcggcggagggaccaagctgaccgtcctagggggcgaggtgc
agctggtggagtctggggggaggcttggtacagcctggggggtccctgaga
ctctcctgtgcagcctctggattcacctttaacacctacgccatgaactg
ggtccgccaggctccagggaaggggctggagtgggtcgcacgcataagaa gtaaatataataattatgcaacatattatgccgattcagtgaaagaccgg
ttcaccatctccagagacgattccaagaacacgctgtatctgcaaatgaa
cagcctgagagccgaggacacggccgtatattactgtgtgagacatggga
actcggtaatagctacgtttcctggtttgcttactggggccaagggaca
atggtcaccgtctcttcagctagcaccaagggcccatccgtcttccccct
ggcaccctcctccaagagcacctctgggggcacagcggccctgggctgcc
tggtcaaggactacttccccgaaccggtgacggtgtcgtggaactcaggc
gccctgaccagcggcgtgcacaccttcccggctgtcctacagtcctcagg
actctactccctcagcagcgtggtgaccgtgccctccagcagcttgggca
cccagacctacatctgcaacgtgaatcacaagcccagcaacaccaaggtg
gacaagaaagttgagcccaaatcttgtccaccgtgctcatga (Nucleic acid encoding SEQ ID NO: 23)
SEQ ID NO: 32
gaggtgcagctggtggagtcaggggggaggcttggtccagcctgggggatc
cctgagactctcctgtgcagcctctggattcacctttagtaattattgga
tgagctgggtccgccaggctccagggaaggggctggagtgggtggccaac
ataaagcaagatggaagtgagaaattctatgcggactctgtgaagggccg
attcaccatctccagagacaacgccaagaactcactgtatctgcaaatga
acagcctgagagccgaagacacggccgtctattactgtgcgagagtgggg
ccgtcctgggagcaggactactggggccagggaaccctggtcactgtctc
ggccggtggcggtggcagcggcggtggtgggtccggtggcggcggatctg
gcgcgcagtctgtactgactcaaccgccctcagtgtctggggcccaggg
cagagggtcaccatctcctgcactgggagcagctccaacatcgggtctta
ttatggtgtgcactggtaccagcagcttccaggaacagcccccaaactcc
tcatctattctgacactaatcgaccctcaggggtccctgaccgattctct
ggctccaagtctggcacctcggcctccctggccatcactgggctccaggc
tgaggatgaggctgattattactgccagtcgtatgacaagggcttcgggc
accgggtgttcggcggagggaccaagctgaccgtcctagggggccaggct
gtggtgactcaggagccctcactgactgtgtcccaggagggacagtcac
tctcacctgtcgctcaagtactggggctgttacaactagtaactatgcca
actgggtccagcagaaacctggacaagcacccaggggtctgattggtggt
accaacaagcgagctccaggtaccctgcccggttctcaggctccctcct
tgggggcaaagctgccctgacactgtcaggtgtgcagcctgaggacgagg
ctgagtattactgcgctctatggtacagcaacctctgggtgttcggcgga
gggaccaagctgaccgtcctaggccaaccgaaagcggcgccctcggtcac
tctgttcccgccctcctctgaggagcttcaagccaacaaggccacactgg
tgtgtctcataagtgacttctacccgggagccgtgacagtggcctggaag
gcagatagcagcccgtcaaggcgggagtggagaccaccacccctccaa
acaaagcaacaacaagtacgcggccagcagctatctgagcctgacgcctg
agcagtggaagtcccacagaagctacagctgccaggtcacgcatgaaggg
agcaccgtggagaagacagtggcccctacagaatgtccaccgtgctcatg
a In some embodiments, the isolated nucleic acid is inserted into a vector, such as an expression vector, a viral vector, or a cloning vector. For expression of the nucleic acids, the vector may be introduced into a host cell to allow expression of the nucleic acids within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter. EF1a promoter, CMV promoter, and SV40 promoter. Enhancer sequences may be selected to enhance the transcription of the nucleic acids. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell. In some embodiments, the isolated nucleic acids further comprise a nucleic acid sequence encoding a signal peptide. In some embodiments, the signal peptide comprises the amino acid sequence of SEQ ID NO: 33. In some embodiments, the nucleic acid sequence encoding the signal peptide comprises the nucleic acid sequence of SEQ ID NO: 34.

```
(Signal peptide)
                                           SEQ ID NO: 33
MEWSWVFLFFLSVTTGVHS (Nucleic acid encoding signal peptide)
                                           SEQ ID NO: 34
atggaatggagctgggtctttctcttcttcctgtcagtaacgactggtgt ccactcc
```

In some embodiments, there is provided an isolated host cell containing the vector described above. The host cells containing the vector may be useful in expression or cloning of the isolated nucleic acids. Suitable host cells can include, without limitation, prokaryotic cells, fungal cells, yeast cells, or higher eukaryotic cells such as mammalian cells. The expression of antibodies and antigen-binding fragments in prokaryotic cells such as E. coli is well established in the art. For a review, see for example Pluckthun, A. BioTechnology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560. Higher eukaryotic cells, in particular, those derived from multicellular organisms can be used for expression of glycosylated polypeptides. Suitable higher eukaryotic cells include, without limitation, invertebrate cells and insect cells, and vertebrate cells.

The vector can be introduced to the host cell using any suitable methods known in the art, including, but not limited to, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In some embodiments, the host cells comprise a first vector encoding a first polypeptide and a second vector encoding a second polypeptide. In some embodiments, the host cells comprise a single vector comprising isolated nucleic acids encoding a first polypeptide and a second polypeptide.

In some embodiments, the present application provides methods of expressing any of the MSFPs or the anti-EpCAM antibodies (or antigen-binding fragments thereof) described herein, comprising culturing the isolated host cell containing the vector and recovering the MSFP or anti-EpCAM antibody (or antigen-binding fragment thereof) from the cell culture. The isolated host cells are cultured under conditions that allow expression of the isolated nucleic acids inserted in the vectors. Suitable conditions for expression of polynucleotides may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

In some embodiments, the polypeptides expressed in the host cell can form a dimer and thus produce an MSFP or the anti-EpCAM antibody (or antigen-binding fragment thereof) described herein. In some embodiments, the polypeptide expressed in the host cell can form a polypeptide complex which is a homodimer. In some embodiments, wherein the host cells express a first polynucleotide and a second polynucleotide, the first polynucleotide and the second polynucleotide can form a polypeptide complex which is a heterodimer.

In some embodiments, the polypeptide complex (such as the MSFP or the anti-EpCAM antibody or antigen-binding fragment thereof) may be formed inside the host cell. For example, the dimer may be formed inside the host cell with the aid of relevant enzymes and/or cofactors. In some embodiments, the polypeptide complex may be secreted out of the cell. In some embodiments, a first polypeptide and a second polypeptide may be secreted out of the host cell and form a dimer (such as the MSFP or the anti-EpCAM antibody or antigen-binding fragment thereof) outside of the host cell.

In some embodiments, a first polypeptide and a second polypeptide may be separately expressed and allowed to dimerize to form the MSFP or the anti-EpCAM antibody (or antigen-binding fragment thereof) under suitable conditions. For example, the first polypeptide and the second polypeptide may be combined in a suitable buffer and allow the first protein monomer and the second protein monomer to dimerize through appropriate interactions such as hydrophobic interactions. In some embodiments, the first polypeptide and the second polypeptide may be combined in a suitable buffer containing an enzyme and/or a cofactor which can promote the dimerization of the first polypeptide and the second polypeptide. In some embodiments, the first polypeptide and the second polypeptide may be combined in a suitable vehicle and allow them to react with each other in the presence of a suitable reagent and/or catalyst.

The expressed polypeptide(s) and/or the polypeptide complex can be collected using any suitable methods. The polypeptide(s) and/or the polypeptide complex can be expressed intracellularly, in the periplasmic space or be secreted outside of the cell into the medium. If the polypeptide and/or the polypeptide complex are expressed intracellularly, the host cells containing the polypeptide and/or the polypeptide complex may be lysed and polypeptide and/or the polypeptide complex may be isolated from the lysate by removing the unwanted debris by centrifugation or ultrafiltration. If the polypeptide and/or the polypeptide complex is secreted into periplasmic space of E. coli, the cell paste may be thawed in the presence of agents such as sodium acetate (pH 3.5), EDTA, and phenylmethylsulfonylfluoride (PMSF) for about 30 min, and cell debris can be removed by centrifugation (Carter et al., BioTechnology 10:163-167 (1992)). If the polypeptide and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or a antibiotics may be included in the collection and concentration steps to inhibit protein degradation and/or growth of contaminated microorganisms.

The expressed polypeptide(s) and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis. 2007; Janson, J. C., et al, Protein purification: principles, high resolution methods and applications, published by Wiley-VCH, 1998).

In some embodiments, the polypeptides and/or polypeptide dimer complexes can be purified by affinity chromatography. In some embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol. Meth. 62:1-13 (1983)); Zettlit, K. A., Antibody Engineering, Part V, 531-535, 2010). In some embodiments, protein G chromatography can be useful for purification of polypeptides and/or polypeptide complexes comprising IgG γ3 heavy chain (Guss et al., EMBO J. 5:1567 1575 (1986)). In some embodiments, protein L chromatography can be useful for purification of polypeptides and/or polypeptide complexes comprising κ light chain (Sudhir, P., Antigen engineering protocols, Chapter 26, published by Humana Press, 1995; Nilson, B. H. K. at al, J. Biol. Chem., 267, 2234-2239 (1992)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX resin (J. T. Baker, Phillipsburg, N.J.) is useful for purification.

V. Pharmaceutical Compositions, Unit Dosages, Articles of Manufacture, and Kits Further provided by the present application are pharmaceutical compositions comprising any one of the MSFPs or the anti-EpCAM antibodies (or antigen-binding fragments thereof) as described herein, and a pharmaceutically acceptable carrier.

The pharmaceutical compositions may be suitable for a variety of modes of administration described herein, including for example systemic or localized administration. In some embodiments, the pharmaceutical composition is formulated for intravenous administration. In some embodiments, the pharmaceutical composition is formulated for subcutaneous administration. In some embodiments, the pharmaceutical composition is formulated for local administration to a tumor site. In some embodiments, the pharmaceutical composition is formulated for intratumoral injection.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

The pharmaceutical compositions to be used for in vivo administration are generally formulated as sterile, substantially isotonic, and in full compliance with all Good Manufacturing Practice (GMP) regulations of the U.S. Food and Drug Administration. Sterility is readily accomplished by filtration through sterile filtration membranes. In some embodiments, the composition is free of pathogen. For injection, the pharmaceutical composition can be in the form of liquid solutions, for example in physiologically compatible buffers such as Hank's solution or Ringer's solution. In addition, the pharmaceutical composition can be in a solid form and re-dissolved or suspended immediately prior to use. Lyophilized compositions are also included.

In some embodiment, the pharmaceutical composition is formulated in accordance with routine procedures as a pharmaceutical composition adapted for injection intravenously, introperitoneally, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In some embodiments, the pharmaceutical composition is suitable for administration to a human. In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

Also provided are unit dosage forms of the MSFPs, anti-EpCAM antibodies (or antigen-binding fragments thereof), or compositions thereof. Each dosage may contain from about 0.01 µg to about 10 mg, including for example any of about 0.01 µg to about 10 mg, about 0.01 µg to about 5 mg, about 0.01 µg to about 1 mg, about 0.1 µg to about 300 µg, about 0.1 µg to about 200 µg, about 0.1 µg to about 100 µg, about 0.1 µg to about 90 µg, about 0.1 µg to about 80 µg, about 0.1 µg to about 70 µg, about 0.1 µg to about 60 µg, about 0.1 µg to about 50 µg, about 0.1 µg to about 40 µg, about 0.1 µg to about 30 µg, about 0.1 µg to about 20 µg, about 0.1 µg to about 10 µg, about 0.1 µg to about 5 µg, or about 0.1 µg to about 1 µg. In some embodiments, the unit dosage forms of the MSFP, anti-EpCAM antibody (or antigen-binding fragment thereof), or composition thereof is within any of the following range, wherein the ranges have an upper limit of any of: 0.1 µg, 0.2 µg, 0.3 µg, 0.4 µg, 0.5 µg, 0.6 µg, 0.7 µg, 0.8 µg, 0.9 µg, 1 µg, 5 µg, 10 µg, 15 µg, 20 µg, 25 µg, or 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 1000 µg, 1500 µg, 2000 µg, 2500 µg, 3000 µg, 6000 µg, or 10000 µg, and an independently selected lower limit of any of 0.1 µg, 0.2 µg, 0.3 µg, 0.4 µg, 0.5 µg, 0.6 µg, 0.7 µg, 0.8 µg, 0.9 µg, 1 µg, 5 µg, 10 µg, 15 µg, 20 µg, 25 µg, or 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 1000 µg, 1500 µg, 2000 µg, 2500 µg, 3000 µg, 6000 µg, or 10000 µg, and wherein the lower limit is less than the upper limit. The term "unit dosage form" refers to a physically discrete unit suitable as unitatry dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

The present application further provides articles of manufacture comprising the compositions (such as pharmaceutical compositions) described herein in suitable packaging. Suitable packaging for compositions (such as MSFP or anti-EpCAM antibody compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present application also provides kits comprising compositions (such as pharmaceutical compositions) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

EXEMPLARY EMBODIMENTS

The invention provides the following embodiments:

1. A method of treating a cancer in an individual, comprising administering to the individual an effective amount of a multispecific Fab fusion protein comprising: a Fab fragment that specifically binds to CD3, and a binding domain that specifically binds to EpCAM; wherein the binding domain is fused to an N-terminus of the Fab fragment; and wherein the multispecific Fab fusion protein is administered at a dose of about 0.01 µg/kg to about 250 µg/kg.

2. The method of embodiment 1, wherein the binding domain is an scFv.

3. The method of embodiment 2, wherein the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment.

4. The method of embodiment 3, wherein the first scFv and the second scFv have the same sequence.

5. The method of any one of embodiments 1-4, wherein the multispecific Fab fusion protein is administered intravenously.

6. The method of any one of embodiments 1-5, wherein the multispecific Fab fusion protein is administered at a low frequency.

7. The method of embodiment 6, wherein the multispecific Fab fusion protein is administered twice weekly.

8. The method of any one of embodiments 1-7, wherein the multispecific Fab fusion protein is administered at a dose equivalent to about 0.1 µg/kg to about 100 µg/kg for a cynomolgus monkey.

9. The method of any one of embodiments 1-8, wherein the multispecific Fab fusion protein is administered at a dose that does not induce cytokine storm.

10. The method of embodiment 9, wherein multispecific Fab fusion protein is administered at a dose equivalent to no higher than about 30 µg/kg for a cynomolgus monkey.

11. The method of any one of embodiments 1-10, wherein the multispecific Fab fusion protein is administered at a first dose for a first period of time to the individual, and consecutively, the multispecific Fab fusion protein is administered at a second dose for a second period of time to the individual, and wherein the second dose exceeds the first dose.

12. The method of embodiment 11, wherein the second period of time exceeds the first period of time.

13. The method of embodiment 11 or embodiment 12, wherein the first period of time is at least about 7 days.

14. The method of any one of embodiments 11-13, wherein the second period of time is at least about 2 weeks.

15. The method of any one of embodiments 11-14, wherein the first dose is no more than about 1 µg/kg.

16. The method of any one of embodiments 11-14, wherein the second dose is about 0.1 µg/kg to about 10 µg/kg.

17. The method of any one of embodiments 1-16, further comprising administering a glucocorticoid to the individual.

18. The method of embodiment 17, wherein the glucocorticoid is dexamethasone.

19. The method of embodiment 17 or embodiment 18, wherein the glucocorticoid is administered prior to the first dose of the multispecific Fab fusion protein.

20. The method of any one of embodiments 17-19, wherein the glucocorticoid is administered at a dose of about 0.1 mg/kg to about 5 mg/kg.

21. The method of any one of embodiments 1-20, wherein the individual is a human individual.

22. The method of any one of embodiments 1-21, wherein the Fab fragment specifically binds to the N-terminus of CD3 epsilon.

23. The method of embodiment 22, wherein the Fab fragment specifically binds to an epitope within amino acids 1-27 of CD3 epsilon.

24. The method of embodiment 23, wherein the VH of the Fab fragment comprises a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3.

25. The method of embodiment 23 or embodiment 24, wherein the VL of the Fab fragment comprises: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6.

26. The method of any one of embodiments 23-25, wherein the VH of the Fab fragment comprises an amino acid sequence having at least about 85% (such as about 100%) sequence identity to an amino acid sequence selected from the group consisting of SEQ ID NOs:7 and 39-43.

27. The method of any one of embodiments 23-26, wherein the VL of the Fab fragment comprises an amino acid sequence having at least about 85% (such as about 100%) sequence identity to an amino acid sequence selected from the group consisting of SEQ ID NOs: 8 and 44-47.

28. The method of any one of embodiments 23-27, wherein the Fab fragment comprises a human immunoglobulin heavy chain constant region 1 (CH1) comprising the amino acid sequence of SEQ ID NO:9.

29. The method of any one of embodiments 23-28, wherein the Fab fragment comprises a human lambda light chain constant region comprising the amino acid sequence of SEQ ID NO:10.

30. The method of any one of embodiments 23-29, wherein the CH1 and the CL of the Fab fragment are connected by one or more disulfide bonds.

31. The method of embodiment 30, wherein the Fab fragment comprises a first polypeptide comprising an amino acid sequence having at least about 85% (such as about 100%) sequence identity to the amino acid sequence of SEQ ID NO:11.

32. The method of embodiment 30 or embodiment 31, wherein the Fab fragment comprises a second polypeptide comprising an amino acid sequence having at least about 85% (such as about 100%) sequence identity to the amino acid sequence of SEQ ID NO:12.

33. The method of any one of embodiments 1-32, wherein the cancer is an EpCAM-positive solid cancer.

34. The method of embodiment 33, wherein the EpCAM-positive solid cancer is a carcinoma or adenocarcinoma.

35. The method of any one of embodiments 1-34, wherein the cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, endometrial cancer, breast cancer, bile duct cancer, and head and neck cancer.

36. The method of embodiment 35, wherein the cancer is colorectal adenocarcinoma.

37. The method of embodiment 35, wherein the cancer is lung adenocarcinoma.

38. The method of any one of embodiments 2-37, wherein the scFv comprises an N—VH-VL-C fusion polypeptide.

39. The method of any one of embodiments 2-38, wherein the VH of the scFv comprises a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15.

40. The method of any one of embodiments 2-39, wherein the VL of the scFv comprises a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18.

41. The method of any one of embodiments 2-40, wherein the VH of the scFv comprises an amino acid sequence having at least about 85% (such as about 100%) sequence identity to the amino acid sequence of SEQ ID NO: 19.

42. The method of any one of embodiments 2-41, wherein the VL of the scFv comprises an amino acid sequence having at least about 85% (such as about 100%) sequence identity to the amino acid sequence of SEQ ID NO: 20.

43. The method of embodiment 42, wherein the scFv comprises an amino acid sequence having at least about 85% (such as about 100%) sequence identity to the amino acid sequence of SEQ ID NO:21.

44. The method of any one of embodiments 1-43, wherein the multispecific Fab fusion protein comprises a first polypeptide comprising an amino acid sequence having at least about 85% (such as about 100%) sequence identity to the amino acid sequence of SEQ ID NO:22.

45. The method of any one of embodiments 1-44, wherein the multispecific Fab fusion protein comprises a second polypeptide comprising an amino acid sequence having at least about 85% (such as about 100%) sequence identity to the amino acid sequence of SEQ ID NO:23.

46. An anti-EpCAM antibody or antigen-binding fragment thereof, comprising a heavy chain variable region comprising: (1) a HVR-H1 comprising the amino acid sequence of SEQ ID NO:13; (2) a HVR-H2 comprising the amino acid sequence of SEQ ID NO:14; and (3) a HVR-H3 comprising the amino acid sequence of SEQ ID NO:15; and a light chain variable region comprising: (1) a HVR-L1 comprising the amino acid sequence of SEQ ID NO:16; (2) a HVR-L2 comprising the amino acid sequence of SEQ ID NO:17; and (3) a HVR-L3 comprising the amino acid sequence of SEQ ID NO:18.

47. The anti-EpCAM antibody or antigen-binding fragment thereof according to embodiment 46, wherein the heavy chain variable domain sequence comprises a VH comprising an amino acid sequence having at least about 85% (such as about 100%) sequence identity to the amino acid sequence of SEQ ID NO:19.

48. The anti-EpCAM antibody or antigen-binding fragment thereof according to embodiment 46 or embodiment 47, wherein the light chain variable domain sequence comprises a VL comprising an amino acid sequence having at least about 85% (such as about 100%) sequence identity to the amino acid sequence of SEQ ID NO:20.

49. The anti-EpCAM antibody or antigen-binding fragment thereof according to any one of embodiments 46-48, wherein the anti-EpCAM antibody comprises an Fc sequence of a human IgG.

50. The anti-EpCAM antibody of any one of embodiments 46-49, wherein the anti-EpCAM antibody is a multispecific antibody.

51. The antigen-binding fragment of the anti-EpCAM antibody according to any one of embodiments 46-48, wherein the antigen-binding fragment is a single-chain Fv (scFv).

52. The antigen-binding fragment of the anti-EpCAM antibody of embodiment 51, wherein the scFv comprises an amino acid sequence having at least about 85% (such as about 100%) sequence identity to the amino acid sequence of SEQ ID NO:21.

53. A multispecific Fab fusion protein comprising the anti-EpCAM antigen-binding fragment of any one of embodiments 46-48 and 51-52.

54. The multispecific Fab fusion protein of embodiment 53, comprising a Fab fragment that specifically binds to CD3, a first copy of the anti-EpCAM antigen-binding fragment, and a second copy of the anti-EpCAM antigen binding fragment; wherein the first copy of the anti-EpCAM antigen-binding fragment is fused to the N-terminus of the VH of the Fab fragment; and wherein the second copy of the anti-EpCAM antigen binding fragment is fused to the N-terminus of the VL of the Fab fragment.

55. The multispecific Fab fusion protein of embodiment 54, wherein the Fab fragment specifically binds to the N-terminus of CD3 epsilon.

56. The multispecific Fab fusion protein of embodiment 55, wherein the Fab fragment specifically binds to an epitope within amino acids 1-27 of CD3 epsilon.

57. The multispecific Fab fusion protein of embodiment 56, wherein the VH of the Fab fragment comprises: a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3.

58. The multispecific Fab fusion protein of embodiment 56 or embodiment 57, wherein the VL of the Fab fragment comprises: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6.

59. The multispecific Fab fusion protein of any one of embodiments 56-58, wherein the VH of the Fab fragment comprises an amino acid sequence having at least about 85% (such as about 100%) sequence identity to an amino acid sequence selected from the group consisting of SEQ ID NOs:7 and 39-43.

60. The multispecific Fab fusion protein of any one of embodiments 56-59, wherein the VL of the Fab fragment comprises an amino acid sequence having at least about 85% (such as about 100%) sequence identity to an amino acid sequence selected from the group consisting of SEQ ID NOs: 8 and 44-47.

61. The multispecific Fab fusion protein of any one of embodiments 53-60, wherein the Fab fragment comprises a human immunoglobulin heavy chain constant region 1 (CH1) comprising the amino acid sequence of SEQ ID NO:9.

62. The multispecific Fab fusion protein of any one of embodiments 53-61, wherein the Fab fragment comprises a human lambda light chain constant region comprising the amino acid sequence of SEQ ID NO:10.

63. The multispecific Fab fusion protein of any one of embodiments 53-62, wherein the CH1 and the CL of the Fab fragment are connected by one or more disulfide bonds.

64. The multispecific Fab fusion protein of any one of embodiments 56-63, wherein the Fab fragment comprises a first polypeptide comprising an amino acid sequence having at least about 85% (such as about 100%) sequence identity to the amino acid sequence of SEQ ID NO:11.

65. The multispecific Fab fusion protein of any one of embodiments 56-64, wherein the Fab fragment comprises a second polypeptide comprising an amino acid sequence having at least about 85% (such as about 100%) sequence identity to the amino acid sequence of SEQ ID NO:12.

66. An isolated nucleic acid molecule that encodes the anti-EpCAM antibody or antigen-binding fragment thereof or the multispecific Fab fusion protein according to any one of embodiments 46-65.

67. An expression vector encoding the isolated nucleic acid molecule of embodiment 66.

68. An isolated host cell comprising the expression vector of embodiment 67.

69. A method of producing an anti-EpCAM antibody or antigen-binding fragment thereof or the multispecific Fab fusion protein comprising culturing the isolated host cell of embodiment 68 and recovering the anti-EpCAM antibody or antigen-binding fragment thereof or the multispecific Fab fusion protein from the cell culture.

70. A composition comprising the anti-EpCAM antibody or antigen-binding fragment thereof or the multispecific Fab fusion protein according to any one of embodiments 46-65 and a pharmaceutically acceptable carrier.

71. A method of treating cancer in an individual, comprising administering an effective amount of the composition of embodiment 70 to the individual.

72. Use of the anti-EpCAM antibody or antigen-binding fragment thereof or the multispecific Fab fusion protein of any one of embodiments 46-65 in the preparation of a medicament for treating a cancer in an individual.

73. Use of a multispecific Fab fusion protein in the preparation of a medicament for treating a cancer in an individual, wherein the multispecific Fab fusion protein comprises a Fab fragment that specifically binds to CD3, and a binding domain that specifically binds to EpCAM; wherein the binding domain is fused to an N-terminus of the Fab fragment.

74. The use of embodiment 73, wherein the binding domain is an scFv.

75. The use of embodiment 74, wherein the multispecific Fab fusion protein comprises a first scFv that specifically binds to EpCAM, and a second scFv that specifically binds to EpCAM; wherein the first scFv is fused to the N-terminus of the VH of the Fab fragment; and wherein the second scFv is fused to the N-terminus of the VL of the Fab fragment.

76. The use of embodiment 75, wherein the first scFv and the second scFv have the same sequence.

77. The use of any one of embodiments 73-76, wherein the multispecific Fab fusion protein is administered intravenously.

78. The use of any one of embodiments 73-77, wherein the multispecific Fab fusion protein is administered at a low frequency.

79. The use of embodiment 78, wherein the multispecific Fab fusion protein is administered twice weekly.

80. The use of any one of embodiments 73-79, wherein the multispecific Fab fusion protein is administered at a dose of about 0.1 µg/kg to about 250 µg/kg.

81. The use of embodiment 80, wherein the multispecific Fab fusion protein is administered at a dose equivalent to about 0.1 µg/kg to about 100 µg/kg for a cynomolgus monkey.

82. The use of any one of embodiments 63-81, wherein the multispecific Fab fusion protein is administered at a dose that does not induce cytokine storm.

83. The use of any one of embodiments 63-82, wherein the multispecific Fab fusion protein is administered at a first dose for a first period of time to the individual, and consecutively, the multispecific Fab fusion protein is administered at a second dose for a second period of time to the individual, and wherein the second dose exceeds the first dose.

84. The use of embodiment 83, wherein the second period of time exceeds the first period of time.

85. The use of embodiment 83 or embodiment 84, wherein the first period of time is at least about 7 days.

86. The use of any one of embodiments 83-85, wherein the second period of time is at least about 2 weeks.

87. The use of any one of embodiments 83-86, wherein the first dose is no more than about 1 µg/kg.

88. The use of any one of embodiments 83-87, wherein the second dose is about 0.1 µg/kg to about 10 µg/kg.

89. The use of any one of embodiments 83-88, further comprising administering a glucocorticoid to the individual.

90. The use of embodiment 89, wherein the glucocorticoid is dexamethasone.

91. The use of embodiment 89 or embodiment 90, wherein the glucocorticoid is administered prior to the first dose of the multispecific Fab fusion protein.

92. The use of any one of embodiments 89-91, wherein the glucocorticoid is administered at a dose of about 0.1 mg/kg to about 5 mg/kg.

93. The use of any one of embodiments 73-92, wherein the individual is a human individual.

94. The use of any one of embodiments 73-93, wherein the Fab fragment specifically binds to the N-terminus of CD3 epsilon.

95. The use of embodiment 94, wherein the Fab fragment specifically binds to an epitope within amino acids 1-27 of CD3 epsilon.

96. The use of embodiment 95, wherein the VH of the Fab fragment comprises a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3.

97. The use of embodiment 95 or embodiment 96, wherein the VL of the Fab fragment comprises: a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6.

98. The use of any one of embodiments 95-97, wherein the VH of the Fab fragment comprises an amino acid sequence having at least about 85% (such as about 100%) sequence identity to an amino acid sequence selected from the group consisting of SEQ ID NOs:7 and 39-43.

99. The use of any one of embodiments 95-98, wherein the VL of the Fab fragment comprises an amino acid sequence having at least about 85% (such as about 100%) sequence identity to an amino acid sequence selected from the group consisting of SEQ ID NOs: 8 and 44-47.

100. The use of any one of embodiments 95-99, wherein the Fab fragment comprises a human immunoglobulin heavy chain constant region 1 (CH1) comprising the amino acid sequence of SEQ ID NO:9.

101. The use of any one of embodiments 95-100, wherein the Fab fragment comprises a human lambda light chain constant region comprising the amino acid sequence of SEQ ID NO:10.

102. The use of any one of embodiments 95-101, wherein the CH1 and the CL of the Fab fragment are connected by one or more disulfide bonds.

103. The use of embodiment 102, wherein the Fab fragment comprises a first polypeptide comprising an amino acid sequence having at least about 85% (such as about 100%) sequence identity to the amino acid sequence of SEQ ID NO:11.

104. The use of embodiment 102 or embodiment 103, wherein the Fab fragment comprises a second polypeptide comprising an amino acid sequence having at least about 85% (such as about 100%) sequence identity to the amino acid sequence of SEQ ID NO:12.

105. The use of any one of embodiments 73-104, wherein the cancer is an EpCAM-positive solid cancer.

106. The use of embodiment 105, wherein the EpCAM-positive solid cancer is a carcinoma or adenocarcinoma.

107. The use of any one of embodiments 73-106, wherein the cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, endometrial cancer, breast cancer, bile duct cancer, and head and neck cancer.

108. The use of embodiment 107, wherein the cancer is colorectal adenocarcinoma.

109. The use of embodiment 107, wherein the cancer is lung adenocarcinoma.

110. The use of any one of embodiments 74-109, wherein the scFv comprises an N—VH-VL-C fusion polypeptide.

111. The use of any one of embodiments 74-110, wherein the VH of the scFv comprises a HVR-H1 comprising the amino acid sequence of SEQ ID NO:13; a HVR-H2 comprising the amino acid sequence of SEQ ID NO:14; and a HVR-H3 comprising the amino acid sequence of SEQ ID NO:15.

112. The use of any one of embodiments 74-111, wherein the VL of the scFv comprises a HVR-L1 comprising the amino acid sequence of SEQ ID NO:16; a HVR-L2 comprising the amino acid sequence of SEQ ID NO:17; and a HVR-L3 comprising the amino acid sequence of SEQ ID NO:18.

113. The use of any one of embodiments 74-112, wherein the VH of the scFv comprises an amino acid sequence having at least about 85% (such as about 100%) sequence identity to the amino acid sequence of SEQ ID NO: 19.

114. The use of any one of embodiments 74-113, wherein the VL of the scFv comprises an amino acid sequence having at least about 85% (such as about 100%) sequence identity to the amino acid sequence of SEQ ID NO: 20.

115. The use of embodiment 114, wherein the scFv comprises an amino acid sequence having at least about 85% (such as about 100%) sequence identity to the amino acid sequence of SEQ ID NO:21.

116. The use of any one of embodiments 73-115, wherein the multispecific Fab fusion protein comprises a first polypeptide comprising an amino acid sequence having at least about 85% (such as about 100%) sequence identity to the amino acid sequence of SEQ ID NO:22.

117. The use of any one of embodiments 73-116, wherein the multispecific Fab fusion protein comprises a second polypeptide comprising an amino acid sequence having at least about 85% (such as about 100%) sequence identity to the amino acid sequence of SEQ ID NO:23.

EXAMPLES

The examples below are intended to be purely exemplary of the invention and should therefore not be considered to limit the invention in any way. The following examples and detailed description are offered by way of illustration and not by way of limitation. For the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

Example 1: Expression and Purification of an Exemplary Bispecific Fab Fusion Protein 1. Transient Expression Fab fragments or Fab fusion proteins were expressed using standard protocols. DNA fragments encoding the light chain and the heavy chain of the Fab fusion protein were cloned into expression vector pcDNA to generate constructs expressing the light chain and the heavy chain. The constructs also contained sequences encoding signal peptides in order to facilitate secretion of the light chain and heavy chain proteins. Sequencing results indicated correct gene insertion. The constructs were transformed into E. coli to obtain transfection-grade plasmid DNA. HEK293F cells were grown in EXPI293™ expression medium (Invitrogen). For transfection, 10 mL of medium containing plasmid DNA and 25 kD Polyethylenimine (PEI; DNA/linear 25 kD PEI weight ratio of 1:3) was added to 90 mL of cell culture. Transfected cells were cultured in a $CO_2$ incubator (37° C., 5% $CO_2$, 125 rpm) for about 6 days, then the supernatant was collected.

2. Stable Expression

DNA fragments (SEQ ID NO:32) encoding the light chain of an exemplary EpCAM×CD3 Fab fusion protein (referred hereinafter as ITAB1002) was cloned into the expression vector carrying a hygromycin resistance gene. DNA fragments (SEQ ID NO:31) encoding the heavy chain of the EpCAM×CD3 Fab fusion protein was cloned into the expression vector carrying a puromycin resistance gene. The DNA fragments encoding the light and heavy chains of the Fab fusion protein also each comprised a Kozak sequence and a signal peptide sequence (amino acid sequence is shown as SEQ ID NO: 33, nucleic acid sequence is shown as SEQ ID NO: 34), and were cloned in between HindIII and NotI restriction enzyme sites to generate constructs expressing the light chain and heavy chain, respectively. 40 μg of DNA plasmids carrying the heavy chain gene or the light chain gene, respectively, were transfected via electroporation (MaxCyte) into CHO—S suspension cells in logarithmic growth phase, when cell numbers were ~8×10$^8$. Cells were counted after 24 h. Transfected cells were then seeded with a density of about 1.5×10$^6$ cells/mL in CD OptiCHO Medium (Invitrogen) containing 5 μg/mL puromycin (Invitrogen) and 200 μg/mL hygromycin B (HyClone), and cultured in a $CO_2$ incubator (37° C., 5% $CO_2$, 125 rpm). Fresh media were replaced every 2-3 days until the transfected cells resumed normal growth rate, then cells in logarithmic growth phase were collected, stably transfected cell populations were stored, and single-cell clones were obtained by limiting dilution. Stably transfected cell populations were cultured in CD OptiCHO Medium (Invitrogen) supplemented with 1× glutamic acid and 1 g/L PF68 (37° C., 5% $CO_2$, 125 rpm). When cell density reached at least 3×10$^6$ cells/mL, cells were transferred to 32° C. incubation (HF511 2.5%, HF502 0.2%, MednaBio), and media were changed every 2 days. After 2-4 times of media change, the supernatant was collected.

Figure 2A:
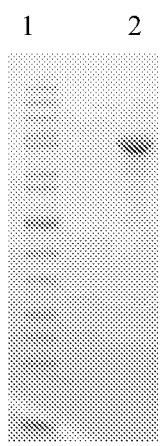
FIG. 2A depicts an SDS-PAGE gel of a purified exemplary EpCAM×CD3 Fab fusion protein (referred herein after as ITAB1002) under non-reducing conditions. The non-reducing SDS-PAGE shows a molecular weight of about 100 kD for the purified protein, similar to the theoretical molecular weight of the EpCAM×CD3 Fab fusion protein.
Figure 2B:
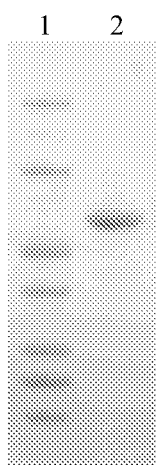
FIG. 2B depicts an SDS-PAGE gel of purified ITAB1002 under reducing conditions. The reducing SDS-PAGE shows that the apparent molecular weight of the purified protein is between about 45 kD and about 66 kD.
Figure 3A:
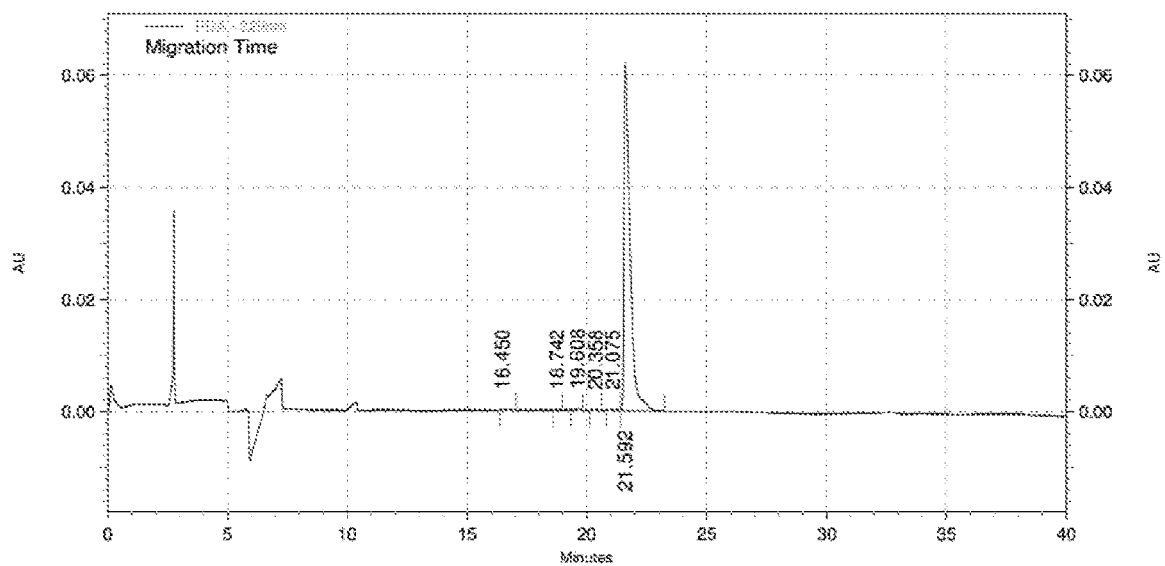
FIG. 3A depicts CE-SDS analysis results of purified ITAB1002 under non-reducing conditions. The non-reducing CE-SDS analysis shows a single protein peak at a migration time of about 21.59 min.
Figure 3B:
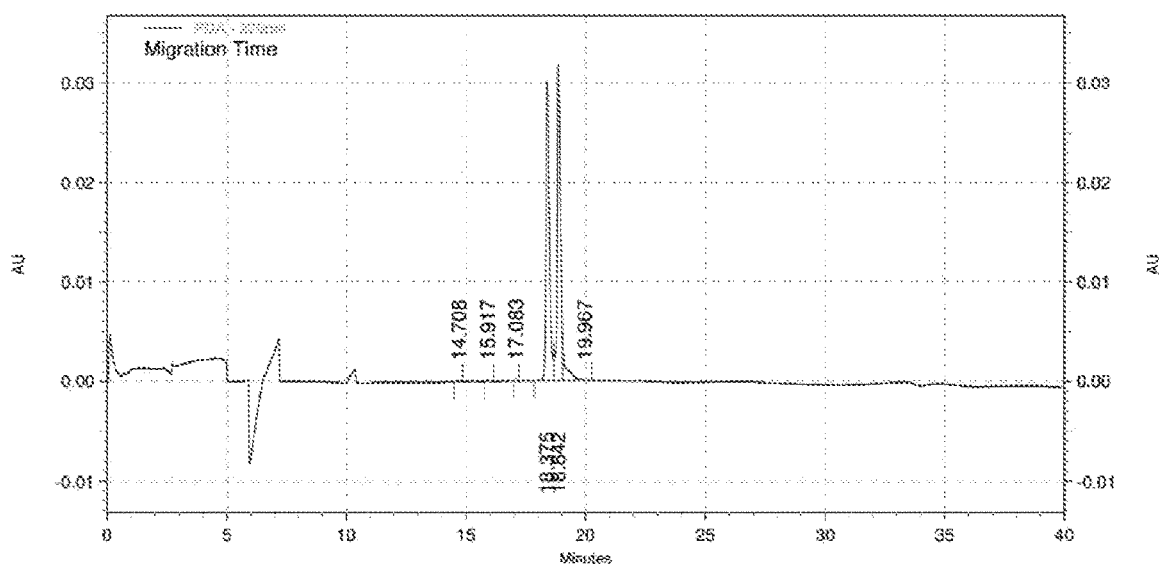
FIG. 3B depicts CE-SDS analysis results of purified ITAB1002 under reducing conditions. The reducing CE-SDS analysis shows two single protein peaks at migration times of about 18.37 min and about 18.84 min, corresponding to the light chain and the heavy chain of the Fab fusion protein, respectively.

The cell culture supernatant was purified with IgG-CH1 affinity chromatography (Thermo Fisher Scientific) to obtain target protein. The cell culture supernatant was filtered through a 0.22 μm sterile membrane, loaded onto the IgG-CH1 affinity matrix balanced with 150 mM NaCl and 10 mM phosphate buffered saline (PBS, pH 7.5), and eluted with 150 mM NaCl and 50 mM NaAc Buffer (pH 3.5). The eluate was adjusted with 2M Tris elution to a pH of 7.2, and concentrated with Vivaspin centrifugal concentrators having a 10 kD molecular weight cutoff (Sartorius). Purified protein was stored at 4° C. Protein was analyzed using 4-20% sodium dodecyl sulfate polyacrylamide gel electrophoresis (SDS-PAGE) under non-reducing and/or reducing (5% β-Mercaptoethanol) conditions. Analysis results are shown in FIGS. 2A and 2B. Non-reducing and/or reducing capillary electrophoresis (CE-SDS, Beckman Coulter, Pa. 800 plus) were performed to analyze purified Fab fusion protein, the results are shown in FIGS. 3A and 3B. HPLC analysis indicated that the purity of purified Fab fusion protein is >90%.

FIGS. 2A and 2B show the SDS-PAGE analysis results of the purified EpCAM×CD3 Fab fusion protein. FIG. 2A shows the results of non-reducing SDS-PAGE. Lane 1 contains protein molecular weight standard PAGERULER™ Unstained Protein Ladder (Thermo Scientific), with molecular weights of 200, 150, 120, 100, 85, 70, 60, 50, 40, 30, 25, 20, 15, 10 kD from top to bottom. Lane 2 contains the purified protein with a molecular weight of ~100 kD, similar to the theoretical molecular weight of EpCAM×CD3 Fab fusion protein. FIG. 2B shows the results of reducing SDS-PAGE. Lane 1 contains protein molecular weight standard PIERCE™ Unstained Protein MW Marker (Thermo Scientific), with molecular weights of 116, 66.2, 45, 35, 25, 18.4, 14.4 from top to bottom. Lane 2 contains the purified protein, the molecular weight of which is between 45-66 kD.

FIGS. 3A and 3B show results of the capillary electrophoresis (CE-SDS) of the purified EpCAM×CD3 Fab fusion protein. FIG. 3A depicts the non-reducing CE-SDS results, which show a single protein peak at migration time ~21.59 min. FIG. 3B depicts the reducing CE-SDS results, which show two single protein peaks at migration times ~18.37 min and ~18.84 min, corresponding to the light chain and heavy chain of the Fab fusion protein, respectively.

Example 2: Determination of Binding Affinities of an EpCAM×CD3 Fab Fusion Protein Antigen Binding Affinity The binding affinity of the anti-EpCAM and anti-CD3 domains in an exemplary EpCAM×CD3 Fab fusion protein (i.e., ITAB1002) with the corresponding human and cynomolgus monkey antigens were measured using Octet QK$^e$ with an anti-human IgG Fc Capture (AHC) biosensor. The human EpCAM antigen construct (huEpCAM.Fc) and the cynomolgus EpCAM antigen construct (cynoEpCAM.Fc) had a full length EpCAM protein fused to a human IgG Fc. The human CD3 antigen construct (CD3ε AA 1-27.Fc) and the cynomolgus CD3 antigen construct (cynoCD3ε AA 1-27.Fc) had a peptide consisting of amino acids 1-27 of the CD3 epsilon fused to a human IgG Fc. The expressions of the antigen constructs is described in U.S. Pat. No. 8,846,042. The antigen constructs were diluted to 0.02 mg/mL with dilution (PBS, 0.1% BSA, 0.02% Tween-20, 0.05% NaN3), and then immobilized on an anti-hIgG Fc capture (AHC) biosensor. ITAB1002 were diluted to various concentrations, and added to a black microplate at 200 μL/well. The control wells containing only PBS were also set up. The detection results were analyzed using ForteBio Data Acquisition and ForteBio Data Analysis software.

As shown in Table 1, the anti-EpCAM and anti-CD3 domains had high in vitro binding affinities to both human and cynomolgus monkey EpCAM and CD3 constructs respectively, indicating cross-reactivity of the EpCAM×CD3 Fab fusion protein in human and cynomolgus monkeys.

TABLE 1

In vitro binding affinities(KD)

| Domain | Antigen | Kd(M) |
| --- | --- | --- |
| Anti-EpCAM | huEpCAM.Fc | $3.49 \times 10^{-9}$ |
| Anti-EpCAM | cynoEpCAM.Fc | $4.71 \times 10^{-9}$ |
| Anti-CD3 | CD3εAA 1-27.Fc | $1.26 \times 10^{-8}$ |
| Anti-CD3 | cyno CD3εAA 1-27.Fc | $1.56 \times 10^{-8}$ |

Cell Binding Affinity

The following binding assay was carried out to determine the binding affinities of an exemplary EpCAM×CD3 Fab fusion protein (i.e., ITAB1002) with cells expressing target antigens.

The binding affinity of ITAB1002 to human and cynomolgus monkey peripheral blood mononuclear cells (hPBMC or cynoPBMC) were determined using fluorescence-activated cell sorting (FACS).

hPBMC Preparation: White blood cell concentrate samples from healthy human adults were diluted with PBS buffer (Gibco), centrifuged by density gradient centrifugation (Ficoll-Paque, GE Healthcare) to obtain PBMC, washed twice with PBS, then centrifuged at room temperature, 1000 g for 10 min. Cells were collected, and resuspended in RPMI 1640 Medium (Gibco) containing 10% FBS.

cynoPBMC Preparation: Whole blood samples from cynomolgus monkeys were diluted with PBS buffer (Gibco), centrifuged by density gradient centrifugation (Ficoll-Paque, GE Healthcare) to obtain PBMC, washed twice with PBS, then centrifuged at room temperature, 1000 g for 10 min. Cells were collected, and resuspended in RPMI 1640 Medium (Gibco) containing 10% FBS.

ITAB1002 was diluted to various concentrations using a FACS buffer (PBS with 1% FBS), mixed with about $3.6 \times 10^5$ huPBMC, then incubated at room temperature for 45 min. A control group with no ITAB1002 (1% FBS/PBS+hPBMC) was also set up. Cells were washed with the FACS buffer once, resuspended in 50 μL FACS buffer, supplemented with CD4 Antibody (RFT-4g) APC-Cy7® conjugate (Invitrogen) and PE Mouse Anti-Human Light Chain X, (BD Pharmingen™), and incubated at room temperature for 45 min. 150 μL FACS buffer was finally added, and the samples were analyzed using ACCURI® C6 Cytometer (BD Biosciences). The detection results are shown in FIG. 4A.

ITAB1002 was diluted to various concentrations in 50 μL FACS buffer (PBS with 1% FBS), mixed with about $4 \times 10^5$ cynoPBMC, and then incubated at room temperature for 60 min. A negative control group with no ITAB1002 was also set up. Cells were stained with CD4 Antibody (RFT-4g) APC-Cy7® conjugate (Invitrogen) and PE Mouse Anti-Human Light Chain X, (BD Pharmingen™), and incubated at room temperature for 45 min. 150 μL FACS buffer was finally added, and the samples were analyzed using ACCURI® C6 Cytometer (BD Biosciences). The detection results are shown in FIG. 4B.

Figure 4A:
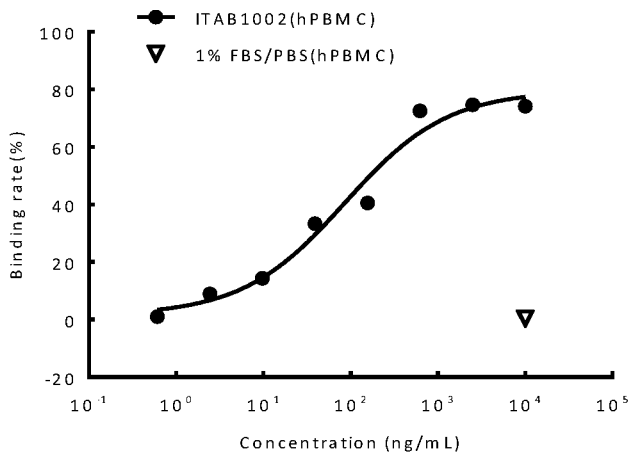
FIG. 4A depicts the binding affinity of ITAB1002 to human PBMC expressing cell surface antigen CD3.
Figure 4B:
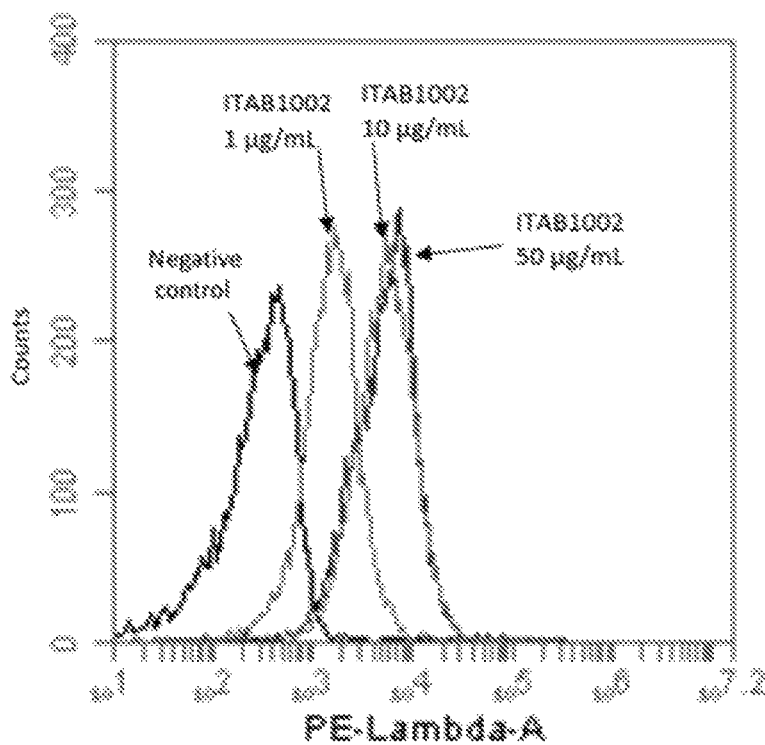
FIG. 4B depicts the binding affinity of ITAB1002 to cynomolgus monkey PBMC expressing cell surface antigen CD3.

As shown in FIGS. 4A and 4B, the EpCAM×CD3 Fab fusion protein exhibited potent binding affinity to human and cynomolgus monkey PBMC, while the negative control group had substantially no binding affinity to human or cynomolgus monkey PBMC.

Additionally, the following binding assay was performed to determine the binding affinity of the EpCAM×CD3 Fab fusion protein (i.e., ITAB1002) to EpCAM+ cells.

Human colon cancer cell line SW480 (Cell Bank, Committee on Type Culture Collection of Chinese Academy of Sciences) and Chinese hamster ovary (CHO) cells transfected with cynomolgus monkey EpCAM (hereinafter referred to as CyEpCAM-CHO) were used to determine the binding affinity of ITAB1002 with EpCAM. SW480 cells and CyEpCAM-CHO cells were trypsinized with 0.25% Trypsin-EDTA (Gibco), resuspended with a FACS buffer. ITAB1002 was diluted to various concentrations using the FACS buffer, and mixed with about $1 \times 10^5$ SW480 cells or CyEpCAM-CHO cells respectively at equal volume, followed by incubation at 4° C. for 30 min. Cells were then washed with the FACS buffer and resuspended in 50 μL FACS buffer. Mouse anti-Human IgG Fab Secondary Antibody PE conjugate (Invitrogen) were added, and allowed for incubation at 4° C. for 30 min. 150 μL FACS buffer was finally added, and the samples were analyzed using ACCURI® C6 Cytometer (BD Biosciences). The detection results are shown in FIG. 5.

Figure 5:
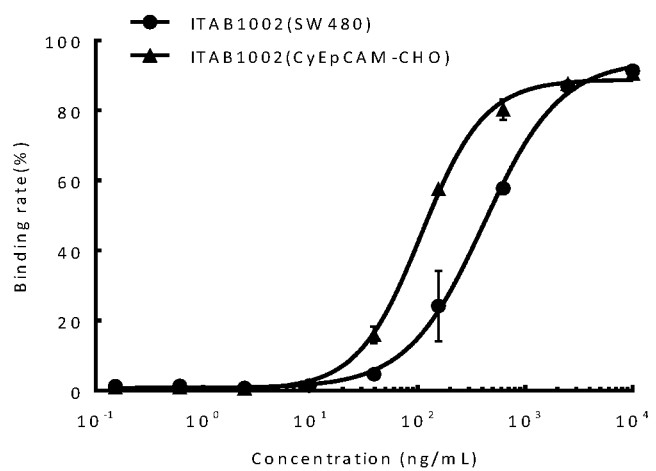
FIG. 5 depicts the binding affinity of ITAB1002 to SW480 cells and CyEpCAM-CHO cells expressing cell surface antigen EpCAM.

As shown in FIG. 5, the EpCAM×CD3 Fab fusion protein exhibited potent binding affinities to both SW480 cells expressing human EpCAM (EC50=411.2 ng/mL) and CHO cells expressing cynomolgus monkey EpCAM on the cell surface (CyEpCAM-CHO, EC50=107.6 ng/mL).

Therefore, the exemplary EpCAM×CD3 Fab fusion protein ITAB1002 exhibited cross-reactivity towards human and cynomolgus monkey antigens in vitro. The cross-reactivity of the bispecific Fab fusion protein can facilitate extrapolation of toxicity and efficacy study results in cynomolgus monkeys to human clinical studies.

Example 3: Tumor-Dependent Activation of Human PBMC by an EpCAM×CD3 Fab Fusion Protein CD4 and CD8 are typical T cell surface antigens, by which T cells can be divided into CD4+ and CD8+ subtypes. CD69 is a cell surface receptor, which is upregulated upon T cell activation. The percentage of the CD4+CD69+ and CD8+CD69+ subtypes can serve as an effective indicator of the activation status of T cells. FACS-based T cell activation assays were performed to determine the ability of an exemplary EpCAM×CD3 Fab fusion protein (i. e., ITAB1002) in T cell activation.

Human PBMC were prepared according to the method described in Example 2, and resuspended in RPMI 1640 Medium (Gibco) containing 10% FBS (Gibco). SW480 cells were trypsinized with 0.25% Trypsin-EDTA (Gibco), and resuspended in RPMI 1640 Medium containing 10% FBS. 50 4/well of cell mixture was added to each well of a 96-well plate, with a final density of 10,000 SW480 cells/well and 100,000 PBMC per well. ITAB1002 or OKT3 (Sigma) were diluted to various concentrations with RPMI 1640 Medium, and 50 μL of the diluted ITAB1002 or OKT3 was added to each well. Control wells containing no SW480 cells (PBMC+ITAB1002) were also set up. All samples were incubated for 24 hr at 37° C. Afterwards, the supernatant was discarded and cells were resuspended in 50 μL FACS buffer. Antibodies CD4 Antibody (RFT-4g) APC-Cy7® conjugate (Invitrogen), CD8 Antibody (3B5) RPE conjugate (Invitrogen) and FITC Mouse Anti-Human CD69 (BD Pharmingen™) were added to the resuspended cells, and allowed to incubate at room temperature for 30 min. 150 μL FACS buffer was added, and the samples were analyzed using ACCURI® C6 Cytometer (BD Biosciences). The detection results are shown in FIGS. 6A and 6B.

Figure 6A:
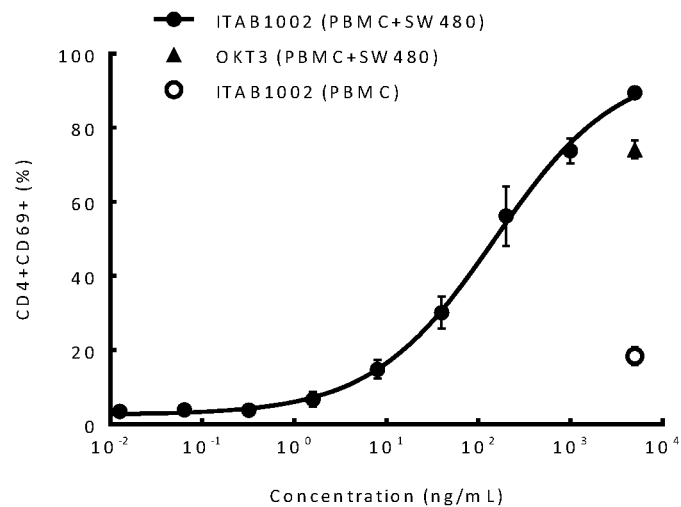
FIG. 6A shows the ability of ITAB1002 and OKT3 in activating $CD4^+$ human PBMC under various conditions.
Figure 6B:
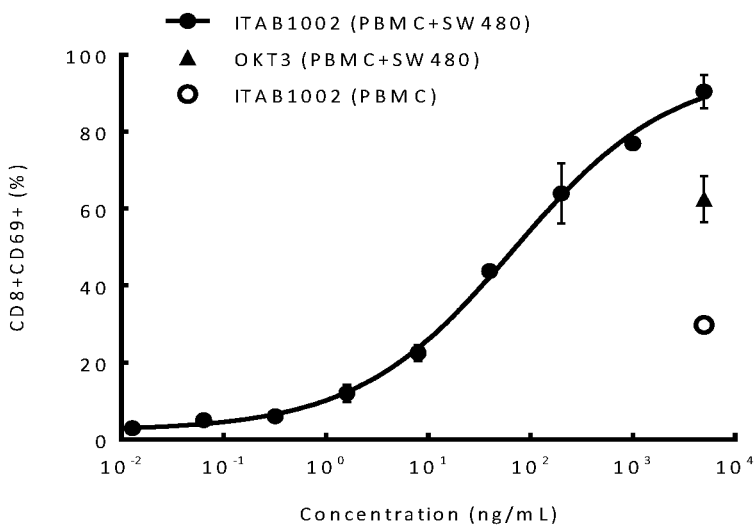
FIG. 6B shows the ability of ITAB1002 and OKT3 in activating CD8+ human PBMC under various conditions.

As shown in FIGS. 6A and 6B, in the presence of SW480 cells, the EpCAM×CD3 Fab fusion protein up-regulated CD69 expression in both $CD4^+$ and $CD8^+$ T cell populations in a dose-dependent manner (EC50=149.6 ng/mL in $CD4^+$ T cells; and EC50=68.78 ng/mL in $CD8^+$ T cells). In the absence of SW480 cells, the EpCAM×CD3 Fab fusion protein did not significantly up-regulate CD69 expression on T cells. OKT3, on the other hand, up-regulated CD69 expression in both $CD4^+$ and $CD8^+$ T cell populations.

Additionally, Ki-67 is a cell surface marker for proliferation. The percentage of the $CD4^+Ki-67^+$ subtype in the $CD4^+$ cells, and the percentage of the $CD8^+Ki-67^+$ subtype in the $CD8^+$ cells can serve as an effective indicator of the proliferation status of T cells. FACS-based T cell proliferation assays were performed to determine the ability of an exemplary EpCAM×CD3 Fab fusion protein (i.e., ITAB1002) in T cell proliferation.

Human PBMC were prepared according to the method described in Example 2, and resuspended in RPMI 1640 Medium (Gibco) containing 10% FBS (Gibco). SW480 cells were trypsinized with 0.25% Trypsin-EDTA (Gibco), and resuspended in RPMI 1640 Medium containing 10% FBS. cell mixture was added to each well of a 96-well plate, with a final density of 20,000 SW480 cells/well and 300,000 PBMC per well. ITAB1002 was diluted to various concentrations with RPMI 1640 Medium containing 10% FBS, and added to cells. Wells containing PBMC and ITAB1002 only (PBMC+ITAB1002), wells containing PBMC and SW480 cells only (PBMC+SW480), and wells containing only PBMC were set up as controls. 72 hr incubation was carried out at 37° C. Afterwards, the supernatant was discarded and cells were fixed and permeabilized in Fixation/Permeabilization Solution (BD Pharmingen) for 20 min at 4° C., and then resuspended in 50 μL BD Perm/Wash™ buffer. The cells were stained with CD4 Antibody (RFT-4g) APC-Cy7® conjugate (Invitrogen), CD8 Antibody (3B5) RPE conjugate (Invitrogen) and FITC Mouse Anti-Ki-67 Set(BD Pharmingen™) for 30 min in the dark. The samples were analyzed using ACCURI® C6 Cytometer (BD Biosciences). The detection results are shown in FIGS. 6C and 6D.

Figure 6C:
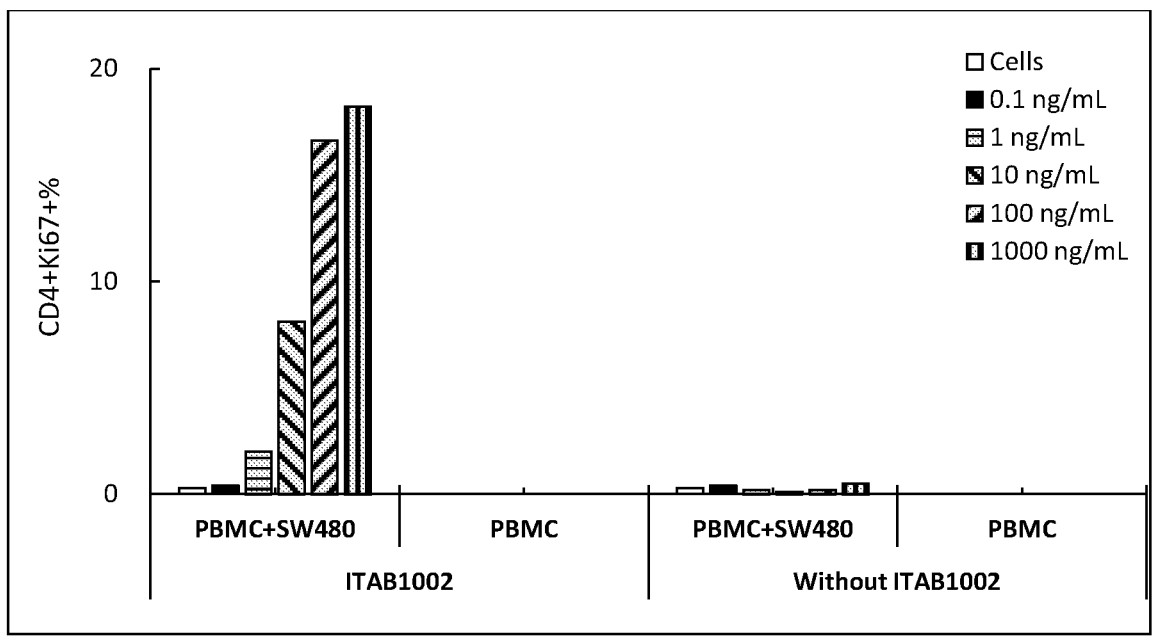
FIG. 6C shows the ability of ITAB1002 in stimulating proliferation of CD4+ human PBMC under various conditions.
Figure 6D:
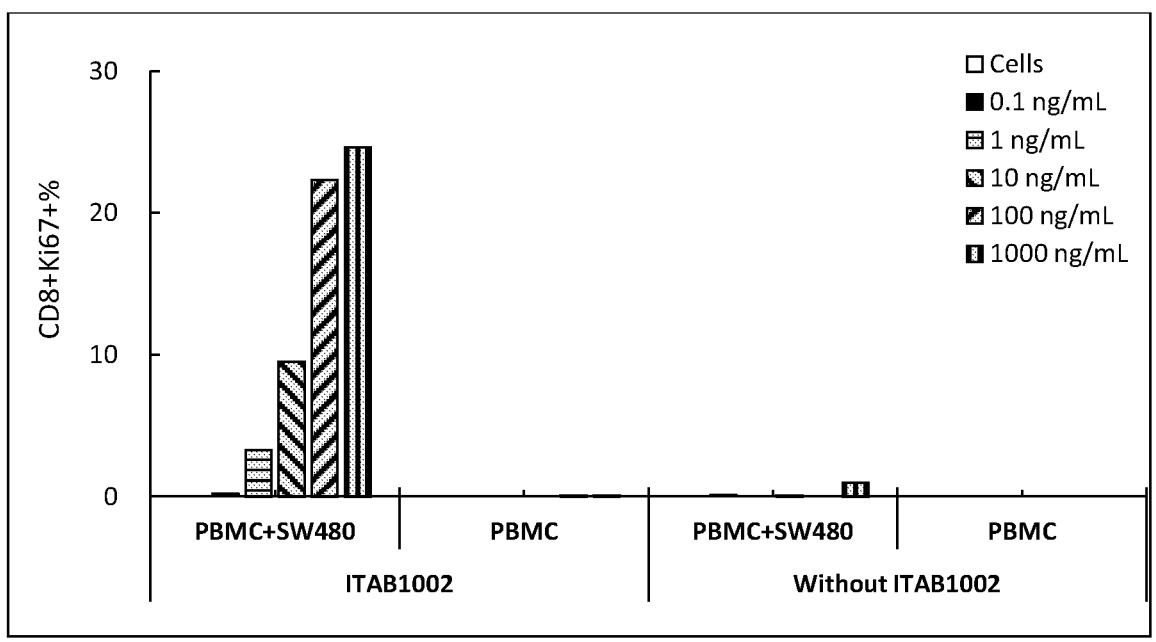
FIG. 6D shows the ability of ITAB1002 in stimulating proliferation of CD8+ human PBMC under various conditions.

As shown in FIGS. 6C and 6D, in the presence of SW480 cells, the EpCAM×CD3 Fab fusion protein up-regulated Ki-67 expression in both CD4+ and CD8+ T cell populations in a dose-dependent manner. In the absence of SW480 cells, the EpCAM×CD3 Fab fusion protein did not significantly up-regulate Ki-67 expression on T cells.

The above data demonstrates that T cells activation by the EpCAM×CD3 Fab fusion protein is specific and dependent on its tumor antigen target.

Example 4: EpCAM×CD3 Mediated PBMC Cytotoxicity Against Tumor Cells (Cytotoxicity Assays)

Human and cynomolgus monkey PBMC were prepared according to the method described in Example 2, and resuspended in RPMI 1640 Medium (Gibco) containing 10% FBS (Gibco).

SW480 cells (target cells) were trypsinized with 0.25% Trypsin-EDTA (Gibco), and resuspended in RPMI 1640 Medium containing 10% FBS. 50 4/well of cell mixture were added to each well of a 96-well plate, with a final density of 10,000 SW480 cells/well and 100,000 PBMC per well. An exemplary EpCAM×CD3 Fab fusion protein (i.e., ITAB1002) was added to cells at concentrations according to the experimental design. Wells with no drugs (PBMC+target cells), wells containing only target cells, wells containing only PBMC, and wells containing only the medium were set up as controls. About 18 hr incubation was carried out at 37° C. with 5% $CO_2$. CYTOTOX 96® Non-Radioactive Cytotoxicity Assay (Promega) was carried out to measure lactate dehydrogenase (LDH) release, and ELISA Microplate Reader (Molecular Devices, Versa Max) was used to measure OD490. The EpCAM×CD3 Fab fusion protein mediated cytotoxicity was calculated using the following formula:

$$\text{Death rate} = (OD_{sample\ well} - OD_{control\ well\ without\ drug}) / (OD_{target\ cell\ control\ well\ having\ maximum\ lysis} - OD_{target\ cell\ control\ well\ with\ spontaneous\ release}) \times 100\%$$

Figure 7:
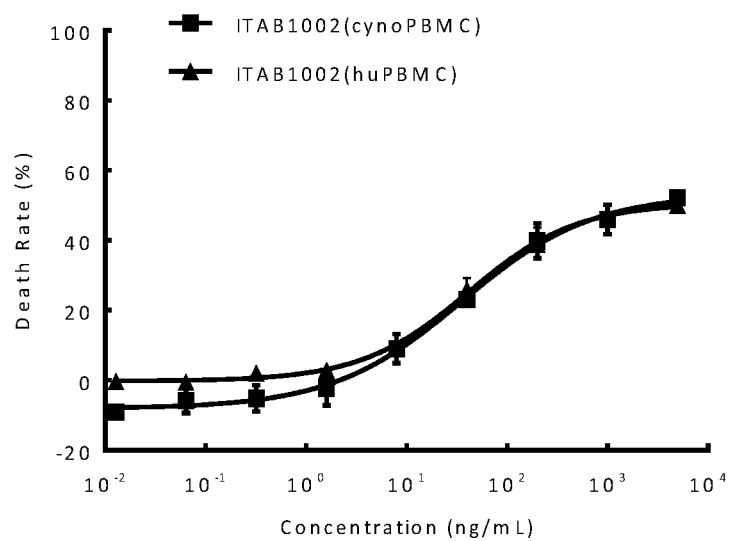
FIG. 7 depicts ITAB1002-mediated human or cynomolgus monkey PBMC cytotoxicity against SW480 tumor cells.

The GraphPad Prism 6.0 software was used for data analysis. Death rate was set as the y-axis, and drug concentration was set as the x-axis. The curves was fitted using a 4-parameter logistic model to determine EC50. The assay results are shown in FIG. 7. The EC50 of ITB1002-mediated human PBMC cytotoxicity against SW480 cells was 41.4 ng/mL. The EC50 of ITB1002 mediated cynomolgus PBMC cytotoxicity against SW480 cells was 35.5 ng/mL.

As shown in FIG. 7, the EpCAM×CD3 Fab fusion protein could mediate cynomolgus PBMC or human PBMC to kill tumor cells, such as SW480 cells. The cytotoxicity against tumor cells was comparable for human and cynomolgus monkey PBMCs.

Example 5: EpCAM×CD3 Mediated Human PBMC Cytotoxicity Against Tumor Cells (Cytotoxicity Assays)

Human PBMC were prepared according to the method described in Example 2, and resuspended in RPMI 1640 Medium (Gibco) containing 10% FBS. Tumor cells (target cells) were trypsinized with 0.25% Trypsin-EDTA (Gibco), and resuspended in RPMI 1640 Medium containing 10% FBS. 50 μL/well of cell mixture was added to each well of a 96-well plate, with a final density of 10,000 tumor cells/well and 100,000 PBMC per well. An exemplary EpCAM×CD3 Fab fusion protein (i.e., ITAB1002) was added to cells at concentrations according to the experimental design. Wells with no drugs (PBMC+target cells), wells containing only target cells, wells containing only PBMC, and wells containing only the medium were set up as controls. About 18 hr (48 hr for H1975 and N87 cells) incubation was carried out at 37° C. with 5% $CO_2$. CYTOTOX 96® Non-Radioactive Cytotoxicity Assay (Promega) was carried out to measure LDH release, and ELISA Microplate Reader (Molecular Devices, VersaMax) was used to measure OD490.

Figure 8:
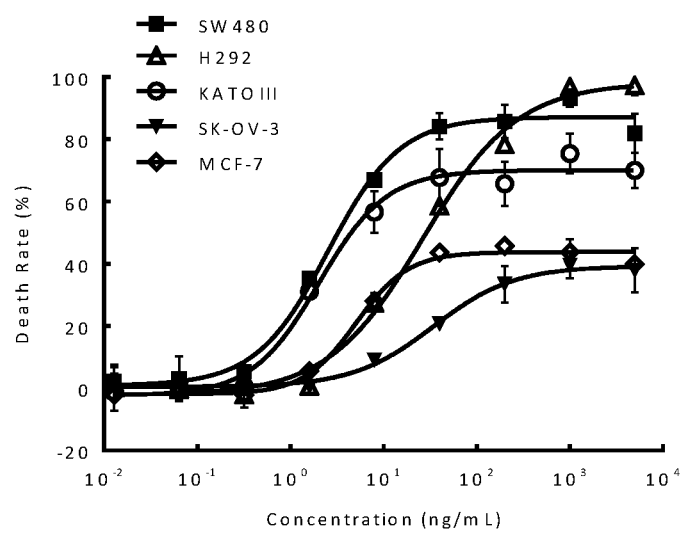
FIG. 8 depicts ITAB1002-mediated human PBMC cytotoxicity against various representative cancer cell lines.

EpCAM×CD3 Fab fusion protein mediated cytotoxicity was calculated using the following formula:

Death rate=$(OD_{sample\ well}-OD_{control\ well\ without\ drug})/(OD_{target\ cell\ control\ well\ having\ maximum\ lysis}-OD_{target\ cell\ control\ well\ with\ spontaneous\ release})\times 100\%$ The GraphPad Prism 6.0 software was used for data analysis. Death rate was set as the y-axis, and drug concentration was set as the x-axis. The curve was fitted using a 4-parameter logistic model to determine EC50. The assay results are shown in Table 2 and FIG. 8.

TABLE 2

EC50 values of EpCAM×CD3 Fab fusion protein mediated human PBMC cytotoxicity against tumor cells

| cell line name | representative cancer type | EC50 (ng/mL) |
| --- | --- | --- |
| SW480 | human colon cancer cell | 2.5 |
| MDA-MB-453 | human breast cancer cell | 12.3 |
| A549 | human lung cancer cell | >5000 |
| CFPAC-1 | human pancreatic ductal cancer cell | 53.2 |
| HT29 | human colon cancer cell | 8.1 |
| MiaPaCa | human pancreatic cancer | >5000 |
| H1975 | human lung cancer cell | 11.9 |
| HCC827 | human lung cancer cell | 15.3 |
| N87 | human gastric cancer cell | 9.9 |
| SNU-1 | human gastric cancer cell | >1000 |
| H292 | human lung cancer cell | 26.3 |
| KATOIII | human gastric cancer cell | 2.0 |
| SK-OV-3 | human ovarian cancer cell | 34.4 |
| MCF-7 | human breast cancer cell | 5.1 |
| HepG2 | human liver cancer cell | 19.6 |
| HEC-1-A | human endometrial cancer cell | 1.5 |
| OVCAR-3 | human ovarian cancer cell | 2.7 |
| RBE | human liver and bile duct carcinoma | 64.7 |
| HCCC-9810 | human intrahepatic cholangiocellular carcinoma | 191.8 |

Example 6: Efficacy Assay of an EpCAM×CD3 Fab Fusion Protein in Killing Subcutaneous Human Colon Tumor Xenograft in Immunodeficient Mice To examine the effect of an exemplary EpCAM×CD3 Fab fusion protein (i.e., ITAB1002) on inhibiting the growth of human colon tumor xenograft, in vivo drug efficacy assays were carried out on immunodeficient mice implanted with SW480 tumor cells.

Female immunodeficient mice NOD SCID (NOD.CB17-Prkdc$^{scid}$/NcrCrl) were purchased from Shanghai Lingchang Biotechnology Co., Ltd., and raised in an SPF-level animal facility.

Human colon cancer cells SW480 were cultured in vitro and collected, resuspended with serum-free L-15 Medium (Gibco) pre-cooled on ice, and placed on ice for later use. White cell concentrate donated by healthy human donors was collected, centrifuged by density gradient centrifugation (Ficoll-Paque, GE Healthcare) to obtain PBMC, resuspended in RPMI 1640 Medium (Gibco) pre-cooled on ice, and placed on ice for later use. Tumor cells and human PBMC were mixed at equal volume and inoculated subcutaneously into NOD SCID mice (about $5.0\times10^6$ SW480 cells and about $5.0\times10^6$ human PBMC per animal).

One hour after the inoculation, mice were given drugs in randomly assigned groups. Each set of 30 mice were divided into 5 groups, with 6 mice per group, designated as vehicle control group, 2.5 μg/kg ITAB1002 treatment group, 25 μg/kg ITAB1002 treatment group, 250 μg/kg ITAB1002 treatment group and Cetuximab 30 mg/kg control group, respectively. The day of inoculation and grouping was defined as D0. ITAB1002 to be tested was diluted to concentrations needed using a vehicle (PBS+0.05% Tween-80), and intravenously administered to tails of the animals at a dose of 2.5 μg/kg, 25 μg/kg and 250 μg/kg, respectively. The volume of administration was 0.1 mL/10 g body weight. The animals were administered one dose per day for 5 consecutive days (D0 to D4). Animals in the vehicle control group were administered with the same volume of the vehicle. The control drug Cetuximab (Merck Serono) was diluted to concentrations needed using the vehicle, and intravenously administered to tails of the animals at a dose of 30 mg/kg, with a volume of 0.1 mL/10 g body weight, at 2 doses per week for 3 consecutive weeks.

Meantime, control treatment groups were set up, in which animals were not inoculated with human PBMCs. NOD SCID mice were inoculated subcutaneously with about $5.0\times10^6$ SW480 tumor cells. One hour after the inoculation, the mice were randomly assigned into groups, and intravenously administered with various doses of ITAB1002 to tails of the animals, respectively.

Figure 9A:
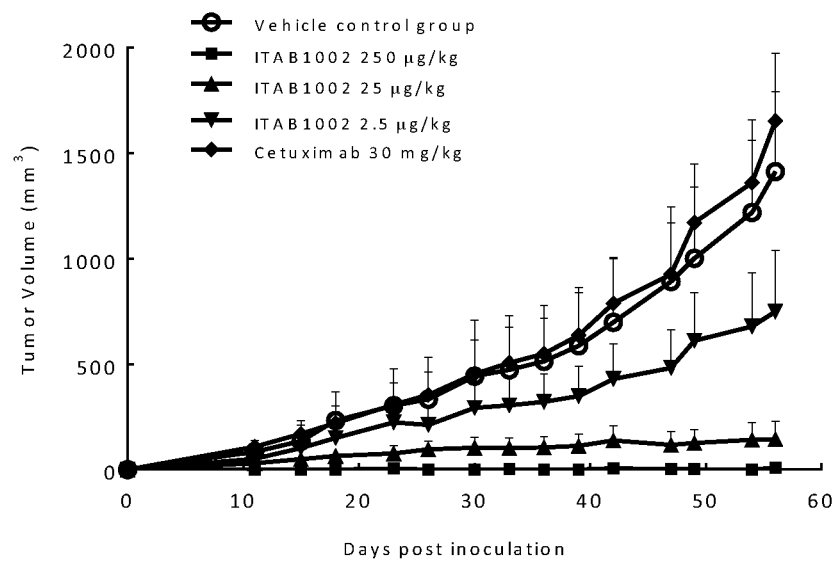
FIG. 9A depicts growth inhibitory effects of various dosages of ITAB1002 against subcutaneous SW480 xenograft in mice that were co-inoculated with human PBMC.

Body weight and tumor size of the animals were examined every week. Tumor volume was calculated according to the formula: tumor volume (mm$^3$)=length (mm)×width (mm)×width (mm)×0.5. Tumor growth inhibition rate (TGI %) was used to evaluate drug efficacy. TGI %=$[1-(avT_i-avT_0)/(avC_i-avC_0)]\times100$, wherein $avT_i-avT_0$ is the average tumor size on day i minus the average tumor size on day 0 for the treatment group, and avCi-0 is the average tumor size on day i minus the average tumor size on day 0 for the vehicle control group. The results of tumor volume assessment are shown in FIG. 9A. Pictures of the SW480 tumors isolated from the mice at the end of the experiments are shown in FIG. 9B.

Figure 9B:
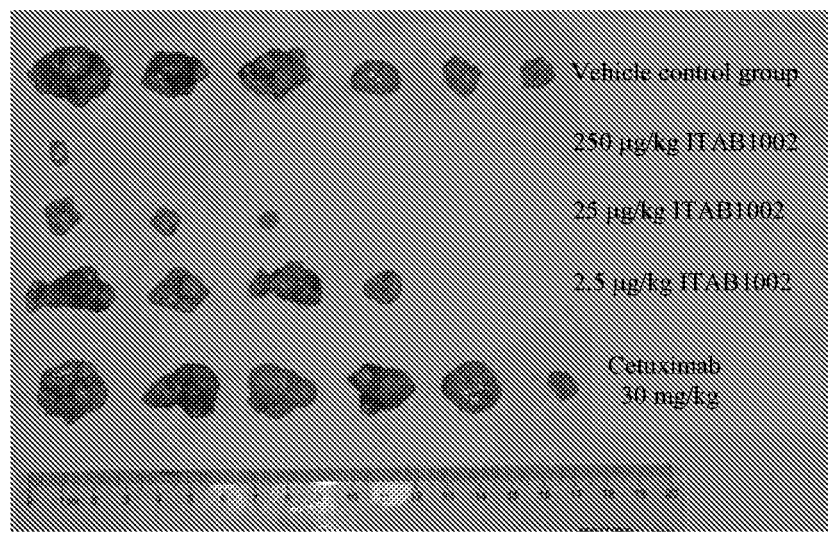
FIG. 9B shows pictures of tumors from mice in various treatment groups at the end of the experiment.

As shown in FIGS. 9A and 9B, in vehicle control group, after co-inoculation of SW480 tumor cells and human PBMC, tumor cells had normal growth, with an average tumor size of 1414.06 mm$^3$ on day 56 after inoculation. Administration of ITAB1002 effectively inhibited growth of the SW480 tumor in vivo in a dose-dependent manner. The Day 56 TGI % was 46.93%, 89.90%, and 99.35% in the 2.5 μg/kg, 25 μg/kg, and 250 μg/kg ITAB1002 treatment group, respectively. The Day 56 TGI % in the 30 mg/kg Cetuximab group was −16.97%, suggesting no inhibition of in vivo tumor growth of SW480. By contrast, without co-inoculation of the human PBMC, tumor cells had normal growth, and none of the control treatment groups showed signs of tumor regression (Data not shown). Thus, the cytotoxicity of the exemplary EpCAM×CD3 Fab fusion protein against SW480 xenograft in mice is dependent on human PBMC.

The results indicated the EpCAM X CD3 Fab fusion protein could redirect immune cells to kill tumor cells, and significantly inhibit tumor growth in vivo in a dose-dependent manner.

Example 7: Efficacy Assay of an EpCAM×CD3 Fab Fusion Protein in Killing Subcutaneous Human Colon Tumor Xenograft in an Immune-Reconstructed Mouse Model To examine the effect of an exemplary EpCAM×CD3 Fab fusion protein (i.e., ITAB1002) on inhibiting the growth of human colon tumor xenograft, in vivo drug efficacy assays were carried out on immunodeficient mice having their immune system reconstructed with human lymphocytes and implanted with SW480 tumor cells.

Female immunodeficient mice NOG (NOD.Cg-Prkek$^{scid}$Il2rg$^{tm1/Sug}$/JicCrl) were purchased from Beijing Weitong Lihua Experimental Animal Technology Co., Ltd., and raised in an SPF-level animal facility.

Experiments started after the NOG mice reached a body weight of 20 g. The mice were first treated with Busulfan (Sigma) to eradicate bone marrow cells. On the second day, in vitro cultured human colon cancer SW480 cells were collected, thoroughly mixed and resuspended with serum-free L-15 medium (Gibco) pre-cooled on ice, and were subcutaneously inoculated into NOG mice (each animal was inoculated with about $2.5 \times 10^6$ tumor cells). The day of inoculation was defined as D0. After 2 weeks, white blood cell concentrate samples donated by healthy people were collected, centrifuged by density gradient centrifugation (Ficoll-Paque, GE Healthcare) to obtain PBMC, resuspended in RPMI 1640 Medium (Gibco) pre-cooled on ice, and inoculated subcutaneously into NOG mice (each animal was inoculated with about $3.0 \times 10^6$ tumor cells). When the tumor volume reached 150-250 mm$^3$, the mice were randomly assigned to groups and administered with drugs. 40 animals were divided into 5 groups (8 animals per group), including model group, 2.5 µg/kg ITAB1002 treatment group, 25 µg/kg ITAB1002 treatment group, 250 µg/kg ITAB1002 treatment group, and 30 mg/kg Cetuximab control group.

ITAB1002 to be tested was diluted to various concentrations using a sterile filtered vehicle (PBS+0.05% Tween-80), and intraperitoneally administered in volumes of 0.1 mL/10 g body weight (corresponding to doses of 2.5 µg/kg, 25 µg/kg and 250 µg/kg, respectively) to the mice daily for 25 consecutive days. The control drug Cetuximab (Merck Serono) was diluted to concentrations needed using a sterile filtered vehicle (PBS+0.05% Tween-80), and intraperitoneally administered at a dose of 30 mg/kg to the mice twice weekly for 25 consecutive days. Animals in the model group were administered with the same volume of the vehicle.

Figure 10A:
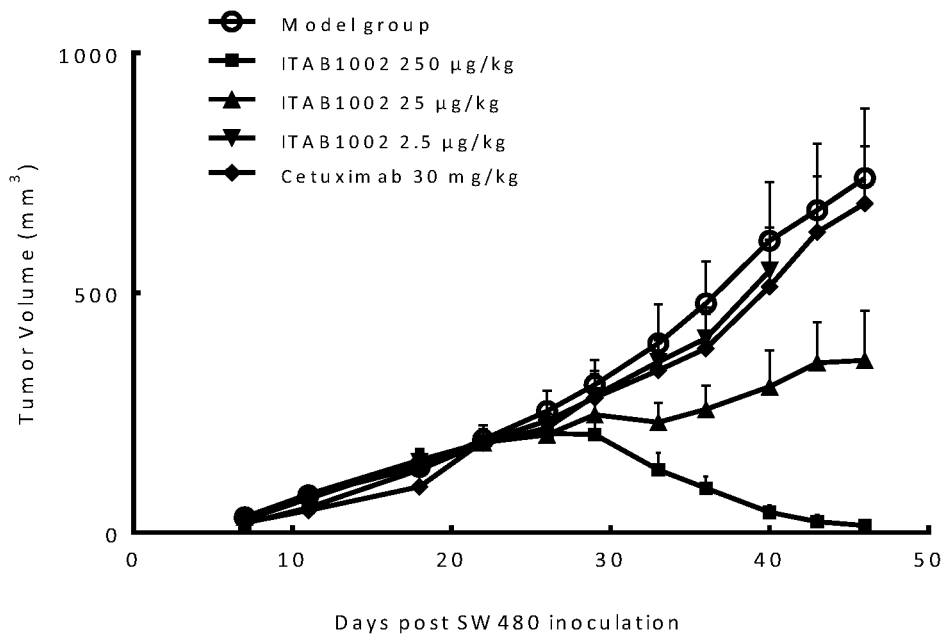
FIG. 10A depicts growth inhibitory effects of various dosages of ITAB1002 against SW480 xenograft in immunodeficient mice having their immune system reconstructed with human PBMC.
Figure 10B:
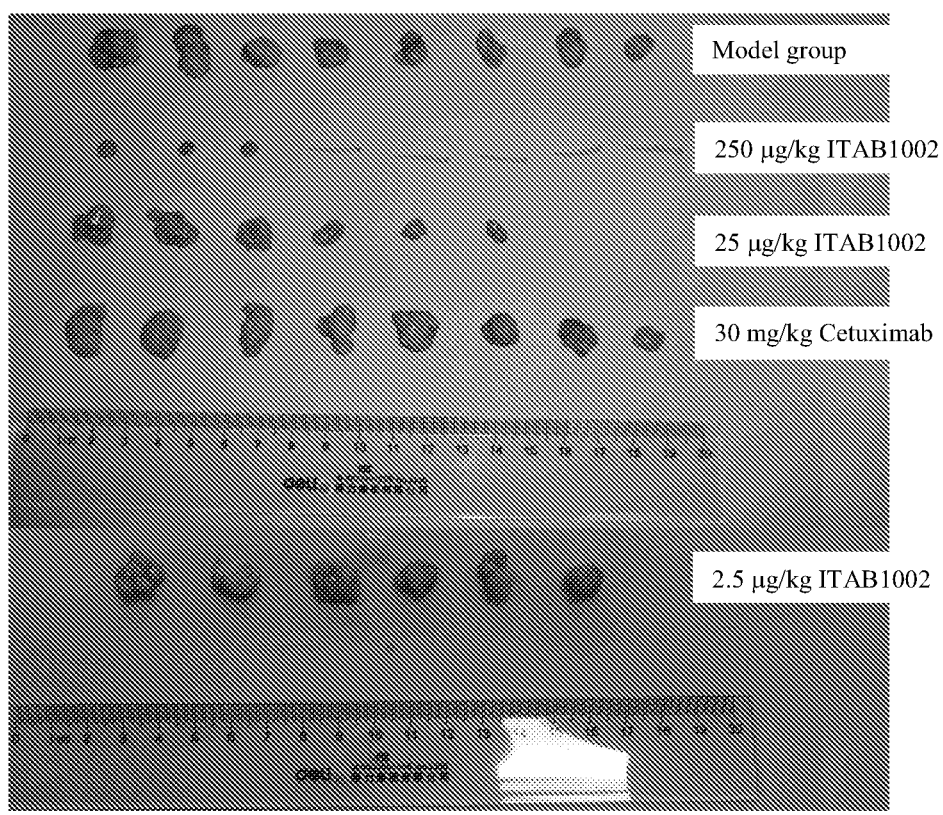
FIG. 10B shows pictures of tumors from mice in various treatment groups at the end of the experiment.

The animals were assessed weekly for body weight and tumor size. Tumor volume was calculated according to the formula: tumor volume (mm$^3$)=length (mm)×width (mm)×width (mm)×0.5. Tumor growth inhibition rate (TGI %) was used to evaluate drug efficacy. TGI %=[1−(avT$_i$−avT$_0$)/(avC$_i$−avC$_0$)]×100, wherein avT$_i$−avT$_0$ is the average tumor size on day i minus the average tumor size on day 0 for the treatment group, and avCi-0 is the average tumor size on day i minus the average tumor size on day 0 for the vehicle control group. At the end of the experiments, anticoagulated whole blood samples were collected, and stained with PE-Cy™5 Mouse Anti-Human CD3 (BD Pharmingen). The red blood cells were lysed. The percentage of human CD3$^+$ T cells in the blood samples were analyzed using FACS. FIG. 10A shows tumor volume assessment results. FIG. 10B shows pictures of SW480 tumors isolated from mice at the end of the experiments.

Figure 10C:
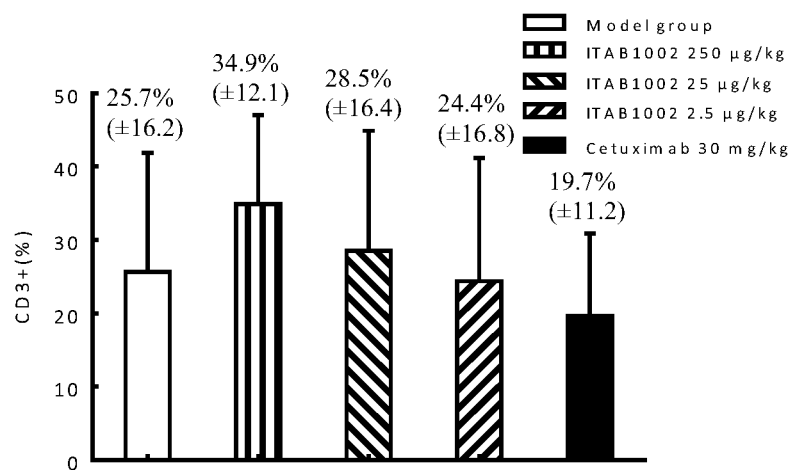
FIG. 10C show percentages of human CD3+ cells in white blood cell samples of mice at the end of the experiment.

FIGS. 10A and 10B show the growth inhibitory effect of ITAB1002 against subcutaneous SW480 xenograft tumor in immune-reconstructed NOG mice inoculated with human PBMC. The results demonstrate that tumor cells could grow normally after subcutaneous inoculation of the SW480 tumor cells into NOG mice that had been immune-reconstructed with human PBMC. After 46 days of inoculation, the average tumor volume reached 738.78 mm$^3$. Administration of ITAB1002 could effective inhibit in vivo growth of the SW480 tumor, and resulted in tumor regression. In the 2.5 µg/kg ITAB1002 treatment group, the TGI % on Day 40 was 13.29%. In the 25 µg/kg ITAB1002 treatment group, the TGI % on Day 46 was 68.55%. In the 250 µg/kg ITAB1002 treatment group, the TGI % on Day 46 was 131.65%. In the 30 mg/kg Cetuximab treatment group, Cetuximab could not inhibit in vivo growth of the SW480 tumor, and the TGI % on Day 46 was 8.91%. As shown in FIG. 10C, the average percentage of human T cells in total white blood cells of the mice was 26.84%, indicating successful reconstruction of the human T cell immune system in the NOG mice.

Therefore, after Busulfan conditioning of the bone marrow in NOG mice, and reconstruction of the immune system using human PBMC, administration of EpCAM×CD3 Fab fusion protein could effectively inhibit in vivo growth of the human colon cancer cells SW480 in mice, indicating the EpCAM X CD3 Fab fusion protein could mediate immune cells to kill tumor cells in vivo, and significantly inhibit tumor growth in a dose-dependent manner.

Example 8: Efficacy Assay of an EpCAM×CD3 Fab Fusion Protein in Killing Subcutaneous Human Lung Tumor Xenograft in an Immune-Reconstruction Mouse Model To examine the effect of an exemplary EpCAM×CD3 Fab fusion protein (i.e., ITAB1002) on inhibiting the growth of human lung tumor xenograft, in vivo drug efficacy assays were carried out on immunodeficient mice having their immune system reconstructed with human PBMC and implanted with human lung cancer tumor cells (NCI-H1975).

Female immunodeficient mice NOG (NOD.Cg-Prkdc$^{scid}$Il2rg$^{tm1/Sug}$/JicCrl) were purchased from Beijing Weitong Lihua Experimental Animal Technology Co., Ltd., and raised in an SPF-level animal facility.

Experiments started after the NOG mice reached a body weight of 20 g. The mice were first treated with Busulfan (Sigma) to eradicate bone marrow cells. On the second day, in vitro cultured human lung cancer cells NCI-H1975 were collected, thoroughly mixed and resuspended with serum-free L-15 medium (Gibco) pre-cooled on ice, and were subcutaneously inoculated into NOG mice (each animal was inoculated with about $2.5 \times 10^6$ tumor cells). The day of inoculation was defined as D0. On Day 2, white blood cell concentrate samples donated by healthy human donors were collected, centrifuged by density gradient centrifugation (Ficoll-Paque, GE Healthcare) to obtain PBMC, resuspended in RPMI 1640 Medium (Gibco) pre-cooled on ice, and inoculated subcutaneously into NOG mice (each animal was inoculated with about $3.0 \times 10^6$ PBMC, except for animals in control group). When the tumor volume reached 100-150 mm$^3$, 18 mice were randomly assigned to three groups and administered with drugs, including control group (inoculated with tumor cells, n=6), model group (inoculated with tumor cells and PBMC, n=5), and 250 µg/kg ITAB1002 treatment group (inoculated with tumor cells and PBMC, n=7).

ITAB1002 to be tested was diluted to concentrations needed using a sterile filtered vehicle (PBS+0.05% Tween-80), and intraperitoneally administered in volumes of 0.1 mL/10 g body weight (corresponding to a dose of 250 µg/kg) to the mice in the treatment group daily for 25 consecutive days. Animals in the model group and the control group were administered with the same volume of the vehicle. The animals were assessed weekly for body weight and tumor size.

Figure 11:
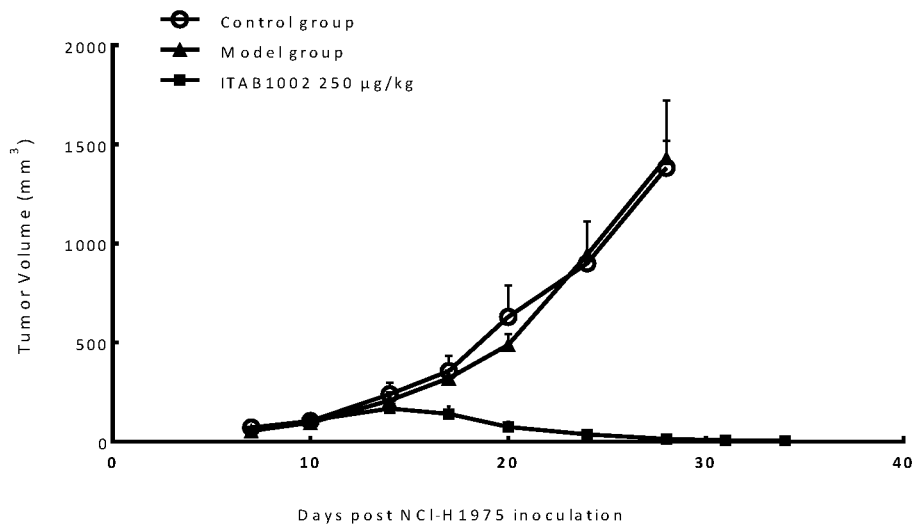
FIG. 11 depicts growth inhibitory effects of ITAB1002 against NCI-H1975 xenograft in immunodeficient mice having their immune system reconstructed with human PBMC.

FIG. 11 shows the growth inhibitory effect of ITAB1002 against subcutaneous NCI-H1975 xenograft tumor in immune-reconstructed NOG mice inoculated with human PBMC. The results demonstrate that tumor cells could grow normally in both control and vehicle groups, reaching an average tumor volume of 1382.63 mm³ and 1432.15 mm³ respectively after 28 days of inoculation. Administration of ITAB1002 at 250 μg/kg could completely inhibit in vivo growth of the NCI-H1975 tumor, and resulted in complete tumor regression. The average tumor volume on Day 34 in the 250 μg/kg ITAB1002 treatment group was 7.77 mm³.

Therefore, administration of the exemplary EpCAM× CD3 Fab fusion protein could effectively inhibit in vivo growth of the human lung cancer cells NCI-H1975 in NOG mice that had been immune-reconstructed with human PBMC, indicating the EpCAM X CD3 Fab fusion protein could mediate immune cells to kill tumor cells, and significantly inhibit the tumor growth in vivo.

Example 9: Induced T Cell Redistribution, Cytokine Release and Pharmacokinetics of an EpCAM×CD3 Fab Fusion Protein in Cynomolgus Monkeys Cynomolgus monkeys (regular grade), age: 3-5, body weight: 3.0-5.0 kg. 16 cynomolgus monkeys were divided into four groups for administration of an exemplary EpCAM×CD3 Fab fusion protein (i.e., ITAB1002), designated as 0.5 μg/kg dosage group (n=3), 5 μg/kg dosage group (n=4), 15 μg/kg dosage group (n=6) and 50 μg/kg dosage group (n=3) respectively.

ITAB1002 to be tested was diluted with vehicle (PBS+ 0.5% monkey serum) to various concentrations, and was administered at a volume of 2.0 mL/kg body weight. ITAB1002 was administered with a dosage of 0.5 μg/kg, 5 μg/kg, 15 μg/kg and 50 μg/kg, respectively, by intravenous infusion at forearms for 1 hr, single dose. Animal symptoms, behaviors, mental states, and feces, etc. were observed every day.

Whole blood collection: EDTA-K2 coated VACU-TAINER® anticoagulant blood collection tubes (BD Bioscience) were used to collect 0.3 mL blood samples before drug infusion and at different time points after drug infusion. The collected anticoagulant blood samples were separated into two portions: one portion (100 μL) of the blood was analyzed for lymphocyte subtypes using automated blood cell counter (Siemens, ADVIA® 2120); the other portion (200 μL) of the blood was stained for CD4 and CD8 antigens (APC Mouse Anti-Human CD4 and PE Mouse Anti-Human CD8, BD PHARMINGEN™), and subjected to analysis of the CD4+ and CD8+ lymphocyte subtypes using FACS (Beckman Coulter, Cytomics FC 500).

Serum Collection:

Non-anticoagulant blood collection tubes were also used to collect 1.2 mL blood samples before drug infusion and at different time points after drug infusion. Serum was collected after coagulation, and stored at −80° C. Non-Human Primate Th1/Th2 Cytokine Kit (BD PHARMINGEN™) was used to detect the secretion of IL-2, IL-4, IL-5, IL-6, TNF and IFN-γ cytokines in the serum. Drug concentration within the serum was measured using an enzyme-linked immunosorbent assay (ELISA). PK Solver 2.0 software was used to calculate pharmacokinetic parameters.

No death or near-death was observed in any group of monkeys during the experimental period. All groups of monkeys had normal spontaneous behaviors, good mental status, clean skin and hair. No irritation or fester was observed at the infusion areas. EpCAM x CD3 Fab fusion protein showed good safety and tolerance in cynomolgus monkeys.

Figure 12A:
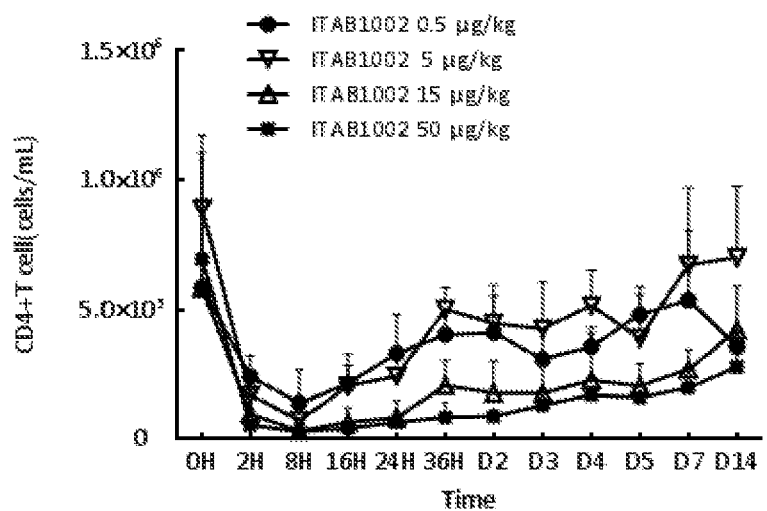
FIG. 12A depicts change of the CD4+ T cell number in the blood of cynomolgus monkeys over time after intravenous administration of ITAB1002 at various dosages. X-axis: H=hours; D=days.

FIG. 12A shows a plot of change in the number of CD4+ T cells over time in the blood of cynomolgus monkeys after single intravenous administration of the EpCAM×CD3 Fab fusion protein at various dosages ("H" is hour and "D" is day on the x-axis). After drug administration, the number of CD4+ T cells in the blood decreased, with the lowest cell number observed 8 hours post drug infusion, then cell number started to gradually recover.

Figure 12B:
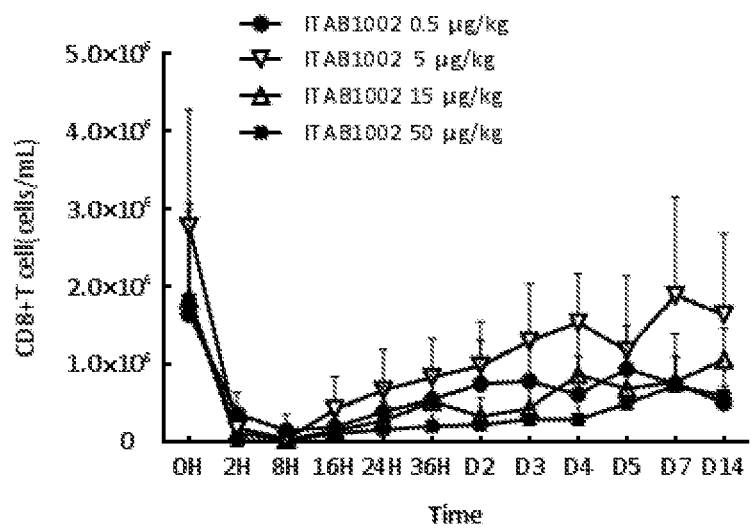
FIG. 12B depicts change of the CD8+ T cell number in the blood of cynomolgus monkeys over time after intravenous administration of ITAB1002 at various dosages. X-axis: H=hours; D=days.
Figure 13A:
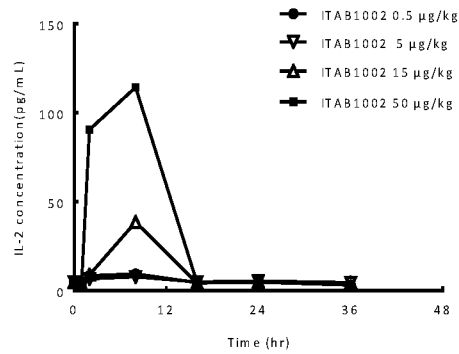
FIG. 13A depicts change of the concentration of IL-2 in the serum of cynomolgus monkeys over time after intravenous administration of ITAB1002 at various dosages.
Figure 13B:
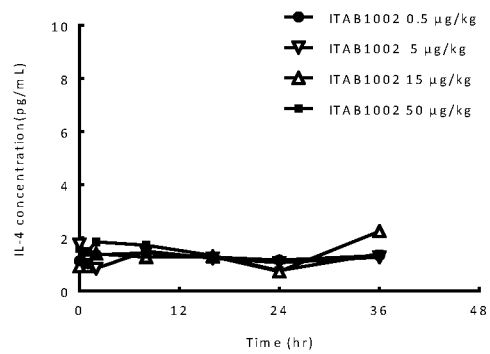
FIG. 13B depicts change of the concentration of IL-4 in the serum of cynomolgus monkeys over time after intravenous administration of ITAB1002 at various dosages.
Figure 13C:
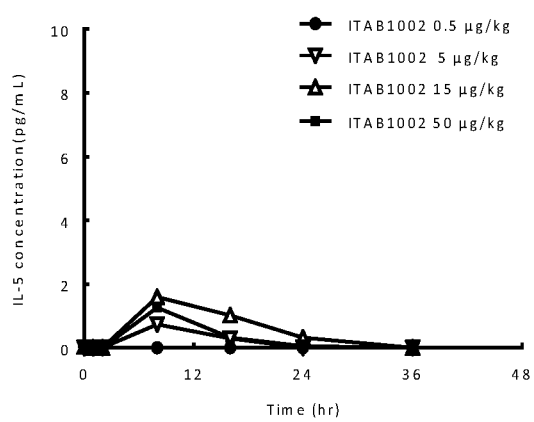
FIG. 13C depicts change of the concentration of IL-5 in the serum of cynomolgus monkeys over time after intravenous administration of ITAB1002 at various dosages.
Figure 13D:
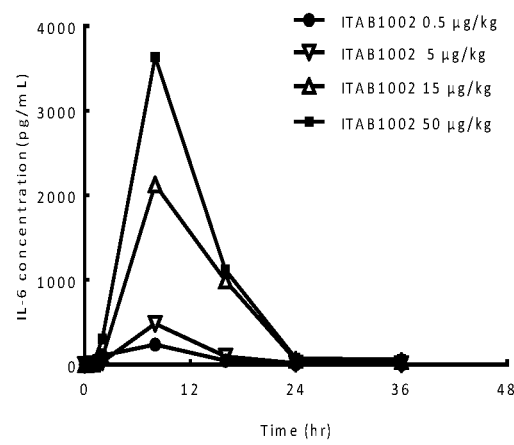
FIG. 13D depicts change of the concentration of IL-6 in the serum of cynomolgus monkeys over time after intravenous administration of ITAB1002 at various dosages.
Figure 13E:
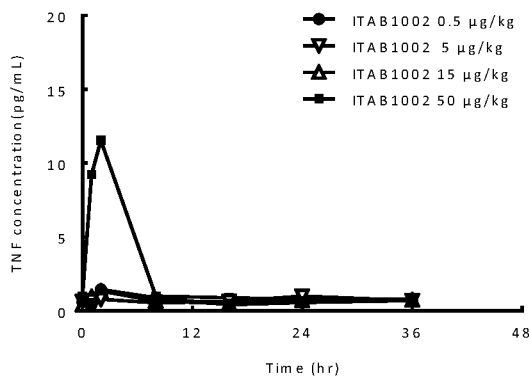
FIG. 13E depicts change of the concentration of TNF in the serum of cynomolgus monkeys over time after intravenous administration of ITAB1002 at various dosages.
Figure 13F:
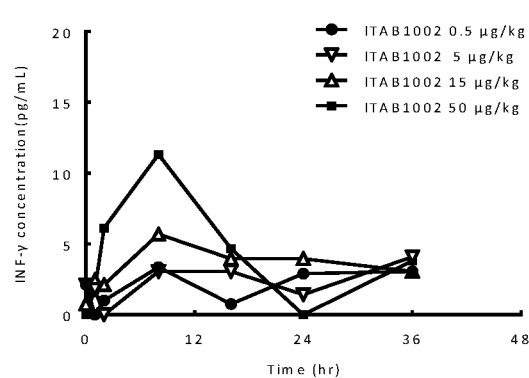
FIG. 13F depicts change of the concentration of IFN-γ in the serum of cynomolgus monkeys over time after intravenous administration of ITAB1002 at various dosages.

FIG. 12B shows a plot of change in the number of CD8+ T cells over time in the blood of cynomolgus monkeys after single intravenous administration of the EpCAM×CD3 Fab fusion protein at various dosages ("H" is hour and "D" is day on the x-axis). After drug administration, the number of CD8+ T cells in the blood decreased, with the lowest cell number observed 8 hours post drug infusion, then cell number started to gradually recover.

FIGS. 13A-13F shows change of the concentration of IL-2 (FIG. 13A), IL-4 (FIG. 13B), IL-5 (FIG. 13C), IL-6 (FIG. 13D), TNF (FIG. 13E) and IFN-γ (FIG. 13F) over time in the serum of cynomolgus monkeys after single intravenous administration of the EpCAM×CD3 Fab fusion protein at various dosages. The results indicated that after the single intravenous administration of the EpCAM×CD3 Fab fusion protein, the serum concentrations of IL-2, IL-6, TNF and IFN-γ increased to different extents, then decreased back to baseline level after reaching a peak concentration, and exhibited a dose-dependent relationship, while the serum concentrations of IL-4 and IL-5 did not change significantly.

Figure 14:
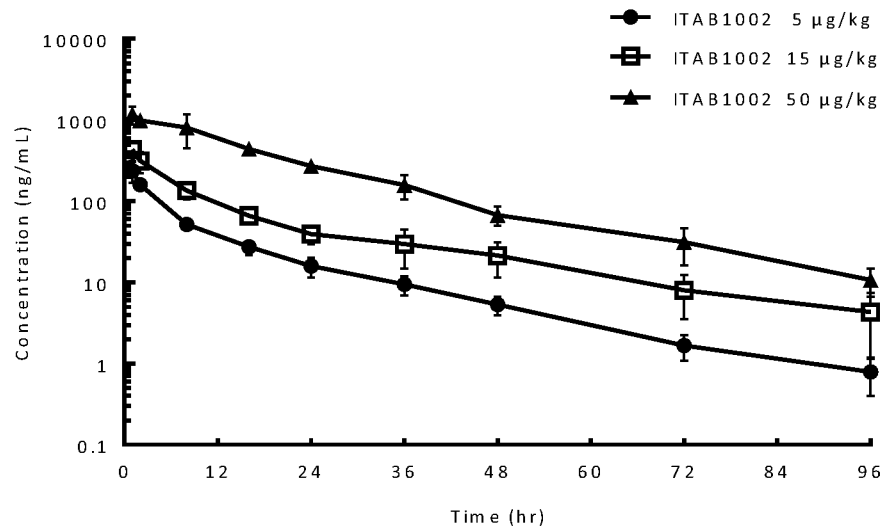
FIG. 14 depicts change of the concentration of ITAB1002 in the serum of cynomolgus monkeys after a single intravenous administration of ITAB1002 at various dosages.

FIG. 14 depicts the change of drug concentration over time in the serum of cynomolgus monkeys after single intravenous administration of the EpCAM×CD3 Fab fusion protein at various dosages.

The results indicated that for all three dosage groups (5 μg/kg, 15 μg/kg and 50 μg/kg), the serum concentration of drug reached a peak level after 1 hour of single intravenous administration of the EpCAM×CD3 Fab fusion protein, then gradually decreased. The EpCAM×CD3 Fab fusion protein exhibited increased in vivo half-life in cynomolgus monkeys.

Detailed pharmacokinetic parameters of the EpCAM× CD3 fusion protein are shown in Table 3

TABLE 3

In vivo pharmacokinetic parameters of the exemplary EpCAM×CD3 Fab fusion protein in cynomolgus monkeys (Mean ± SD)

| Dose | $t_{1/2}$ (hr) | $C_{max}$ (ng/mL) | AUC 0-t (ng/mL * hr) | MRT 0-inf_obs (hr) | Cl_obs (mL/hr/kg) |
|---|---|---|---|---|---|
| ITAB1002 5 μg/kg | 15.8 ± 0.9 | 237.9 ± 66.9 | 1781.6 ± 338.7 | 13.8 ± 1.0 | 2.8 ± 0.5 |
| ITAB1002 15 μg/kg | 19.5 ± 7.5 | 429.0 ± 116.2 | 4378.8 ± 937.1 | 20.4 ± 4.5 | 3.4 ± 0.8 |
| ITAB1002 50 μg/kg | 14.6 ± 2.0 | 1182.4 ± 271.5 | 20899.8 ± 4680.9 | 18.2 ± 2.0 | 2.4 ± 0.5 |

Example 10: Comparison of ITAB1002 and ITAB1012 Mediated PBMC Cytotoxicity Against Tumor Cells ITAB1012 is an EpCAMA×CD3 Fab fusion protein comprising an EpCAM scFv having different HVRs from those in the EpCAM scFv of ITAB1002. ITAB1012 was transiently expressed and purified as described in Example 1. The heavy chain of ITAB1012 has the amino acid sequence of SEQ ID NO: 35, and is encoded by the nucleic acid sequence of SEQ ID NO: 37. The light chain of ITAB1012 has the amino acid sequence of SEQ ID NO: 36, and is encoded by the nucleic acid sequence of SEQ ID No: 38. The HVRs of the EpCAM scFv fragments are underlined in the sequences below. The EpCAM scFv of ITAB1012 has previously been described in U.S. Pat. No. 8,846,042.

(ITAB1012 Heavy Chain)
SEQ ID No: 35
EVQLVESGGGLVQPGGSLRLSCAASGFTFS<u>NYWMS</u>WVRQAPGKGLEWVA<u>N
IKQDGSEKFYVDSVKG</u>RFTISRDNAKNSLYLQMNSLRAEDMAVYYCAR<u>VG
GAWELGY</u>WGQGTLVTVSAGGGGSGGGGSGGGGSGAQSVLTQPPSVSGAPG
QRVTISC<u>TGSSSNIGSYYGVH</u>WYQQLPGTAPKLLIY<u>SDTNRPS</u>GVPDRFS
GSKSGTSASLAITGLQAEDEADYYC<u>QSYDSSLSGRV</u>FGGGTKLTVLGGEV
QLVESGGGLVQPGGSLRLSCAASGFTFNTYAMNWVRQAPGKGLEWVARIR
SKYNNYATYYADSVKDRFTISRDDSKNTLYLQMNSLRAEDTAVYYCVRHG
NFGNSYVSWFAYWGQGTMVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCPPCS (ITAB1012 Light Chain)
SEQ ID No: 36
EVQLVESGGGLVQPGGSLRLSCAASGFTFS<u>NYWMS</u>WVRQAPGKGLEWVA<u>N
IKQDGSEKFYVDSVKG</u>RFTISRDNAKNSLYLQMNSLRAEDMAVYYCAR<u>VG
GAWELGY</u>WGQGTLVTVSAGGGGSGGGGSGGGGSGAQSVLTQPPSVSGAPG
QRVTISC<u>TGSSSNIGSYYGVH</u>WYQQLPGTAPKLLIY<u>SDTNRPS</u>GVPDRFS
GSKSGTSASLAITGLQAEDEADYYC<u>QSYDSSLSGRV</u>FGGGTKLTVLGGQA
VVTQEPSLTVSPGGTVTLTCRSSTGAVTTSNYANWVQQKPGQAPRGLIGG
TNKRAPGTPARFSGSLLGGKAALTLSGVQPEDEAEYYCALWYSNLWVFGG
GTKLTVLGQPKAAPSVTLFPPSSEELQANKATLVCLISDFYPGAVTVAWK
ADSSPVKAGVETTTPSKQSNNKYAASSYLSLTPEQWKSHRSYSCQVTHEG
STVEKTVAPTECPPCS (Nucleic acid encoding ITAB1012 Heavy Chain)
SEQ ID NO: 37
gaggtgcagctggtggagtcagggggaggcttggtccagcctggggggatc
actgagactcctgtgcagcctctggattcacctttagtaattattgga
tgagctgggtccgccaggctccagggaaggggctggagtgggtggccaac
ataaagcaagatggaagtgagaaattctatgtggactctgtgaagggccg
attcaccatctccagagacaacgccaagaactcactgtatctgcaaatga
acagcctgagagccgaagacatggctgtctattactgtgcgagagtgggg
ggggcgtgggagctaggctactggggccagggaaccctggtcactgtctc
ggccggtggcggtggcagcggcggtggtgggtccggtggcggcggatctg
gcgcgcagtctgtactgactcaaccgccctcagtgtctggggcccaggg
cagagggtcaccatctcctgcactgggagcagctccaacatcggtgtctta
ttatggtgtgcactggtaccagcagcttccaggaacagcccccaaactcc
tcatctattctgacactaatcgaccctcaggggtccctgaccgattctct
ggctccaagtctggcacctcggcctccctggccatcactgggctccaggc
tgaggatgaggctgattattactgccagtcgtatgacagcagcctgagtg
gccgggtgttcggcggagggaccaagctgacagtactaggtggcgaggtg
cagctggtggagtctgggggaggcttggtacagcctggggggtccctgag
actctcctgtgcagcctctggattcaccttaacacctacgccatgaact
gggtccgccaggctccagggaaggggctggagtgggtcgcacgcataaga
agtaaatataataattatgcaacatattatgccgattcagtgaaagaccg
gttcaccatctccagagacgattccaagaacacgctgtatctgcaaatga
acagcctgagagccgaggacacggccgtatattactgtgtgagacatggg
aacttcggtaatagctacgtttcctggtttgcttactggggccaagggac
aatggtcaccgtctcttcagctagcaccaagggcccatccgtcttcccc
tggcaccctcctccaagagcacctctgggggcacagcggccctgggctgc
ctggtcaaggactacttccccgaaccggtgacggtgtcgtggaactcagg
cgccctgaccagcggcgtgcacaccttcccggctgtcctacagtcctcag
gactctactccctcagcagcgtggtgaccgtgccctccagcagcttgggc
acccagacctacatctgcaacgtgaatcacaagcccagcaacaccaaggt
ggacaagaaagttgagcccaaatcttgtccaccgtgctcatga (Nucleic acid encoding ITAB1012 Light Chain)
SEQ ID NO: 38
gaggtgcagctggtggagtcagggggaggcttggtccagcctggggggatc
actgagactcctgtgcagcctctggattcacctttagtaattattgga
tgagctgggtccgccaggctccagggaaggggctggagtgggtggccaac
ataaagcaagatggaagtgagaaattctatgtggactctgtgaagggccg
attcaccatctccagagacaacgccaagaactcactgtatctgcaaatga
acagcctgagagccgaagacatggctgtctattactgtgcgagagtgggg
ggggcgtgggagctaggctactggggccagggaaccctggtcactgtctc
ggccggtggcggtggcagcggcggtggtgggtccggtggcggcggatctg
gcgcgcagtctgtactgactcaaccgccctcagtgtctggggcccaggg
cagagggtcaccatctcctgcactgggagcagctccaacatcggtgtctta
ttatggtgtgcactggtaccagcagcttccaggaacagcccccaaactcc
tcatctattctgacactaatcgaccctcaggggtccctgaccgattctct
ggctccaagtctggcacctcggcctccctggccatcactgggctccaggc
tgaggatgaggctgattattactgccagtcgtatgacagcagcctgagtg
gccgggtgttcggcggagggaccaagctgacagtactaggtggcgaggct
gtggtgactcaggagccctcactgactgtgtccccaggagggacagtcac
tctcacctgtcgctcatccactgggctgttacaactagtaactatgcca
actgggtccagcagaaacctggacaagcacccaggggtctgattggtggt -continued

```
accaacaagcgagctccaggtaccctgcccggttctcaggctccctcct tgggggcaaagctgccctgacactgtcaggtgtgcagcctgaggacgagg ctgagtattactgcgctctatggtacagcaacctctgggtgttcggcgga gggaccaagctgaccgtccta ggccaaccgaaagcggcgcctcggtca ctctgttcccgcctcctctgaggagcttcaagccaacaaggccacactg gtgtgtctcataagtgacttctacccgggagccgtgacagtggcctggaa ggcagatagcagcccgtcaaggcgggagtggagaccaccacaccctcca aacaaagcaacaacaagtacgcggccagcagctatctgagcctgacgcct gagcagtggaagtcccacagaagctacagctgccaggtcacgcatgaagg gagcaccgtggagaagacagtggcccctacagaa tgtccaccgtgctca tga
```

Figure 15:
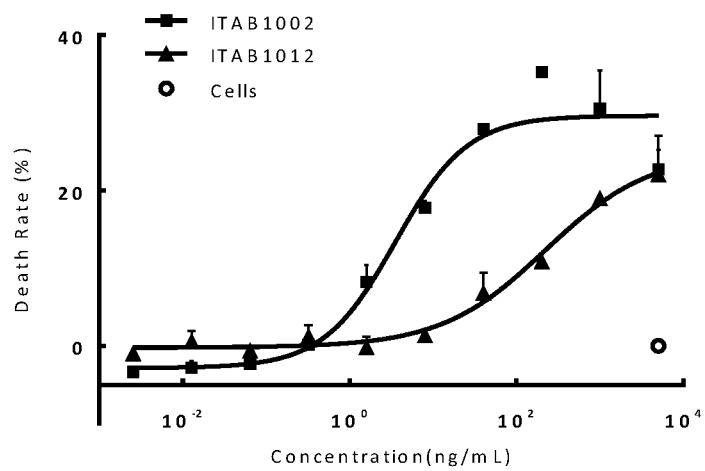
FIG. 15 compares ITAB1002 vs. ITAB1012-mediated human PBMC cytotoxicity against SW480 tumor cells.

ITAB1002 and ITAB1012 were tested in a cytotoxicity assay using human PBMC as described in Example 5. Results are shown in FIG. 15. The EC50 of ITAB1002-mediated human PBMC cytotoxicity against SW480 cells was about 3.54 ng/mL. In comparison, the EC50 of ITAB1012-mediated human PBMC cytotoxicity against SW480 cells was about 223.3 ng/mL. Thus, ITAB1002 exhibited significantly higher activity of mediating human PBMC cytotoxicity against tumor cells when compared to ITAB1012.

Additionally, the binding affinity of the anti-EpCAM and anti-CD3 domains of exemplary EpCAM×CD3 Fab fusion proteins (i.e., ITAB1002 and ITAB1012) with the human antigens were measured using the methods as described in example 2. As shown in table 4, ITAB1002 exhibited stronger binding affinity with EpCAM, while its binding affinity with CD3 is weaker when compared to ITAB1012.

TABLE 4

| | | In vitro binding affinities (KD) | | | |
|---|---|---|---|---|---|
| MSFP | Domain | Antigen | Kon (Ms$^{-1}$) | Koff (s$^{-1}$) | Kd (M) |
| ITAB1002 | Anti-EpCAM | huEpCAM.Fc | $2.00 \times 10^{+4}$ | $4.98 \times 10^{-5}$ | $2.49 \times 10^{-9}$ |
| | Anti-CD3 | CD3εAA 1-27.Fc | $8.64 \times 10^{+4}$ | $8.50 \times 10^{-4}$ | $9.84 \times 10^{-9}$ |
| ITAB1012 | Anti-EpCAM | huEpCAM.Fc | $1.35 \times 10^{+5}$ | $6.47 \times 10^{-3}$ | $4.78 \times 10^{-8}$ |
| | Anti-CD3 | CD3εAA 1-27.Fc | $8.72 \times 10^{+4}$ | $3.54 \times 10^{-5}$ | $4.05 \times 10^{-10}$ |

Example 11: EpCAM×CD3 Fab Fusion Protein Mediated Human PBMC Cytotoxicity Against Tumor Cells in the Presence of Steroid An in vitro exploratory assay was performed to assess the effect of steroid pre-treatment on the tumor cell killing activity and cytokine release by human T cells as induced by ITAB1002.

The cytotoxicity assay was performed as described in Example 5. PBMCs were isolated from healthy donors and incubated with dexamethasone (DXM) at the concentration of 3 μM for 1 hour, then added to wells of a 96-well plate, with a final density of 30,000 SW480 cells and 300,000 PBMC per well. Mixed Cells were incubated at 37° C., 5% CO2 with final concentration of DXM at 0.15 μM for about 18 hrs. Cell killing was measured by lactate dehydrogenase (LDH) assay and calculated. In the same assay, cytokine (i.e., IL-6) release was analyzed by human IL-6 ELISA Set (BD Biosciences).

Figure 16:
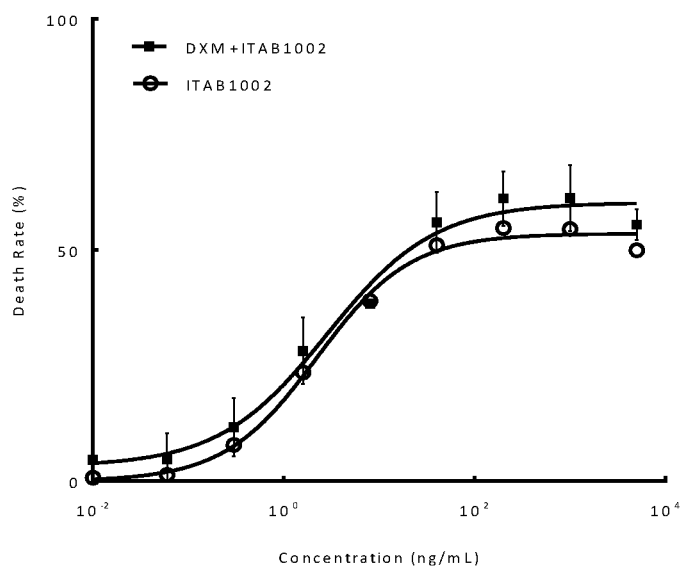
FIG. 16 depicts MSFP-mediated SW480 cell killing activity in the presence or absence of dexamethasone (DXM).

FIG. 16 shows the effect of dexamethasone (DXM) on ITAB1002-mediated SW480 cells killing activity. ITAB1002 exhibited comparable killing activity against SW480 cells in vitro in the presence of dexamethasone compared to ITAB1002 alone.

Figure 17:
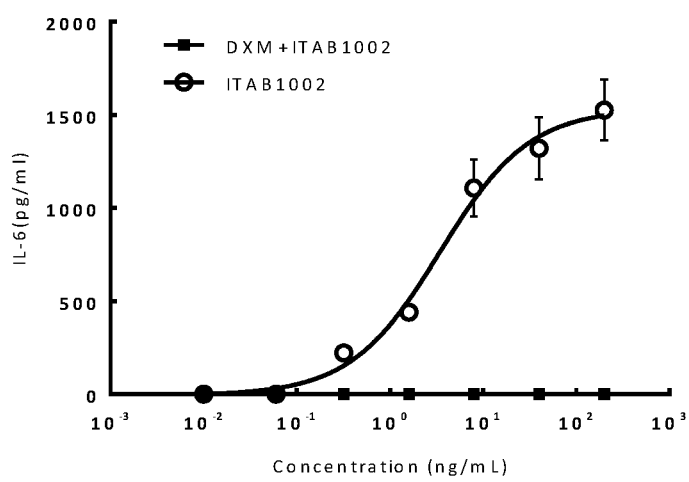
FIG. 17 depicts MSFP-mediated IL-6 release by human T cells in the presence or absence of dexamethasone (DXM).

FIG. 17 shows results from the cytokine release assay. IL-6 was released by activated T cells induced by ITAB1002. However, IL-6 release was almost completely inhibited in the presence of dexamethasone, suggesting that DXM treatment might be an effective pre-medication strategy to control cytokine release syndrome (CRS) in patients receiving ITAB1002.

Example 12: Pre-Clinical Study of EpCAM×CD3 Fab Fusion Protein in Cynomolgus Monkeys An exploratory study was conducted to evaluate the effect of dexamethasone pre-treatment on alleviating potential toxicity in cynomolgus monkeys that received ITAB1002 treatment. 6 monkeys (ITAB1002+DXM) were treated with ITAB1002 at 0.5 μg/kg twice (on day 1 and day 4) weekly via intravenous (IV) infusion during the first week. During the second week, the animals were treated with ITAB1002 at 1.0 μg/kg twice (Day 8 and Day 11) weekly by IV infusion. During the 3rd week, the animals were treated with ITAB1002 at 2.0 μg/kg twice (Day 15 and Day 18) weekly by IV infusion. During the 4$^{th}$ and 5$^{th}$ weeks, the animals were treated with ITAB1002 at 4.0 μg/kg twice (Day 22, 25, 29 and 32) weekly by IV infusion. Dexamethasone at a dose of 1 mg/kg was administered to each animal via intravenous injection (IV) about 1 hour prior to the first infusion at each dose level. Dexamethasone was increased to 2 mg/kg in week 5. In the group without DXM pre-treatment (n=10), ITAB1002 was administered to each monkey at 2.0 μg/kg via intravenously infusion twice weekly without any DXM pre-treatment. Blood samples were collected at different time points and serum chemistry parameters were analyzed. Serum IL-6 levels were analyzed by human IL-6 ELISA Set (BD Biosciences).

Figure 18A:
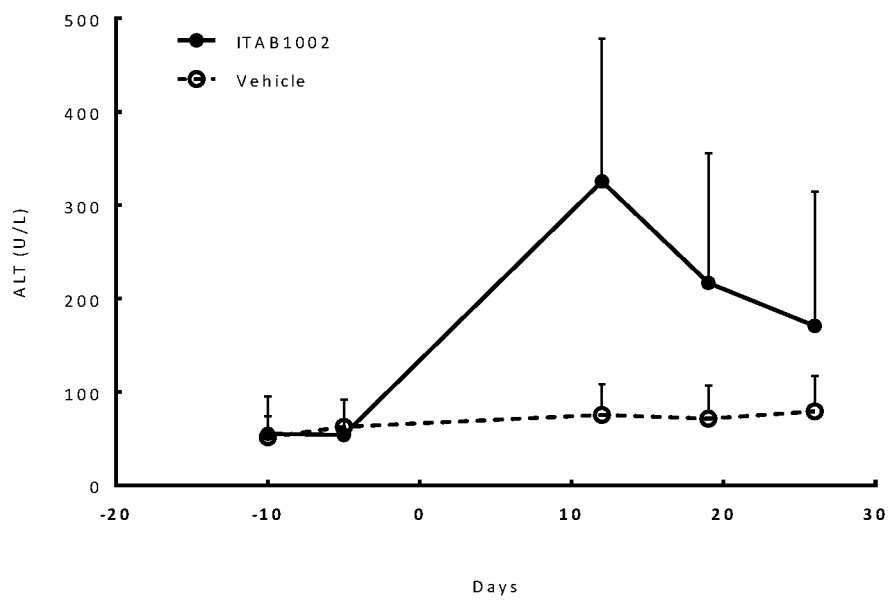
FIG. 18A shows serum levels of alanine aminotransferase (ALT) in monkeys treated with ITAB1002 only.
Figure 18B:
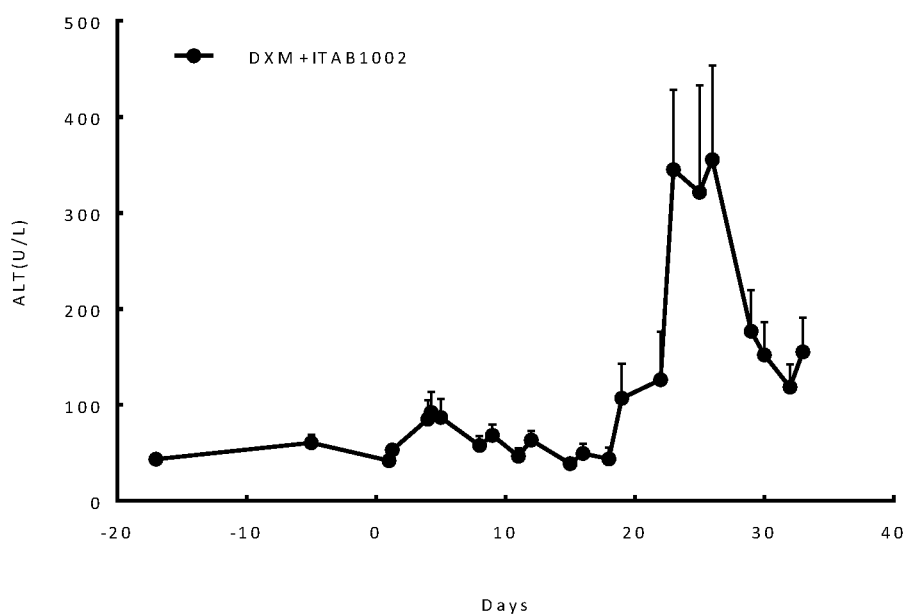
FIG. 18B shows serum levels of alanine aminotransferase (ALT) in monkeys treated with ITAB1002 with dexamethasone (DXM) pre-treatment.
Figure 19A:
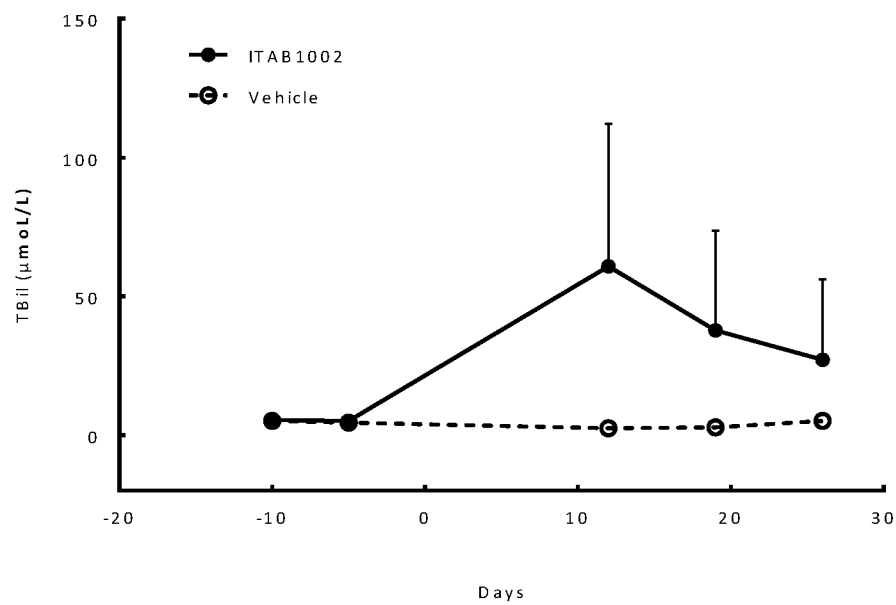
FIG. 19A shows serum levels of total bilirubin (TBil) in monkeys treated with ITAB1002 only.
Figure 19B:
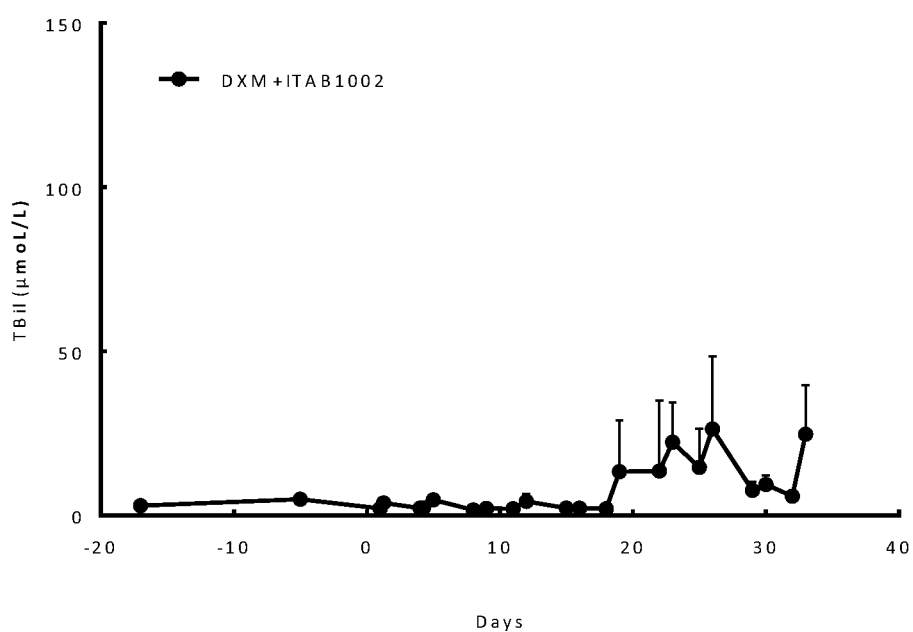
FIG. 19B shows serum levels of total bilirubin (TBil) in monkeys treated with ITAB1002 with dexamethasone (DXM) pre-treatment.
Figure 20A:
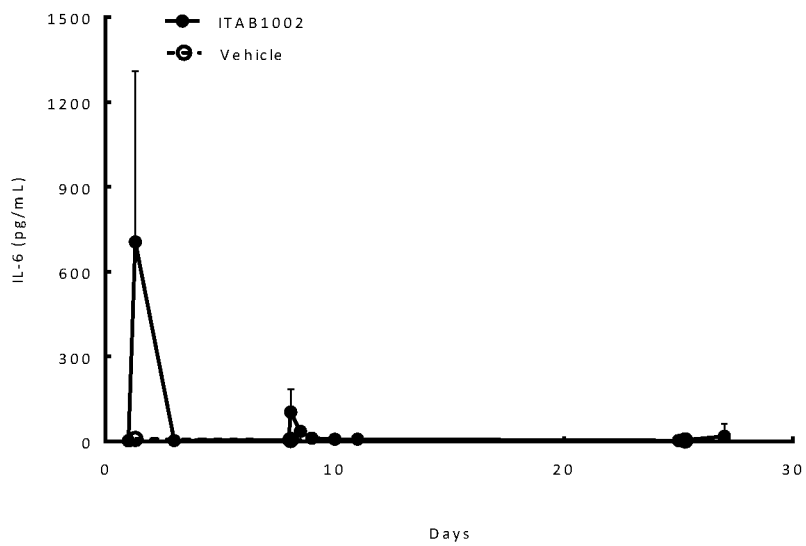
FIG. 20A shows serum levels of alkaline phosphatase (ALP) in monkeys treated with ITAB1002 only.
Figure 20B:
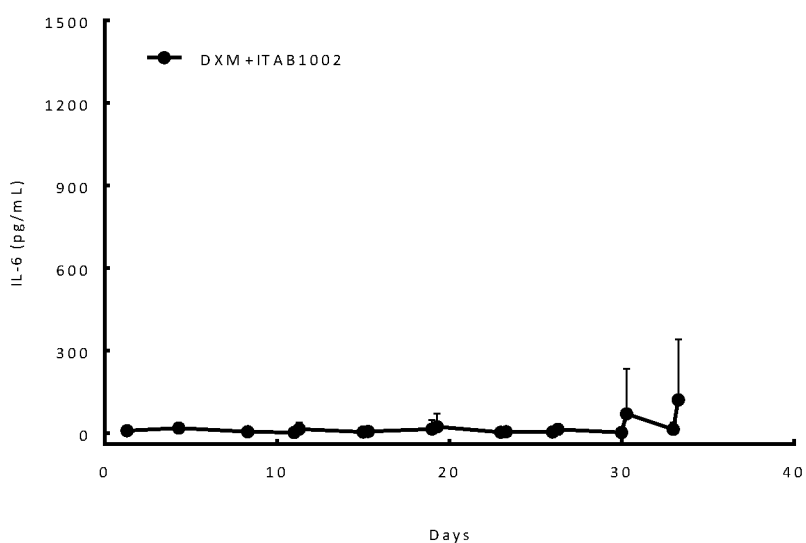
FIG. 20B shows serum levels of alkaline phosphatase (ALP) in monkeys treated with ITAB1002 with dexamethasone (DXM) pre-treatment.
Figure 21A:
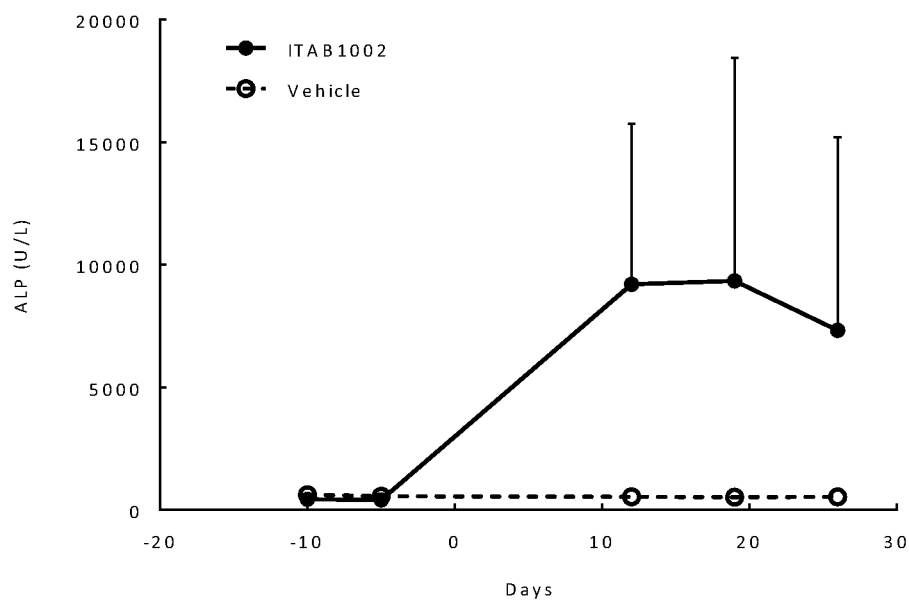
FIG. 21A shows IL-6 levels in monkeys treated with ITAB1002 only.
Figure 21B:
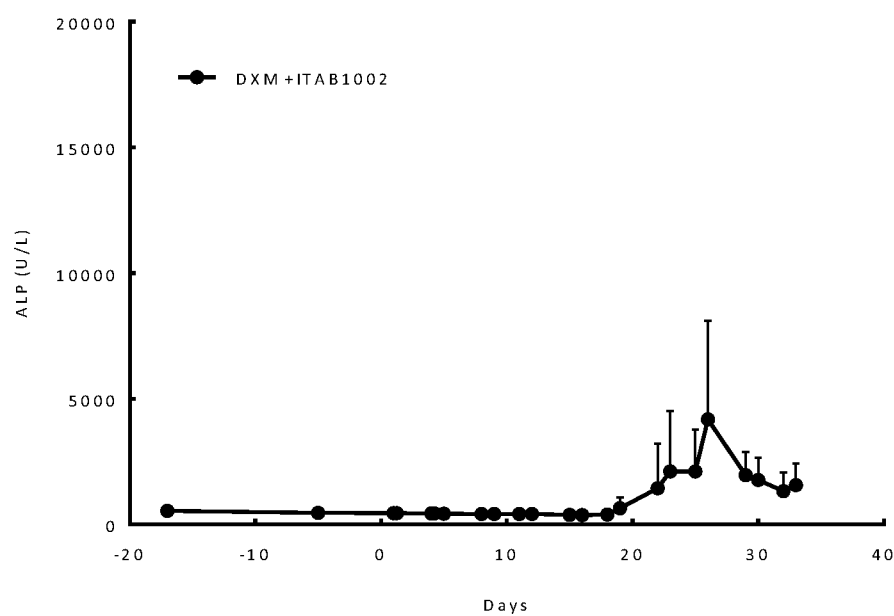
FIG. 21B shows IL-6 levels in monkeys treated with ITAB1002 with dexamethasone (DXM) pre-treatment.

Pre-treatment with DXM prior to ITAB1002 remarkably reduced the serum ALT (FIGS. 18A-18B), TBil (FIGS. 19A-19B) and ALP levels (FIGS. 20A-20B), as well as inhibited IL-6 release (FIGS. 21A-21B) when compared to treatment without DXM pre-treatment. These results demonstrated that the early induction of IL-6 release and side effects in liver in monkeys treated with ITAB1002 could be ameliorated by DXM pre-treatment.

Example 13: Clinical Testing of ITAB1002 in Human Cancer Patients

The safety and efficacy of ITAB1002 is assessed in a clinical trial in human cancer patients. The aim of the trial is to evaluate the safety, tolerability, pharmacokinetics, immunogenicity and antitumor activity of ITAB1002 in adult subjects with locally advanced or metastatic solid tumor for whom standard therapy either does not exist or has proven to be ineffective or intolerable. Five dose levels at 0.3, 0.6, 1.2, 2.4 and 3.6 µg/kg are assessed by dose escalation. The conventional 3+3 design (3 patients per dose cohort, with the potential to add 3 additional patients to the same cohort to further evaluate toxicity) are applied for dose escalation and MTD determination. 5 cohorts with about 6 patients per group are enrolled.

All patients receive a conditioning dose of 0.3 µg/kg of ITAB1002 twice (on day 1 and day 4) via intravenous (IV) infusion during the first week. In the next three weeks, patients in the 5 cohorts receive ITAB1002 twice weekly by IV infusion at the one of the following doses: 0.3 µg/kg, 0.6 µg/kg, 1.2 µg/kg, 2.4 µg/kg and 3.6 µg/kg, respectively. Dexamethasone at the dose of 20 mg is given 1 hour prior to the first conditioning dose of ITAB1002 and the first ramp-up dose (0.3 µg/kg to 3.6 µg/kg). Administration of dexamethasone prior to the subsequent doses of ITAB1002 is given at either 20 mg or 10 mg based on clinical assessment. Table 4 below shows the dosing schedule of the five cohorts in the study.

TABLE 4

Dosing schedule of human clinical trial.

| Cohort No. | Week 1 | | | Week 2 | | | Week 3 | | Week 4 | |
|---|---|---|---|---|---|---|---|---|---|---|
| | 1 hr prior | Day 1 | Day 4 | 1 hr prior | Day 1 | Day 4 | Day 1 | Day 4 | Day 1 | Day 4 |
| 1 | DXM | 0.3* | 0.3 | DXM | 0.3 | 0.3 | 0.3 | 0.3 | 0.3 | 0.3 |
| 2 | DXM | 0.3 | 0.3 | DXM | 0.6 | 0.6 | 0.6 | 0.6 | 0.6 | 0.6 |
| 3 | DXM | 0.3 | 0.3 | DXM | 1.2 | 1.2 | 1.2 | 1.2 | 1.2 | 1.2 |
| 4 | DXM | 0.3 | 0.3 | DXM | 2.4 | 2.4 | 2.4 | 2.4 | 2.4 | 2.4 |
| 5 | DXM | 0.3 | 0.3 | DXM | 3.6 | 3.6 | 3.6 | 3.6 | 3.6 | 3.6 |

*Doses of ITAB1002 are in µg/kg.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

What is claimed is:

1. An anti-EpCAM antibody or antigen-binding fragment thereof, comprising a heavy chain variable region (VH) comprising: (1) a HVR-H1 comprising the amino acid sequence of SEQ ID NO:13; (2) a HVR-H2 comprising the amino acid sequence of SEQ ID NO:14; and (3) a HVR-H3 comprising the amino acid sequence of SEQ ID NO:15; and a light chain variable region (VL) comprising: (1) a HVR-L1 comprising the amino acid sequence of SEQ ID NO:16; (2) a HVR-L2 comprising the amino acid sequence of SEQ ID NO:17; and (3) a HVR-L3 comprising the amino acid sequence of SEQ ID NO:18.

2. The anti-EpCAM antibody or antigen-binding fragment thereof according to claim 1, wherein the VH comprises the amino acid sequence of SEQ ID NO:19; and/or wherein the VL comprises the amino acid sequence of SEQ ID NO:20.

3. The anti-EpCAM antibody of claim 1, wherein the anti-EpCAM antibody is a multispecific antibody.

4. The antigen-binding fragment of the anti-EpCAM antibody of claim 1, wherein the antigen-binding fragment is a single-chain FAT (scFv).

5. The antigen-binding fragment of the anti-EpCAM antibody of claim 4, wherein the scFv comprises the amino acid sequence of SEQ ID NO:21.

6. A multispecific Fab fusion protein comprising the anti-EpCAM antigen-binding fragment of claim 1.

7. The multispecific Fab fusion protein of claim 6, comprising a Fab fragment that specifically binds to CD3, a first copy of the anti-EpCAM antigen-binding fragment, and a second copy of the anti-EpCAM antigen binding fragment; wherein the first copy of the anti-EpCAM antigen-binding fragment is fused to the N-terminus of the VH of the Fab fragment; and wherein the second copy of the anti-EpCAM antigen binding fragment is fused to the N-terminus of the VL of the Fab fragment.

8. The multispecific Fab fusion protein of claim 7, wherein the Fab fragment specifically binds to the N-terminus of CD3 epsilon.

9. The multispecific Fab fusion protein of claim 8, wherein the Fab fragment specifically binds to an epitope within amino acids 1-27 of CD3 epsilon.

10. The multispecific Fab fusion protein of claim 9, wherein the VH of the Fab fragment comprises a HVR-H1 comprising the amino acid sequence of SEQ ID NO:1; a HVR-H2 comprising the amino acid sequence of SEQ ID NO:2; and a HVR-H3 comprising the amino acid sequence of SEQ ID NO:3, and/or the VL of the Fab fragment comprises a HVR-L1 comprising the amino acid sequence of SEQ ID NO:4; a HVR-L2 comprising the amino acid sequence of SEQ ID NO:5; and a HVR-L3 comprising the amino acid sequence of SEQ ID NO:6.

11. The multispecific Fab fusion protein of claim 10, wherein the VH of the Fab fragment comprises an amino acid sequence selected from the group consisting of SEQ ID NOs:7 and 39-43, and/or wherein the VL of the Fab fragment comprises an amino acid sequence selected from the group consisting of SEQ ID NOs:8 and 44-47.

12. The multispecific Fab fusion protein of claim 7, wherein the Fab fragment comprises a human immunoglobulin heavy chain constant region 1 (CH1) comprising the amino acid sequence of SEQ ID NO:9.

13. The multispecific Fab fusion protein of claim 7, wherein the Fab fragment comprises a human lambda light chain constant region (CL) comprising the amino acid sequence of SEQ ID NO:10.

14. The multispecific Fab fusion protein of claim 7, wherein the CH1 and the CL of the Fab fragment are connected by one or more disulfide bonds.

15. The multispecific Fab fusion protein of claim 7, comprising a first polypeptide comprising the amino acid sequence of SEQ ID NO:22, and a second polypeptide comprising the amino acid sequence of SEQ ID NO:23.

16. A method of treating a cancer in an individual, comprising administering to the individual an effective amount of the multispecific Fab fusion protein of claim 7.

17. The method of claim 16, wherein the multispecific Fab fusion protein is administered intravenously.

18. The method of claim 16, wherein the cancer is selected from the group consisting of small intestine cancer, colorectal cancer, lung cancer, cervical cancer, liver cancer, gastric cancer, pancreatic cancer, skin cancer, renal cancer, bladder cancer, thyroid cancer, prostate cancer, ovarian cancer, endometrial cancer, breast cancer, bile duct cancer, and head and neck cancer.

19. The method of claim 18, wherein the cancer is colorectal adenocarcinoma.

20. The method of claim 18, wherein the cancer is lung adenocarcinoma.

\* \* \* \* \*

UNITED STATES PATENT AND TRADEMARK OFFICE
CERTIFICATE OF CORRECTION

PATENT NO. : 10,870,701 B2
APPLICATION NO. : 16/085542
DATED : December 22, 2020
INVENTOR(S) : Cui et al.

Page 1 of 1

It is certified that error appears in the above-identified patent and that said Letters Patent is hereby corrected as shown below:

On the Title Page

Item (73), should read:
Evive Biotechnology (Shanghai) Ltd

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 47

<210> SEQ ID NO 1
<211> LENGTH: 5
<212> TYPE: PRT
<213> ORGANISM: Artificial Sequence
<220> FEATURE:
<223> OTHER INFORMATION: CD3 HVR-H1

<400> SEQUENCE: 1

Thr Tyr Ala Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: CD3 HVR-H2

<400> SEQUENCE: 2

Arg Ile Arg Ser Lys Tyr Asn Asn Tyr Ala Thr Tyr Tyr Ala Asp Ser
1               5                   10                  15

Val Lys Asp

<210> SEQ ID NO 3
<211> LENGTH: 14
<212> TYPE: PRT
<213> ORGANISM: Artificial Sequence
<220> FEATURE:
<223> OTHER INFORMATION: CD3 HVR-H3
```

```
<400> SEQUENCE: 3

His Gly Asn Phe Gly Asn Ser Tyr Val Ser Trp Phe Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: CD3 HVR-L1

<400> SEQUENCE: 4

Arg Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CD3 HVR-L2

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: CD3 HVR-L3

<400> SEQUENCE: 6

Ala Leu Trp Tyr Ser Asn Leu Trp Val
1               5

<210> SEQ ID NO 7
<211> LENGTH: 125
<212> TYPE: PRT
<213> ORGANISM: Artificial Sequence
<220> FEATURE:
<223> OTHER INFORMATION: CD3 VH

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125
```

```
<210> SEQ ID NO 8
<211> LENGTH: 109
<212> TYPE: PRT
<213> ORGANISM: Artificial Sequence
<220> FEATURE:
<223> OTHER INFORMATION: CD3 VL

<400> SEQUENCE: 8
```

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

```
<210> SEQ ID NO 9
<211> LENGTH: 102
<212> TYPE: PRT
<213> ORGANISM: Homo sapiens

<400> SEQUENCE: 9
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser
            100

```
<210> SEQ ID NO 10
<211> LENGTH: 104
<212> TYPE: PRT
<213> ORGANISM: Homo sapiens

<400> SEQUENCE: 10
```

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu
            100
```

<210> SEQ ID NO 11
<211> LENGTH: 227
<212> TYPE: PRT
<213> ORGANISM: Artificial Sequence
<220> FEATURE:
<223> OTHER INFORMATION: CD3 Heavy chain

<400> SEQUENCE: 11

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser
225
```

<210> SEQ ID NO 12
<211> LENGTH: 213
<212> TYPE: PRT
<213> ORGANISM: Artificial Sequence
<220> FEATURE:
<223> OTHER INFORMATION: CD3 Light chain

<400> SEQUENCE: 12

```
Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30
```

```
Asn Tyr Ala Asn Trp Val Gln Lys Pro Gln Ala Pro Arg Gly
            35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu
    210

<210> SEQ ID NO 13
<211> LENGTH: 5
<212> TYPE: PRT
<213> ORGANISM: Artificial Sequence
<220> FEATURE:
<223> OTHER INFORMATION: EpCAM HVR-H1

<400> SEQUENCE: 13

Asn Tyr Trp Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: EpCAM HVR-H2

<400> SEQUENCE: 14

Asn Ile Lys Gln Asp Gly Ser Glu Lys Phe Tyr Ala Asp Ser Val Lys
1               5                   10                  15

Gly

<210> SEQ ID NO 15
<211> LENGTH: 9
<212> TYPE: PRT
<213> ORGANISM: Artificial Sequence
<220> FEATURE:
<223> OTHER INFORMATION: EpCAM HVR-H3

<400> SEQUENCE: 15

Val Gly Pro Ser Trp Glu Gln Asp Tyr
1               5
```

```
<210> SEQ ID NO 16
<211> LENGTH: 14
<212> TYPE: PRT
<213> ORGANISM: Artificial Sequence
<220> FEATURE:
<223> OTHER INFORMATION: EpCAM HVR-L1

<400> SEQUENCE: 16

Thr Gly Ser Ser Ser Asn Ile Gly Ser Tyr Tyr Gly Val His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: EpCAM HVR-L2

<400> SEQUENCE: 17

Ser Asp Thr Asn Arg Pro Ser
1               5

<210> SEQ ID NO 18
<211> LENGTH: 11
<212> TYPE: PRT
<213> ORGANISM: Artificial Sequence
<220> FEATURE:
<223> OTHER INFORMATION: EpCAM HVR-L3

<400> SEQUENCE: 18

Gln Ser Tyr Asp Lys Gly Phe Gly His Arg Val
1               5                   10

<210> SEQ ID NO 19
<211> LENGTH: 118
<212> TYPE: PRT
<213> ORGANISM: Artificial Sequence
<220> FEATURE:
<223> OTHER INFORMATION: EpCAM VH

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Pro Ser Trp Glu Gln Asp Tyr Trp Gly Gln Gly Thr
            100                 105                 110

Leu Val Thr Val Ser Ala
        115

<210> SEQ ID NO 20
<211> LENGTH: 113
<212> TYPE: PRT
<213> ORGANISM: Artificial Sequence
<220> FEATURE:
<223> OTHER INFORMATION: EpCAM VL
```

-continued

```
<400> SEQUENCE: 20

Gly Ala Gln Ser Val Leu Thr Gln Pro Pro Ser Val Ser Gly Ala Pro
1               5                   10                  15

Gly Gln Arg Val Thr Ile Ser Cys Thr Gly Ser Ser Ser Asn Ile Gly
            20                  25                  30

Ser Tyr Tyr Gly Val His Trp Tyr Gln Gln Leu Pro Gly Thr Ala Pro
        35                  40                  45

Lys Leu Leu Ile Tyr Ser Asp Thr Asn Arg Pro Ser Gly Val Pro Asp
    50                  55                  60

Arg Phe Ser Gly Ser Lys Ser Gly Thr Ser Ala Ser Leu Ala Ile Thr
65                  70                  75                  80

Gly Leu Gln Ala Glu Asp Glu Ala Asp Tyr Tyr Cys Gln Ser Tyr Asp
                85                  90                  95

Lys Gly Phe Gly His Arg Val Phe Gly Gly Gly Thr Lys Leu Thr Val
            100                 105                 110

Leu

<210> SEQ ID NO 21
<211> LENGTH: 246
<212> TYPE: PRT
<213> ORGANISM: Artificial Sequence
<220> FEATURE:
<223> OTHER INFORMATION: EpCAM scFv

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Pro Ser Trp Glu Gln Asp Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220
```

```
Cys Gln Ser Tyr Asp Lys Gly Phe Gly His Arg Val Phe Gly Gly
225                 230                 235                 240

Thr Lys Leu Thr Val Leu
                245

<210> SEQ ID NO 22
<211> LENGTH: 480
<212> TYPE: PRT
<213> ORGANISM: Artificial Sequence
<220> FEATURE:
<223> OTHER INFORMATION: ITAB1002 HC

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Pro Ser Trp Glu Gln Asp Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Cys Gln Ser Tyr Asp Lys Gly Phe Gly His Arg Val Phe Gly Gly Gly
225                 230                 235                 240

Thr Lys Leu Thr Val Leu Gly Gly Glu Val Gln Leu Val Glu Ser Gly
                245                 250                 255

Gly Gly Leu Val Gln Pro Gly Ser Leu Arg Leu Ser Cys Ala Ala
            260                 265                 270

Ser Gly Phe Thr Phe Asn Thr Tyr Ala Met Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Leu Tyr Leu Gln Met Asn Ser Leu
                325                 330                 335
```

Arg Ala Glu Asp Thr Ala Val Tyr Tyr Cys Val Arg His Gly Asn Phe
            340                 345                 350

Gly Asn Ser Tyr Val Ser Trp Phe Ala Tyr Trp Gly Gln Gly Thr Met
        355                 360                 365

Val Thr Val Ser Ser Ala Ser Thr Lys Gly Pro Ser Val Phe Pro Leu
    370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
    450                 455                 460

Thr Lys Val Asp Lys Lys Val Glu Pro Lys Ser Cys Pro Pro Cys Ser
465                 470                 475                 480

<210> SEQ ID NO 23
<211> LENGTH: 466
<212> TYPE: PRT
<213> ORGANISM: Artificial Sequence
<220> FEATURE:
<223> OTHER INFORMATION: ITAB1002 LC

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Pro Ser Trp Glu Gln Asp Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
                165                 170                 175

Pro Gly Thr Ala Pro Lys Leu Leu Ile Tyr Ser Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Cys Gln Ser Tyr Asp Lys Gly Phe Gly His Arg Val Phe Gly Gly Gly
225                 230                 235                 240

Thr Lys Leu Thr Val Leu Gly Gln Ala Val Val Thr Gln Glu Pro
            245                 250                 255

Ser Leu Thr Val Ser Pro Gly Gly Thr Val Thr Leu Thr Cys Arg Ser
            260                 265                 270

Ser Thr Gly Ala Val Thr Thr Ser Asn Tyr Ala Asn Trp Val Gln Gln
        275                 280                 285

Lys Pro Gly Gln Ala Pro Arg Gly Leu Ile Gly Gly Thr Asn Lys Arg
    290                 295                 300

Ala Pro Gly Thr Pro Ala Arg Phe Ser Gly Ser Leu Leu Gly Gly Lys
305                 310                 315                 320

Ala Ala Leu Thr Leu Ser Gly Val Gln Pro Glu Asp Glu Ala Glu Tyr
            325                 330                 335

Tyr Cys Ala Leu Trp Tyr Ser Asn Leu Trp Val Phe Gly Gly Gly Thr
            340                 345                 350

Lys Leu Thr Val Leu Gly Gln Pro Lys Ala Ala Pro Ser Val Thr Leu
        355                 360                 365

Phe Pro Pro Ser Ser Glu Glu Leu Gln Ala Asn Lys Ala Thr Leu Val
    370                 375                 380

Cys Leu Ile Ser Asp Phe Tyr Pro Gly Ala Val Thr Val Ala Trp Lys
385                 390                 395                 400

Ala Asp Ser Ser Pro Val Lys Ala Gly Val Glu Thr Thr Thr Pro Ser
            405                 410                 415

Lys Gln Ser Asn Asn Lys Tyr Ala Ala Ser Ser Tyr Leu Ser Leu Thr
        420                 425                 430

Pro Glu Gln Trp Lys Ser His Arg Ser Tyr Ser Cys Gln Val Thr His
    435                 440                 445

Glu Gly Ser Thr Val Glu Lys Thr Val Ala Pro Thr Glu Cys Pro Pro
450                 455                 460

Cys Ser
465

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct

<400> SEQUENCE: 24

Gly Gly Ser Gly
1

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Gly Gly Ser Gly Gly
1               5

<210> SEQ ID NO 26
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 26

Gly Ser Gly Ser Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Gly Ser Gly Gly Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Gly Gly Gly Ser Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Gly Ser Ser Ser Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Pro Leu Gly Leu Ala Gly
1               5

<210> SEQ ID NO 31
<211> LENGTH: 1443
<212> TYPE: DNA
<213> ORGANISM: Artificial Sequence
<220> FEATURE:
<223> OTHER INFORMATION: ITAB1002 HC

<400> SEQUENCE: 31
gaggtgcagc tggtggagtc agggggaggc ttggtccagc ctgggggatc cctgagactc      60
tcctgtgcag cctctggatt cacctttagt aattattgga tgagctgggt ccgccaggct     120
ccagggaagg ggctggagtg ggtggccaac ataaagcaag atggaagtga gaaattctat     180
gcggactctg tgaagggccg attcaccatc tccagagaca cgccaagaa ctcactgtat     240 ctgcaaatga acagcctgag agccgaagac acggctgtct attactgtgc gagagtgggg     300
```

```
ccgtcctggg agcaggacta ctggggccag ggaaccctgg tcactgtctc ggccggtggc      360
ggtggcagcg gcggtggtgg gtccggtggc ggcggatctg gcgcgcagtc tgtactgact      420
caaccgccct cagtgtctgg ggccccaggg cagagggtca ccatctcctg cactgggagc      480
agctccaaca tcgggtctta ttatggtgtg cactggtacc agcagcttcc aggaacagcc      540
cccaaactcc tcatctattc tgacactaat cgaccctcag gggtccctga ccgattctct      600
ggctccaagt ctggcacctc ggcctccctg gccatcactg gctccaggc tgaggatgag       660 gctgattatt actgccagtc gtatgacaag ggcttcgggc accgggtgtt cggcggaggg      720
accaagctga ccgtcctagg gggcgaggtg cagctggtgg agtctggggg aggcttggta      780
cagcctgggg ggtccctgag actctcctgt gcagcctctg gattcacctt taacacctac      840
gccatgaact gggtccgcca ggctccaggg aaggggctgg agtgggtcgc acgcataaga      900
agtaaatata ataattatgc aacatattat gccgattcag tgaaagaccg gttcaccatc      960
tccagagacg attccaagaa cacgctgtat ctgcaaatga acagcctgag agccgaggac     1020
acggccgtat attactgtgt gagacatggg aacttcggta atagctacgt ttcctggttt     1080
gcttactggg gccaagggac aatggtcacc gtctcttcag ctagcaccaa gggcccatcc     1140
gtcttccccc tggcaccctc ctccaagagc acctctgggg gcacagcggc cctgggctgc     1200
ctggtcaagg actacttccc cgaaccggtg acggtgtcgt ggaactcagg cgccctgacc     1260
agcggcgtgc acaccttccc ggctgtccta cagtcctcag gactctactc cctcagcagc     1320
gtggtgaccg tgccctccag cagcttgggc acccagacct acatctgcaa cgtgaatcac     1380
aagcccagca acaccaaggt ggacaagaaa gttgagccca atcttgtccc accgtgctca     1440
tga                                                                  1443

<210> SEQ ID NO 32
<211> LENGTH: 1401
<212> TYPE: DNA
<213> ORGANISM: Artificial Sequence
<220> FEATURE:
<223> OTHER INFORMATION: ITAB1002 LC

<400> SEQUENCE: 32
gaggtgcagc tggtggagtc agggggaggc ttggtccagc ctgggggatc cctgagactc       60
tcctgtgcag cctctggatt cacctttagt aattattgga tgagctgggt ccgccaggct      120
ccagggaagg ggctggagtg ggtggccaac ataaagcaag atggaagtga gaaattctat      180
gcggactctg tgaagggccg attcaccatc tccagagaca cgccaagaa ctcactgtat       240 ctgcaaatga acagcctgag agccgaagac acggccgtct attactgtgc gagagtgggg      300
ccgtcctggg agcaggacta ctggggccag ggaaccctgg tcactgtctc ggccggtggc      360
ggtggcagcg gcggtggtgg gtccggtggc ggcggatctg gcgcgcagtc tgtactgact      420
caaccgccct cagtgtctgg ggccccaggg cagagggtca ccatctcctg cactgggagc      480
agctccaaca tcgggtctta ttatggtgtg cactggtacc agcagcttcc aggaacagcc      540
cccaaactcc tcatctattc tgacactaat cgaccctcag gggtccctga ccgattctct      600
ggctccaagt ctggcacctc ggcctccctg gccatcactg gctccaggc tgaggatgag       660 gctgattatt actgccagtc gtatgacaag ggcttcgggc accgggtgtt cggcggaggg      720
accaagctga ccgtcctagg gggccaggct gtggtgactc aggagccctc actgactgtg      780
tccccaggag ggacagtcac tctcacctgt cgctcaagta ctgggctgt tacaactagt      840 aactatgcca actgggtcca gcagaaacct ggacaagcac ccagggtct gattggtggt      900
```

```
accaacaagc gagctccagg taccctgcc cggttctcag gctccctcct tgggggcaaa    960
gctgccctga cactgtcagg tgtgcagcct gaggacgagg ctgagtatta ctgcgctcta   1020
tggtacagca acctctgggt gttcggcgga gggaccaagc tgaccgtcct aggccaaccg   1080
aaagcggcgc cctcggtcac tctgttcccg ccctcctctg aggagcttca agccaacaag   1140
gccacactgg tgtgtctcat aagtgacttc tacccgggag ccgtgacagt ggcctggaag   1200
gcagatagca gccccgtcaa ggcgggagtg agaccacca caccctccaa acaaagcaac    1260
aacaagtacg cggccagcag ctatctgagc ctgacgcctg agcagtggaa gtcccacaga   1320
agctacagct gccaggtcac gcatgaaggg agcaccgtgg agaagacagt ggcccctaca   1380
gaatgtccac cgtgctcatg a                                             1401
```

<210> SEQ ID NO 33
<211> LENGTH: 19
<212> TYPE: PRT
<213> ORGANISM: Artificial Sequence
<220> FEATURE:
<223> OTHER INFORMATION: Signal peptide

<400> SEQUENCE: 33

```
Met Glu Trp Ser Trp Val Phe Leu Phe Phe Leu Ser Val Thr Thr Gly
1               5                   10                  15

Val His Ser
```

<210> SEQ ID NO 34
<211> LENGTH: 57
<212> TYPE: DNA
<213> ORGANISM: Artificial Sequence
<220> FEATURE:
<223> OTHER INFORMATION: Signal peptide

<400> SEQUENCE: 34

```
atggaatgga gctgggtctt tctcttcttc ctgtcagtaa cgactggtgt ccactcc        57
```

<210> SEQ ID NO 35
<211> LENGTH: 480
<212> TYPE: PRT
<213> ORGANISM: Artificial Sequence
<220> FEATURE:
<223> OTHER INFORMATION: ITAB1012 HC

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110
```

```
Leu Val Thr Val Ser Ala Gly Gly Gly Ser Gly Gly Gly Ser
            115                 120                 125
Gly Gly Gly Gly Ser Gly Ala Gln Ser Val Leu Thr Gln Pro Pro Ser
130                 135                 140
Val Ser Gly Ala Pro Gly Gln Arg Val Thr Ile Ser Cys Thr Gly Ser
145                 150                 155                 160
Ser Ser Asn Ile Gly Ser Tyr Tyr Gly Val His Trp Tyr Gln Gln Leu
                165                 170                 175
Pro Gly Thr Ala Pro Lys Leu Leu Ile Tyr Ser Asp Thr Asn Arg Pro
            180                 185                 190
Ser Gly Val Pro Asp Arg Phe Ser Gly Ser Lys Ser Gly Thr Ser Ala
        195                 200                 205
Ser Leu Ala Ile Thr Gly Leu Gln Ala Glu Asp Glu Ala Asp Tyr Tyr
    210                 215                 220
Cys Gln Ser Tyr Asp Ser Ser Leu Ser Gly Arg Val Phe Gly Gly Gly
225                 230                 235                 240
Thr Lys Leu Thr Val Leu Gly Gly Glu Val Gln Leu Val Glu Ser Gly
                245                 250                 255
Gly Gly Leu Val Gln Pro Gly Gly Ser Leu Arg Leu Ser Cys Ala Ala
            260                 265                 270
Ser Gly Phe Thr Phe Asn Thr Tyr Ala Met Asn Trp Val Arg Gln Ala
        275                 280                 285
Pro Gly Lys Gly Leu Glu Trp Val Ala Arg Ile Arg Ser Lys Tyr Asn
    290                 295                 300
Asn Tyr Ala Thr Tyr Tyr Ala Asp Ser Val Lys Asp Arg Phe Thr Ile
305                 310                 315                 320
Ser Arg Asp Asp Ser Lys Asn Thr Leu Tyr Leu Gln Met Asn Ser Leu
                325                 330                 335
Arg Ala Glu Asp Thr Ala Val Tyr Tyr Cys Val Arg His Gly Asn Phe
            340                 345                 350
Gly Asn Ser Tyr Val Ser Trp Phe Ala Tyr Trp Gly Gln Gly Thr Met
        355                 360                 365
Val Thr Val Ser Ser Ala Ser Thr Lys Gly Pro Ser Val Phe Pro Leu
    370                 375                 380
Ala Pro Ser Ser Lys Ser Thr Ser Gly Gly Thr Ala Ala Leu Gly Cys
385                 390                 395                 400
Leu Val Lys Asp Tyr Phe Pro Glu Pro Val Thr Val Ser Trp Asn Ser
                405                 410                 415
Gly Ala Leu Thr Ser Gly Val His Thr Phe Pro Ala Val Leu Gln Ser
            420                 425                 430
Ser Gly Leu Tyr Ser Leu Ser Ser Val Val Thr Val Pro Ser Ser Ser
        435                 440                 445
Leu Gly Thr Gln Thr Tyr Ile Cys Asn Val Asn His Lys Pro Ser Asn
    450                 455                 460
Thr Lys Val Asp Lys Lys Val Glu Pro Lys Ser Cys Pro Pro Cys Ser
465                 470                 475                 480

<210> SEQ ID NO 36
<211> LENGTH: 466
<212> TYPE: PRT
<213> ORGANISM: Artificial Sequence
<220> FEATURE:
<223> OTHER INFORMATION: ITAB1012 LC
```

<400> SEQUENCE: 36

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Arg Val Gly Gly Ala Trp Glu Leu Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Gln Ser Val Leu Thr Gln Pro Pro Ser
130                 135                 140

Val Ser Gly Ala Pro Gly Gln Arg Val Thr Ile Ser Cys Thr Gly Ser
145                 150                 155                 160

Ser Ser Asn Ile Gly Ser Tyr Tyr Gly Val His Trp Tyr Gln Gln Leu
            165                 170                 175

Pro Gly Thr Ala Pro Lys Leu Leu Ile Tyr Ser Asp Thr Asn Arg Pro
        180                 185                 190

Ser Gly Val Pro Asp Arg Phe Ser Gly Ser Lys Ser Gly Thr Ser Ala
    195                 200                 205

Ser Leu Ala Ile Thr Gly Leu Gln Ala Glu Asp Glu Ala Asp Tyr Tyr
210                 215                 220

Cys Gln Ser Tyr Asp Ser Ser Leu Ser Gly Arg Val Phe Gly Gly Gly
225                 230                 235                 240

Thr Lys Leu Thr Val Leu Gly Gly Gln Ala Val Val Thr Gln Glu Pro
            245                 250                 255

Ser Leu Thr Val Ser Pro Gly Gly Thr Val Thr Leu Thr Cys Arg Ser
        260                 265                 270

Ser Thr Gly Ala Val Thr Thr Ser Asn Tyr Ala Asn Trp Val Gln Gln
    275                 280                 285

Lys Pro Gly Gln Ala Pro Arg Gly Leu Ile Gly Gly Thr Asn Lys Arg
290                 295                 300

Ala Pro Gly Thr Pro Ala Arg Phe Ser Gly Ser Leu Leu Gly Gly Lys
305                 310                 315                 320

Ala Ala Leu Thr Leu Ser Gly Val Gln Pro Glu Asp Glu Ala Glu Tyr
            325                 330                 335

Tyr Cys Ala Leu Trp Tyr Ser Asn Leu Trp Val Phe Gly Gly Gly Thr
        340                 345                 350

Lys Leu Thr Val Leu Gly Gln Pro Lys Ala Ala Pro Ser Val Thr Leu
    355                 360                 365

Phe Pro Pro Ser Ser Glu Glu Leu Gln Ala Asn Lys Ala Thr Leu Val
370                 375                 380

Cys Leu Ile Ser Asp Phe Tyr Pro Gly Ala Val Thr Val Ala Trp Lys
385                 390                 395                 400

Ala Asp Ser Ser Pro Val Lys Ala Gly Val Glu Thr Thr Thr Pro Ser
            405                 410                 415
```

| | | | | | | | | | | | | |
|---|---|---|---|---|---|---|---|---|---|---|---|---|
|Lys|Gln|Ser|Asn|Asn|Lys|Tyr|Ala|Ala|Ser|Ser|Tyr|Leu|Ser|Leu|Thr|
| | | |420| | | |425| | | | |430| | | |
|Pro|Glu|Gln|Trp|Lys|Ser|His|Arg|Ser|Tyr|Ser|Cys|Gln|Val|Thr|His|
| | | |435| | | |440| | | | |445| | | |
|Glu|Gly|Ser|Thr|Val|Glu|Lys|Thr|Val|Ala|Pro|Thr|Glu|Cys|Pro|Pro|
| | | |450| | | |455| | | | |460| | | |
|Cys|Ser| | | | | | | | | | | | | | |
|465| | | | | | | | | | | | | | | |

<210> SEQ ID NO 37
<211> LENGTH: 1443
<212> TYPE: DNA
<213> ORGANISM: Artificial Sequence
<220> FEATURE:
<223> OTHER INFORMATION: ITAB1012 HC

<400> SEQUENCE: 37

| | | | | | |
|---|---|---|---|---|---|
|gaggtgcagc|tggtggagtc|aggggggaggc|ttggtccagc|ctgggggatc|actgagactc|60|
|tcctgtgcag|cctctggatt|cacctttagt|aattattgga|tgagctgggt|ccgccaggct|120|
|ccagggaagg|ggctggagtg|ggtggccaac|ataaagcaag|atggaagtga|gaaattctat|180|
|gtggactctg|tgaagggccg|attcaccatc|tccagagaca|acgccaagaa|ctcactgtat|240|
|ctgcaaatga|acagcctgag|agccgaagac|atggctgtct|attactgtgc|gagagtgggg|300|
|ggggcgtggg|agctaggcta|ctggggccag|ggaaccctgg|tcactgtctc|ggccggtggc|360|
|ggtggcagcg|gcggtggtgg|gtccggtggc|ggcggatctg|gcgcgcagtc|tgtactgact|420|
|caaccgccct|cagtgtctgg|ggccccaggg|cagagggtca|ccatctcctg|cactgggagc|480|
|agctccaaca|tcgggtctta|ttatggtgtg|cactggtacc|agcagcttcc|aggaacagcc|540|
|cccaaactcc|tcatctattc|tgacactaat|cgaccctcag|gggtccctga|ccgattctct|600|
|ggctccaagt|ctggcaccctc|ggcctccctg|gccatcactg|gctccaggc|tgaggatgag|660|
|gctgattatt|actgccagtc|gtatgacagc|agcctgagtg|gccgggtgtt|cggcggaggg|720|
|accaagctga|cagtactagg|tggcgaggtg|cagctggtgg|agtctggggg|aggcttggta|780|
|cagcctgggg|ggtccctgag|actctcctgt|gcagcctctg|gattcacctt|taacacctac|840|
|gccatgaact|gggtccgcca|ggctccaggg|aaggggctgg|agtgggtcgc|acgcataaga|900|
|agtaaatata|ataattatgc|aacatattat|gccgattcag|tgaaagaccg|gttcaccatc|960|
|tccagagacg|attccaagaa|cacgctgtat|ctgcaaatga|acagcctgag|agccgaggac|1020|
|acggccgtat|attactgtgt|gagacatggg|aacttcggta|tagctacgt|ttcctggttt|1080|
|gcttactggg|gccaagggac|aatggtcacc|gtctcttcag|ctagcaccaa|gggcccatcc|1140|
|gtcttccccc|tggcaccctc|ctccaagagc|acctctgggg|gcacagcggc|cctgggctgc|1200|
|ctggtcaagg|actacttccc|cgaaccggtg|acggtgtcgt|ggaactcagg|cgccctgacc|1260|
|agcggcgtgc|acaccttccc|ggctgtccta|cagtcctcag|gactctactc|cctcagcagc|1320|
|gtggtgaccg|tgccctccag|cagcttgggc|acccagacct|acatctgcaa|cgtgaatcac|1380|
|aagcccagca|acaccaaggt|ggacaagaaa|gttgagccca|aatcttgtcc|accgtgctca|1440|
|tga| | | | |1443|

<210> SEQ ID NO 38
<211> LENGTH: 1401
<212> TYPE: DNA
<213> ORGANISM: Artificial Sequence
<220> FEATURE:
<223> OTHER INFORMATION: ITAB1012 LC

<400> SEQUENCE: 38

```
gaggtgcagc tggtggagtc aggggggaggc ttggtccagc ctggggggatc actgagactc    60
tcctgtgcag cctctggatt cacctttagt aattattgga tgagctgggt ccgccaggct    120
ccagggaagg ggctggagtg ggtggccaac ataaagcaag atggaagtga aaattctat     180
gtggactctg tgaagggccg attcaccatc tccagagaca acgccaagaa ctcactgtat    240
ctgcaaatga acagcctgag agccgaagac atggctgtct attactgtgc gagagtgggg    300
ggggcgtggg agctaggcta ctggggccag ggaaccctgg tcactgtctc ggccggtggc    360
ggtggcagcg gcggtggtgg gtccggtggc ggcggatctg gcgcgcagtc tgtactgact    420
caaccgccct cagtgtctgg ggccccaggg cagagggtca ccatctcctg cactgggagc    480
agctccaaca tcgggtctta ttatggtgtg cactggtacc agcagcttcc aggaacagcc    540
cccaaactcc tcatctattc tgacactaat cgaccctcag gggtccctga ccgattctct    600
ggctccaagt ctggcacctc ggcctccctg gccatcactg gctccaggc tgaggatgag    660
gctgattatt actgccagtc gtatgacagc agcctgagtg gccgggtgtt cggcggaggg    720
accaagctga cagtactagg tggccaggct gtggtgactc aggagccctc actgactgtg    780
tccccaggag ggacagtcac tctcacctgt cgctcatcca ctgggggctgt tacaactagt    840
aactatgcca actgggtcca gcagaaacct ggacaagcac ccaggggtct gattggtggt    900
accaacaagc gagctccagg taccccctgcc cggttctcag gctccctcct tgggggcaaa    960
gctgccctga cactgtcagg tgtgcagcct gaggacgagg ctgagtatta ctgcgctcta   1020
tggtacagca acctctgggt gttcggcgga gggaccaagc tgaccgtcct aggccaaccg   1080
aaagcggcgc cctcggtcac tctgttcccg ccctcctctg aggagcttca agccaacaag   1140
gccacactgg tgtgtctcat aagtgacttc tacccgggag ccgtgacagt ggcctggaag   1200
gcagatagca gccccgtcaa ggcgggagtg gagaccacca cacctccaa acaaagcaac   1260
aacaagtacg cggccagcag ctatctgagc ctgacgcctg agcagtggaa gtcccacaga   1320
agctacagct gccaggtcac gcatgaaggg agcaccgtgg agaagacagt ggccccctaca   1380
gaatgtccac cgtgctcatg a                                             1401
```

<210> SEQ ID NO 39
<211> LENGTH: 125
<212> TYPE: PRT
<213> ORGANISM: Artificial Sequence
<220> FEATURE:
<223> OTHER INFORMATION: CD3 1VH

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: CD3 2VH

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 41
<211> LENGTH: 125
<212> TYPE: PRT
<213> ORGANISM: Artificial Sequence
<220> FEATURE:
<223> OTHER INFORMATION: CD3 3VH

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 42
<211> LENGTH: 125
<212> TYPE: PRT
<213> ORGANISM: Artificial Sequence

```
<220> FEATURE:
<223> OTHER INFORMATION: CD3 4VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 43
<211> LENGTH: 125
<212> TYPE: PRT
<213> ORGANISM: Artificial Sequence
<220> FEATURE:
<223> OTHER INFORMATION: CD3 11VH

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 44
<211> LENGTH: 109
<212> TYPE: PRT
<213> ORGANISM: Artificial Sequence
<220> FEATURE:
<223> OTHER INFORMATION: CD3 2VL

<400> SEQUENCE: 44

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Phe Gln Gln Lys Pro Gly Gln Ala Pro Arg Gly
            35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 45
<211> LENGTH: 109
<212> TYPE: PRT
<213> ORGANISM: Artificial Sequence
<220> FEATURE:
<223> OTHER INFORMATION: CD3 3VL

<400> SEQUENCE: 45

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 46
<211> LENGTH: 109
<212> TYPE: PRT
<213> ORGANISM: Artificial Sequence
<220> FEATURE:
<223> OTHER INFORMATION: CD3 4VL

<400> SEQUENCE: 46

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
            35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

```
<210> SEQ ID NO 47
<211> LENGTH: 109
<212> TYPE: PRT
<213> ORGANISM: Artificial Sequence
<220> FEATURE:
<223> OTHER INFORMATION: CD3 5VL

<400> SEQUENCE: 47

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Tyr Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```